United States Patent [19]

Lollar

[11] Patent Number: 5,859,204
[45] Date of Patent: Jan. 12, 1999

[54] MODIFIED FACTOR VIII

[75] Inventor: John S. Lollar, Decatur, Ga.

[73] Assignee: Emory University, Atlanta, Ga.

[21] Appl. No.: 670,707

[22] Filed: Jun. 26, 1996

Related U.S. Application Data

[63] Continuation-in-part of PCT/US94/13200 Nov. 15, 1994 and a continuation-in-part of Ser. No. 212,133, Mar. 11, 1994, Pat. No. 5,663,060, which is a continuation-in-part of Ser. No. 864,004, Apr. 7, 1992, Pat. No. 5,364,771.

[51] Int. Cl.$^6$ ................................................. A61K 35/14
[52] U.S. Cl. ........................ 530/383; 435/69.1; 435/69.6
[58] Field of Search ........................... 530/383; 435/69.1, 435/69.6

[56] References Cited

U.S. PATENT DOCUMENTS

| | | | |
|---|---|---|---|
| 4,757,006 | 7/1988 | Toole | 435/70 |
| 4,980,456 | 12/1990 | Scandella et al. | 530/383 |
| 5,149,637 | 9/1992 | Scandella et al. | 435/69.6 |
| 5,171,844 | 12/1992 | Van Ooyen et al. | 530/383 |
| 5,364,771 | 11/1994 | Lollar et al. | 435/69.1 |
| 5,422,260 | 6/1995 | Kaufman et al. | 435/212 |
| 5,618,788 | 4/1997 | Capon et al. | 514/12 |
| 5,618,789 | 4/1997 | Capon et al. | 514/12 |
| 5,633,150 | 5/1997 | Wood et al. | 435/69.6 |
| 5,663,060 | 9/1997 | Lollar et al. | 435/69.6 |

FOREIGN PATENT DOCUMENTS

| | | |
|---|---|---|
| 0 306 968 A2 | 9/1988 | European Pat. Off. |
| 91/07438 | 5/1990 | WIPO |
| WO94/11503 | 5/1994 | WIPO |
| WO/97/03191 | 1/1997 | WIPO |
| WO/97/03193 | 1/1997 | WIPO |

OTHER PUBLICATIONS

Gitschier, J. et al. (1984) *Nature* 312:326–330.
Toole, et al. (1986) *Proc. Nat'l. Acad Sci. USA* 83:5939–5942.
Lubin, et al. (1994) *J. Biol. Chem.* 269:8639–8641.
Church, et al. (1984) *Proc. Nat. Acad. Sci. USA* 81:6934.
Toole, et al. (1984) *Nature* 312:342–347.
Scandella, D. et al. (1995) *Blood* 86:1811–1819.

*Primary Examiner*—Robert A. Wax
*Assistant Examiner*—Enrique D. Longton
*Attorney, Agent, or Firm*—Greenlee Winner and Sullivan

[57] ABSTRACT

Site-specific replacement of amino acids in the region of positions 484–509 of human factor VIII can result in reduction of reactivity to an inhibitory antibody while procoagulant activity is retained. Modified human factor VIII having an immunoreactivity-reducing amino acid substituted for the naturally occurring amino acid is described.

22 Claims, 6 Drawing Sheets

Signal peptide
```
Human  -19  MQIELSTCFF  LCLLRFCFS
Pig         MQLELSTCVF  LCLLPLGFS
Mouse       MQIALFACFF  LSLFNFCSS
            **  *  * *** *      *
```

FIG. 1A

A1 domain
```
Human   1  ATRRYYLGAV  ELSWDYMQSD  LG-ELPVDAR  FPPRVPKSFP  FNTSVVYKKT
Pig        AIRRYYLGAV  ELSWDYRQSE  LLRELHVDTR  FPATAPGALP  LGPSVLYKKT
Mouse      AIRRYYLGAV  ELSWNYIQSD  LLSVLHTDSR  FLPRMSTSFP  FNTSIMYKKT
           **********  ****  * **    *   * * *    *         *  ****

50  LFVEFTDHLF  NIAKPRPPWM  GLLGPTIQAE  VYDTVVITLK  NMASHPVSLH
           VFVEFTDQLF  SVARPRPPWM  GLLGPTIQAE  VYDTVVVTLK  NMASHPVSLH
           VFVEYKDQLF  NIAKPRPPWM  GLLGPTIWTE  VHDTVVITLK  NMASHPVSLH
           ***  *  **    * ******  *******  *  *  ****  ***  **********

100  AVGVSYWKAS  EGAEYDDQTS  QREKEDDKVF  PGGSHTYVWQ  VLKENGPMAS
           AVGVSFWKSS  EGAEYEDHTS  QREKEDDKVL  PGKSQTYVWQ  VLKENGPTAS
           AVGVSYWKAS  EGDEYEDQTS  QMEKEDDKVF  PGESHTYVWQ  VLKENGPMAS
           *****  ** *    ** ****±  **  *******    **  *  *****  ******* **

150  DPLCLTYSYL  SHVDLVKDLN  SGLIGALLVC  REGSLAKEKT  QTLHKFILLF
           DPPCLTYSYL  SHVDLVKDLN  SGLIGALLVC  REGSLTRERT  QNLHEFVLLF
           DPPCLTYSYM  SHVDLVKDLN  SGLIGALLVC  KEGSLSKERT  QMLYQFVLLF
           *********   **********  **********  ****  *  *  *  *  * ***

200  AVFDEGKSWH  SETKNSLMQD  RDAASARAWP  KMHTVNGYVN  RSLPGLIGCH
           AVFDEGKSWH  SARNDSWTRA  MDPAPARAQP  AMHTVNGYVN  RSLPGLIGCH
           AVFDEGKSWH  SETNDSYTQS  MDSASARDWP  KMHTVNGYVN  RSLPGLIGCH
           **********  *      *        * * **  *  *********  **********

250  RKSVYWHVIG  MGTTPEVHSI  FLEGHTFLVR  NHRQASLEIS  PITFLTAQTL
           KKSVYWHVIG  MGTSPEVHSI  FLEGHTFLVR  HHRQASLEIS  PLTFLTAQTF
           RKSVYWHVIG  MGTTPEIHSI  FLEGHTFFVR  NHRQASLEIS  PITFLTAQTL
           *********   *** ** ***  *******  **  *********  *********
                                                  APC/IXa        ♦
      300  LMDLGQFLLF  CHISSHQHDG  MEAYVKVDSC  PEEPQLRMKN  NEEAEDYDDD
           LMDLGQFLLF  CHISSHHHGG  MEAHVRVESC  AEEPQLRRKA  DE-EEDYDDN
           LIDLGQFLLF  CHISSHKHDG  MEAYVKVDSC  PEESQWQKKN  NN-EEMEDYD
            *  ********  ******  *  ***  *  *  **  **  *  *       *  *
                      IIa/Xa
      350  LTDSEMDVVR  FDDDNSPSFI  QIR
           LYDSDMDVVR  LDGDDVSPFI  QIR
           DDLYSEMDMF  TLDYDSSPFI  QIR
                             **  ***
```

FIG. 1B

A2 domain
```
Human  373 SVAKKHPKTW VHYIAAEEED WDYAPLVLAP DDRSYKSQYL NNGPQRIGRK
Pig        SVAKKHPKTW VHYISAEEED WDYAPAVPSP SDRSYKSLYL NSGPQRIGRK
Mouse      SVAKKYPKTW IHYISAEEED WDYAPSVPTS DNGSYKSQYL SNGPHRIGRK
           ***** **** *** ***** ***** *    **** **   ** *****

423 YKKVRFMAYT DETFKTREAI QHESGILGPL LYGEVGDTLL IIFKNQASRP
           YKKARFVAYT DVTFKTRKAI PYESGILGPL LYGEVGDTLL IIFKNKASRP
           YKKVRFIAYT DETFKTRETI QHESGLLGPL LYGEVGDTLL IIFKNQASRP
           *** ** *** * *****  *  *** **** ********** ***** ****
                            A2 Inhibitor epitope
       473 YNIYPHGITD VRPLYSRRLP KGVKHLKDFP ILPGEIFKYK WTVTVEDGPT
           YNIYPHGITD VSALHPGRLL KGWKHLKDMP ILPGETFKYK WTVTVEDGPT
           YNIYPHGITD VSPLHARRLP RGIKHVKDLP IHPGEIFKYK WTVTVEDGPT
           ********** *  *    ** ** ** ** * * *** **** **********
                                          F.IXa binding
                                              APC
       523 KSDPRCLTRY YSSFVNMERD LASGLIGPLL ICYKESVDQR GNQIMSDKRN
           KSDPRCLTRY YSSSINLEKD LASGLIGPLL ICYKESVDQR GNQMMSDKRN
           KSDPRCLTRY YSSFINPERD LASGLIGPLL ICYKESVDQR GNQMMSDKRN
           ********** ***  * * * ********** ********** *** ******

573 VILFSVFDEN RSWYLTENIQ RFLPNPAGVQ LEDPEFQASN IMHSINGYVF
           VILFSVFDEN QSWYLAENIQ RFLPNPDGLQ PQDPEFQASN IMHSINGYVF
           VILFSIFDEN QSWYITENMQ RFLPNAAKTQ PQDPGFQASN IMHSINGYVF
           ***** **** ***  ** * *****  *   ** ***** **********

623 DSLQLSVCLH EVAYWYILSI GAQTDFLSVF FSGYTFKHKM VYEDTLTLFP
           DSLQLSVCLH EVAYWYILSV GAQTDFLSVF FSGYTFKHKM VYEDTLTLFP
           DSLELTVCLH EVAYWHILSV GAQTDFLSIF FSGYTFKHKM VYEDTLTLFP
           *** * **** ***** +** ******** * ********** **********
                                                        ♦♦
       673 FSGETVFMSM ENPGLWILGC HNSDFRNRGM TALLKVSSCD KNTGDYYEDS
           FSGETVFMSM ENPGLWVLGC HNSDLRNRGM TALLKVYSCD RDIGDYYDNT
           FSGETVFMSM ENPGLWVLGC HNSDFRKRGM TALLKVSSCD KSTSDYYEEI
           ********** ********** **** *  *** ********** *   ***
           ♦               IIa/Xa/APC
       723 YEDISAYLLS KNNAIEPR
           YEDIPGFLLS GKNVIEPR
           YEDIPTQLVN ENNVIDPR
           ****  *      * * **
```

FIG. 1C

```
B domain
Human  741 SFSQNSRHPS TRQKQFNATT IPENDIEKTD PWFAHRTPMP KIQNVSSSDL
Pig        SFAQNSRPPS ASQKQFQTIT SPEDDVE-LD PQSQERTQAL EELSVPSGDG
Mouse      SFFQNTNHPN TRKKKFKDST IPKNDMEKIE PQFEEIAEML KVQSVSVSDM
           ** **    *   *  *   *  * **   *              *   *

791 LMLLRQS-PT PHGLSLSDLQ EAKYETFSDD PSPGAIDSNN SLSEMTHFRP
           SMLLGQN-PA PHGSSSSDLQ EARNEA--DD YLPGARERNT APSAAAARLP
           LMLLGQSHPT PHGLFLSDGQ EAIYEAIHDD HSPNAIDSNE GPSKVTQLRP
           *** *      *** *   *  * **  *    **   *  *  *       **

840 QLHHSGDMVF TPESGLQLRL NEKLGTTAAT ELKKLDFKVS ST-SNNLIS-
           ELHHSAERVL TPEP-------- ------EK ELKKLDSKMS SSSDLLKTSP
           ESHHSEKIVF TPQPGLQLRS NKSLETTIEV KWKKLGLQVS SLPSNLMTT-
           *** *      **                    ***         * *

888 TIPSDNLAAGT DNTSSLGPPS MPVHYDSQLD TTLFGKKSSP LTESGGPLSL
           TIPSDTLSAET ERTHSLGPPH PQVNFRSQLG AIVLGKNSSH FIGAGVPLGS
           TILSDNLKATF EKTDSSGFPD MPVHSSSKLS TTAFGKKAYS LVGSHVPLNA
           ** ** *     * * **     *   *       **         **

939 SEENNDSKLL ESGLMNSQES SWGKNVSSTE SGRLFKGKRA HGPALLTKDN
           TEED------ -------HES SLGENVSPVE SDGIFEKERA HGPASLTKDD
           SEENSDSNIL DSTLMYSQES LPRDNILSIE NDRLLREKRF HGIALLTKDN
           **                **     *    *          *  ** * ****

989 ALFKVSISLL KTNKTSNNSA TNRKTHIDGP SLLIENSPSV WQNILESDTE
           VLFKVNISLV KTNKARVYLK TNRKIHIDDA ALLTENRAS- ----------
           TLFKDNVSLM KTNKTYNHST TNEKLHTESP TSIENSTTDL QDAILKVNSE
           ***   **   ****       ** *  *

1039 FKKVTPLIHD RMLMDKNATA LRLNHMSNKT TSSKNMEMVQ QKKEGPIPPD
           ---------- ATFMDKNTTA SGLNHVSN-- ---------- ----------
           IQEVTALIHD GTLLGKNSTY LRLNHMLHRT TSTKNKDIFH RKDEDPIPQD
           *   ***       **      *** *

1089 AQNPDMSFFK MLFLPESARW IQRTHGKNSL NSGQGPSPKQ LVSLGPEKSV
           ------------------W IKGPLGKNPL SSERGPSPEL LTSSGSGKSV
           EENTIMPFSK MLFLSESSNW FKKTNGNNSL NSEQEHSPKQ LVYLMFKKYV
                      *         * *  *    *   **   *        * *

1139 EGQNFLSEKN KVVVGKGEFT KDVGLKEMVF PSSRNLFLTN LDNLHENNTH
           KGQSSGQGRI RVAVEEEELS KG---KEMML PNSELTFLTN SADVQGNDTH
           KNQSFLSEKN KVTVEQDGFT KNIGLKDMAF PHNMSIFLTT LSNVHENGRH
            *             * *  *      *   *   ***         * *

1189 NQEKKIQEEI EKKETLIQEN VVLPQIHTVT GTKNFMKNLF LLSTRQNVEG
           SQGKKSREEM ERREKLVQFK VDLPQVYTAT GTKNFLRNIF HQSTEPSVEG
           NQEKNIQEEI EK-EALIEEK VVLPQVHEAT GSKNFLKDIL ILGTRQNI--
            *    *    * *    *   * ***     * ***
```

FIG. 1D

```
1433 HFLQGAKKNN LSLAILTLEM TGDQREVGSL GTSATNSVTY KKVENTVLPK
     PILQGAKRNN LSLPFLTLEM AGGQGKISAL GKSAAGPLAS GKLEKAVLSS
     NFLKETKINN PSLAILPWNM FIDQGKFTSP GKSNTNSVTY KKRENIIFLK
       *  * **  **  *  *    *         * *        * *

1483 PDLPKTSGKV ELLPKVHIYQ KDLFPTETSN GSPGHLDLVE GSLLQGTEGA
     AGLSEASGKA EFLPKVRVHR EDLLPQKTSN VSCAHGDLGQ EIFLQKTRGP
     PTLPEESGKI ELLPQVSIQE EEILPTETSH GSPGHLNLMK EVFLQKIQGP
       ***      * ** *      *   *   *  * *  *   ***   *

1533 IKWNEANRPG KVPFLRVATE SSAKTPSKLL DPLAWDNHYG TQIPKEEWKS
     VNLNKVNRPG ---------- ---RTPSKLL ---------G PPMPKE-WES
     TKWNKAKRHG ESIKGKTES- -SKNTRSKLL NHHAWDYHYA AQIPKDMWKS
       *   *  *            *  ****                 *  *  *

1583 QEKSPEKTAF KKKDTI-LSLN ACESNHAIAA INEGQNKPEI EVTWAKQGRT
     LEKSPKSTAL RTKDIISLPLD RHESNHSIAA KNEGQAETQR EAAWTKQGGP
     KEKSPEIISI KQEDTI-LSLR PHGNSHSIGA -NEKQNWPQR ETTWVKQGQT
      ****          *  *     **  **  *               *  ***

1633 ERLCSQNPPV LKRHQR
     GRLGAPKPPV LRRHQR
     QRTCSQIPPV LKRHQR
       *        *** * ****
```

Light chain activation peptide
                              ◆                ◆         IIa/Xa
Human 1649 EITRTTLQSDQEEIDYDDTISVEMKKEDFDIYDEDENQSPR
Pig        DISLPTRQPEEDKMDYDDIFSTETKGEDFDIYGEDENQDPR
Mouse      EL--SAFQSEQEATDYDDAITIET-IEDFDIYSEDIKQGPR
             *     *      ****   *  ******  *  * **

FIG. 1E

A3 domain

```
                                         IXa Xa
Human 1690 SFQKKTRHYF IAAVERLWDY GMSSSPHVLR NRAQSGSVPQ FKKVVFQEFT
Pig        SFQKRTRHYF IAAVEQLWDY GMSESPRALR NRAQNGEVPR FKKVVFRERA
Mouse      SVQQKTRHYF IAAVERLWDY GMSTS-HVLR NRYQSDNVPQ FKKVVFQEFT
           *  *  ***** ***** **** *** *  ** ** *   **  ****** *

1740 DGSFTQPLYR GELNEHLGLL GPYIRAEVED NIMVTFRNQA SRPYSFYSSL
           DGSFTNPSYR GELNKHLGLL GPYIRAEVED NIMVTFKNQA SRPYSFYSSL
           DGSFSQPLYR GELNEHLGLL GPYIRAEVED NIMVTFKNQA SRPYSFYSSL
           ****  *  ** ****  ***** ********** ******  *** **********
                                        Factor IXa binding
      1790 ISYEEDQRQG AEPRKNFVKP NETKTYFWKV QHHMAPTKDE FDCKAWAYFS
           ISYPDDQEQG AEPRHNFVQP NETRTYFWKV QHHMAPTEDE FDCKAWAYFS
           ISYKEDQR-G EEPRRNFVKP NETKIYFWKV QHHMAPTEDE FDCKAWAYFS
           ***    **   *  *** *** *** *  ***** ********** **********

1840 DVDLEKDVHS GLIGPLLVCH TNTLNPAHGR QVTVQEFALF FTIFDETKSW
           DVDLEKDVHS GLIGPLLICR ANTLNAAHGR QVTVQEFALF FTIFDETKSW
           DVDLERDMHS GLIGPLLICH ANTLNPAHGR QVSVQEFALL FTIFDETKSW
           ***** *  ** ******* *     **** **** **  ******    **********

1890 YFTENMERNC RAPCNIQMED PTFKENYRFH AINGYIMDTL PGLVMAQDQR
           YFTENVERNC RAPCHLQMED PTLKENYRFH AINGYVMDTL PGLVMAQNQR
           YFTENVKRNC KTPCNFQMED PTLKENYRFH AINGYVMDTL PGLVMAQDQR
           *****  ***   **  ****  **   ** ******* ********** *******  **

1940 IRWYLLSMGS NENIHSIHFS GHVFTVRKKE EYKMALYNLY PGVFETVEML
           IRWYLLSMGS NENIHSIHFS GHVFSVRKKE EYKMAVYNLY PGVFETVEML
           IRWYLLSMGN NENIQSIHFS GHVFTVRKKE EYKMAVYNLY PGVFETLEMI
           *********  ****  ***** ****  ***** ****  **** ****** **
                                Protein C binding
      1990 PSKAGIWRVE CLIGEHLHAG MSTLFLVYSN
           PSKVGIWRIE CLIGEHLQAG MSTTFLVYSK
           PSRAGIWRVE CLIGEHLQAG MSTLFLVYSK
           **  ****  * *******  **  *** ******
```

FIG. 1F

C1 domain
```
Human  2020 KCQTPLGMAS GHIRDFQITA SGQYGQWAPK LARLHYSGSI NAWSTKEPFS
Pig         ECQAPLGMAS GRIRDFQITA SGQYGQWAPK LARLHYSGSI NAWSTKDPHS
Mouse       QCQIPLGMAS GSIRDFQITA SGHYGQWAPN LARLHYSGSI NAWSTKEPFS
            ** ****** * ********* ** ****** ********** ****** * *

2070 WIKVDLLAPM IIHGIKTQGA RQKFSSLYIS QFIIMYSLDG KKWQTYRGNS
           WIKVDLLAPM IIHGIMTQGA RQKFSSLYIS QFIIMYSLDG RNWQSYRGNS
           WIKVDLLAPM IVHGIKTQGA RQKFSSLYIS QFIIMYSLDG KKWLSYQGNS
           ********** * *** **** ********** **********   *  * ***

2120 TGTLMVFFGN VDSSGIKHNI FNPPIIARYI RLHPTHYSIR STLRMELMGCDLN
           TGTLMVFFGN VDASGIKHNI FNPPIVARYI RLHPTHYSIR STLRMELMGCDLN
           TGTLMVFFGN VDSSGIKHNS FNPPIIARYI RLHPTHSSIR STLRMELMGCDLN
           ********** ** ****** ***** **** ****** *** *************
```

FIG. 1G

C2 domain
```
Human  2173 SCSMPLGMES KAISDAQITA SSYFTNMFAT WSPSKARLHL QGRSNAWRPQ
Pig         SCSMPLGMQN KAISDSQITA SSHLSNIFAT WSPSQARLHL QGRTNAWRPR
Mouse       SCSIPLGMES KVISDTQITA SSYFTNMFAT WSPSQARLHL QGRTNAWRPQ
            *** ****   * *** **** **   * *** **** ***** *** *****
                               C2              inhibitor
      2223 VNNPKEWLQV DFQKTMKVTG VTTQGVKSLL TSMYVKEFLI SSSQDGHQHT
           VSSAEEWLQV DLQKTVKVTG ITTQGVKSLL SSMYVKEFLV SSSQDGRRWT
           VNDPKQWLQV DLQKTMKVTG IITQGVKSLF TSMFVKEFLI SSSQDGHHWT
           *     **** * *** **** ********  ** ***** ******  **
               epitope                             Phospholipid
      2273 LFFQNGKVKV FQGNQDSFTP VVNSLDPPLL TRYLRIHPQS WVHQIALRME
           LFLQDGHTKV FQGNQDSSTP VVNALDPPLF TRYLRIHPTS WAQHIALRLE
           QILYNGKVKV FQGNQDSSTP MMNSLDPPLL TRYLRIHPQI WEHQIALRLE
             *  ** ********** *****  ******** * **** *
           binding
      2323 VLGCEAQDLY
           VLGCEAQDLY
           ILGCEAQQQY
           ******  *
```

FIG. 1H

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 9009 base pairs
        ( B ) TYPE: nucleic acid
        ( C ) STRANDEDNESS: double
        ( D ) TOPOLOGY: Not Relevant ( i i ) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Homo sapiens
  ( F ) TISSUE TYPE: Liver ( i x ) FEATURE:
  ( A ) NAME/KEY: misc_feature
  ( B ) LOCATION: 5125..7053
  ( D ) OTHER INFORMATION: /product="Domain Structure"
       / note= "Equivalent to the A3-C1-C2 domain"

( i x ) FEATURE:
  ( A ) NAME/KEY: misc_feature
  ( B ) LOCATION: 1..2277
  ( D ) OTHER INFORMATION: /product="Domain Structure"
       / note= "Equivalent to the A1-A2 domain"

( i x ) FEATURE:
  ( A ) NAME/KEY: misc_feature
  ( B ) LOCATION: 1..2277
  ( D ) OTHER INFORMATION: /product="Domain"
       / note= "cDNA encoding human factorVIII"

( x i ) SEQUENCE DESCRIPTION: SEQ ID NO:1:

```
CAGTGGGTAA GTTCCTTAAA TGCTCTGCAA AGAAATTGGG ACTTTTCATT AAATCAGAAA      60
TTTTACTTTT TTCCCCTCCT GGGAGCTAAA GATATTTTAG AGAAGAATTA ACCTTTTGCT     120
TCTCCAGTTG AACATTTGTA GCAATAAGTC ATGCAAATAG AGCTCTCCAC CTGCTTCTTT     180
CTGTGCCTTT TGCGATTCTG CTTTAGTGCC ACCAGAAGAT ACTACCTGGG TGCAGTGGAA     240
CTGTCATGGG ACTATATGCA AAGTGATCTC GGTGAGCTGC CTGTGGACGC AAGATTTCCT     300
CCTAGAGTGC CAAAATCTTT TCCATTCAAC ACCTCAGTCG TGTACAAAAA GACTCTGTTT     360
GTAGAATTCA CGGTTCACCT TTTCAACATC GCTAAGCCAA GGCCACCCTG GATGGGTCTG     420
CTAGGTCCTA CCATCCAGGC TGAGGTTTAT GATACAGTGG TCATTACACT TAAGAACATG     480
GCTTCCCATC CTGTCAGTCT TCATGCTGTT GGTGTATCCT ACTGGAAAGC TTCTGAGGGA     540
GCTGAATATG ATGATCAGAC CAGTCAAAGG GAGAAAGAAG ATGATAAAGT CTTCCCTGGT     600
GGAAGCCATA CATATGTCTG GCAGGTCCTG AAAGAGAATG GTCCAATGGC CTCTGACCCA     660
CTGTGCCTTA CCTACTCATA TCTTTCTCAT GTGGACCTGG TAAAAGACTT GAATTCAGGC     720
CTCATTGGAG CCCTACTAGT ATGTAGAGAA GGGAGTCTGG CCAAGGAAAA GACACAGACC     780
TTGCACAAAT TTATACTACT TTTTGCTGTA TTTGATGAAG GGAAAAGTTG GCACTCAGAA     840
ACAAAGAACT CCTTGATGCA GGATAGGGAT GCTGCATCTG CTCGGGCCTG GCCTAAAATG     900
CACACAGTCA ATGGTTATGT AAACAGGTCT CTGCCAGGTC TGATTGGATG CCACAGGAAA     960
TCAGTCTATT GGCATGTGAT TGGAATGGGC ACCACTCCTG AAGTGCACTC AATATTCCTC    1020
GAAGGTCACA CATTTCTTGT GAGGAACCAT CGCCAGGCGT CCTTGGAAAT CTCGCCAATA    1080
ACTTTCCTTA CTGCTCAAAC ACTCTTGATG GACCTTGGAC AGTTTCTACT GTTTTGTCAT    1140
ATCTCTTCCC ACCAACATGA TGGCATGGAA GCTTATGTCA AAGTAGACAG CTGTCCAGAG    1200
GAACCCCAAC TACGAATGAA AAATAATGAA GAAGCGGAAG ACTATGATGA TGATCTTACT    1260
GATTCTGAAA TGGATGTGGT CAGGTTTGAT GATGACAACT CTCCTTCCTT TATCCAAATT    1320
CGCTCAGTTG CCAAGAAGCA TCCTAAAACT TGGGTACATT ACATTGCTGC TGAAGAGGAG    1380
GACTGGGACT ATGCTCCCTT AGTCCTCGCC CCCGATGACA GAAGTTATAA AAGTCAATAT    1440
TTGAACAATG GCCCTCAGCG GATTGGTAGG AAGTACAAAA AAGTCCGATT TATGGCATAC    1500
ACAGATGAAA CCTTTAAGAC TCGTGAAGCT ATTCAGCATG AATCAGGAAT CTTGGGACCT    1560
TTACTTTATG GGGAAGTTGG AGACACACTG TTGATTATAT TTAAGAATCA AGCAAGCAGA    1620
```

```
CCATATAACA TCTACCCTCA CGGAATCACT GATGTCCGTC CTTTGTATTC AAGGAGATTA    1680
CCAAAAGGTG TAAAACATTT GAAGGATTTT CCAATTCTGC CAGGAGAAAT ATTCAAATAT    1740
AAATGGACAG TGACTGTAGA AGATGGGCCA ACTAAATCAG ATCCTCGGTG CCTGACCCGC    1800
TATTACTCTA GTTTCGTTAA TATGGAGAGA GATCTAGCTT CAGGACTCAT TGGCCCTCTC    1860
CTCATCTGCT ACAAAGAATC TGTAGATCAA AGAGGAAACC AGATAATGTC AGACAAGAGG    1920
AATGTCATCC TGTTTTCTGT ATTTGATGAG AACCGAAGCT GGTACCTCAC AGAGAATATA    1980
CAACGCTTTC TCCCCAATCC AGCTGGAGTG CAGCTTGAGG ATCCAGAGTT CCAAGCCTCC    2040
AACATCATGC ACAGCATCAA TGGCTATGTT TTTGATAGTT TGCAGTTGTC AGTTTGTTTG    2100
CATGAGGTGG CATACTGGTA CATTCTAAGC ATTGGAGCAC AGACTGACTT CCTTTCTGTC    2160
TTCTTCTCTG GATATACCTT CAAACACAAA ATGGTCTATG AAGACACACT CACCCTATTC    2220
CCATTCTCAG GAGAAACTGT CTTCATGTCG ATGGAAAACC CAGGTCTATG GATTCTGGGG    2280
TGCCACAACT CAGACTTTCG GAACAGAGGC ATGACCGCCT TACTGAAGGT TTCTAGTTGT    2340
GACAAGAACA CTGGTGATTA TTACGAGGAC AGTTATGAAG ATATTTCAGC ATACTTGCTG    2400
AGTAAAAACA ATGCCATTGA ACCAAGAAGC TTCTCCCAGA ATTCAAGACA CCCTAGCACT    2460
AGGCAAAAGC AATTTAATGC CACCACAATT CCAGAAAATG ACATAGAGAA GACTGACCCT    2520
TGGTTTGCAC ACAGAACACC TATGCCTAAA ATACAAAATG TCTCCTCTAG TGATTTGTTG    2580
ATGCTCTTGC GACAGAGTCC TACTCCACAT GGGCTATCCT TATCTGATCT CCAAGAAGCC    2640
AAATATGAGA CTTTTTCTGA TGATCCATCA CCTGGAGCAA TAGACAGTAA TAACAGCCTG    2700
TCTGAAATGA CACACTTCAG GCCACAGCTC CATCACAGTG GGACATGGT ATTTACCCCT     2760
GAGTCAGGCC TCCAATTAAG ATTAAATGAG AAACTGGGGA CAACTGCAGC AACAGAGTTG    2820
AAGAAACTTG ATTTCAAAGT TTCTAGTACA TCAAATAATC TGATTTCAAC AATTCCATCA    2880
GACAATTTGG CAGCAGGTAC TGATAATACA AGTTCCTTAG GACCCCAAG TATGCCAGTT     2940
CATTATGATA GTCAATTAGA TACCACTCTA TTTGGCAAAA AGTCATCTCC CCTTACTGAG    3000
TCTGGTGGAC CTCTGAGCTT GAGTGAAGAA AATAATGATT CAAAGTTGTT AGAATCAGGT    3060
TTAATGAATA GCCAAGAAAG TTCATGGGGA AAAAATGTAT CGTCAACAGA GAGTGGTAGG    3120
TTATTTAAAG GGAAAAGAGC TCATGGACCT GCTTTGTTGA CTAAAGATAA TGCCTTATTC    3180
AAAGTTAGCA TCTCTTTGTT AAAGACAAAC AAAACTTCCA ATAATTCAGC AACTAATAGA    3240
AAGACTCACA TTGATGGCCC ATCATTATTA ATTGAGAATA GTCCATCAGT CTGGCAAAAT    3300
ATATTAGAAA GTGACACTGA GTTTAAAAAA GTGACACCTT TGATTCATGA CAGAATGCTT    3360
ATGGACAAAA ATGCTACAGC TTTGAGGCTA AATCATATGT CAAATAAAAC TACTTCATCA    3420
AAAAACATGG AAATGGTCCA ACAGAAAAAA GAGGGCCCCA TTCCACCAGA TGCACAAAAT    3480
CCAGATATGT CGTTCTTTAA GATGCTATTC TTGCCAGAAT CAGCAAGGTG GATACAAAGG    3540
ACTCATGGAA AGAACTCTCT GAACTCTGGG CAAGGCCCCA GTCCAAAGCA ATTAGTATCC    3600
TTAGGACCAG AAAAATCTGT GGAAGGTCAG AATTTCTTGT CTGAGAAAAA CAAAGTGGTA    3660
GTAGGAAAGG GTGAATTTAC AAAGGACGTA GGACTCAAAG AGATGGTTTT TCCAAGCAGC    3720
AGAAACCTAT TTCTTACTAA CTTGGATAAT TTACATGAAA ATAATACACA CAATCAAGAA    3780
AAAAAAATTC AGGAAGAAAT AGAAAAGAAG GAAACATTAA TCCAAGAGAA TGTAGTTTTG    3840
CCTCAGATAC ATACAGTGAC TGGCACTAAG AATTTCATGA AGAACCTTTT CTTACTGAGC    3900
ACTAGGCAAA ATGTAGAAGG TTCATATGAG GGGGCATATG CTCCAGTACT TCAAGATTTT    3960
AGGTCATTAA ATGATTCAAC AAATAGAACA AAGAAACACA CAGCTCATTT CTCAAAAAAA    4020
```

-continued

```
GGGGAGGAAG AAAACTTGGA AGGCTTGGGA AATCAAACCA AGCAAATTGT AGAGAAATAT    4080
GCATGCACCA CAAGGATATC TCCTAATACA AGCCAGCAGA ATTTGTCAC GCAACGTAGT    4140
AAGAGAGCTT TGAAACAATT CAGACTCCCA CTAGAAGAAA CAGAACTTGA AAAAAGGATA    4200
ATTGTGGATG ACACCTCAAC CCAGTGGTCC AAAAACATGA ACATTTGAC CCCGAGCACC    4260
CTCACACAGA TAGACTACAA TGAGAAGGAG AAAGGGGCCA TTACTCAGTC TCCCTTATCA    4320
GATTGCCTTA CGAGGAGTCA TAGCATCCCT CAAGCAAATA GATCTCCATT ACCCATTGCA    4380
AAGGTATCAT CATTTCCATC TATTAGACCT ATATATCTGA CCAGGGTCCT ATTCCAAGAC    4440
AACTCTTCTC ATCTTCCAGC AGCATCTTAT AGAAAGAAAG ATTCTGGGGT CCAAGAAAGC    4500
AGTCATTTCT TACAAGGAGC CAAAAAAAAT AACCTTTCTT TAGCCATTCT AACCTTGGAG    4560
ATGACTGGTG ATCAAAGAGA GGTTGGCTCC CTGGGGACAA GTGCCACAAA TTCAGTCACA    4620
TACAAGAAAG TTGAGAACAC TGTTCTCCCG AAACCAGACT TGCCCAAAAC ATCTGGCAAA    4680
GTTGAATTGC TTCCAAAAGT TCACATTTAT CAGAAGGACC TATTCCCTAC GGAAACTAGC    4740
AATGGGTCTC CTGGCCATCT GGATCTCGTG GAAGGGAGCC TTCTTCAGGG AACAGAGGGA    4800
GCGATTAAGT GGAATGAAGC AAACAGACCT GGAAAAGTTC CCTTTCTGAG AGTAGCAACA    4860
GAAAGCTCTG CAAAGACTCC CTCCAAGCTA TTGGATCCTC TTGCTTGGGA TAACCACTAT    4920
GGTACTCAGA TACCAAAAGA AGAGTGGAAA TCCCAAGAGA AGTCACCAGA AAAAACAGCT    4980
TTTAAGAAAA AGGATACCAT TTGTCCCTG AACGCTTGTG AAAGCAATCA TGCAATAGCA    5040
GCAATAAATG AGGGACAAAA TAAGCCCGAA ATAGAAGTCA CCTGGGCAAA GCAAGGTAGG    5100
ACTGAAAGGC TGTGCTCTCA AAACCCACCA GTCTTGAAAC GCCATCAACG GGAAATAACT    5160
CGTACTACTC TTCAGTCAGA TCAAGAGGAA ATTGACTATG ATGATACCAT ATCAGTTGAA    5220
ATGAAGAAGG AAGATTTTGA CATTTATGAT GAGGATGAAA ATCAGAGCCC CCGCAGCTTT    5280
CAAAAGAAAA CACGACACTA TTTTATTGCT GCAGTGGAGA GGCTCTGGGA TTATGGGATG    5340
AGTAGCTCCC CACATGTTCT AAGAAACAGG GCTCAGAGTG GCAGTGTCCC TCAGTTCAAG    5400
AAAGTTGTTT TCCAGGAATT TACTGATGGC TCCTTTACTC AGCCCTTATA CCGTGGAGAA    5460
CTAAATGAAC ATTTGGGACT CCTGGGGCCA TATATAAGAG CAGAAGTTGA AGATAATATC    5520
ATGGTAACTT TCAGAAATCA GGCCTCTCGT CCCTATTCCT TCTATTCTAG CCTTATTTCT    5580
TATGAGGAAG ATCAGAGGCA AGGAGCAGAA CCTAGAAAAA ACTTTGTCAA GCCTAATGAA    5640
ACCAAAACTT ACTTTTGGAA AGTGCAACAT CATATGGCAC CCACTAAAGA TGAGTTTGAC    5700
TGCAAAGCCT GGGCTTATTT CTCTGATGTT GACCTGGAAA AAGATGTGCA CTCAGGCCTG    5760
ATTGGACCCC TTCTGGTCTG CCACACTAAC ACACTGAACC CTGCTCATGG GAGACAAGTG    5820
ACAGTACAGG AATTTGCTCT GTTTTTCACC ATCTTTGATG AGACCAAAAG CTGGTACTTC    5880
ACTGAAAATA TGGAAAGAAA CTGCAGGGCT CCCTGCAATA TCCAGATGGA AGATCCCACT    5940
TTTAAAGAGA ATTATCGCTT CCATGCAATC AATGGCTACA TAATGGATAC ACTACCTGGC    6000
TTAGTAATGG CTCAGGATCA AAGGATTCGA TGGTATCTGC TCAGCATGGG CAGCAATGAA    6060
AACATCCATT CTATTCATTT CAGTGGACAT GTGTTCACTG TACGAAAAAA AGAGGAGTAT    6120
AAAATGGCAC TGTACAATCT CTATCCAGGT GTTTTTGAGA CAGTGGAAAT GTTACCATCC    6180
AAAGCTGGAA TTTGGCGGGT GGAATGCCTT ATTGGCGAGC ATCTACATGC TGGGATGAGC    6240
ACACTTTTTC TGGTGTACAG CAATAAGTGT CAGACTCCCC TGGGAATGGC TTCTGGACAC    6300
ATTAGAGATT TTCAGATTAC AGCTTCAGGA CAATATGGAC AGTGGGCCCC AAAGCTGGCC    6360
AGACTTCATT ATTCCGGATC AATCAATGCC TGGAGCACCA AGGAGCCCTT TTCTTGGATC    6420
```

```
AAGGTGGATC TGTTGGCACC AATGATTATT CACGGCATCA AGACCCAGGG TGCCCGTCAG    6480
AAGTTCTCCA GCCTCTACAT CTCTCAGTTT ATCATCATGT ATAGTCTTGA TGGGAAGAAG    6540
TGGCAGACTT ATCGAGGAAA TTCCACTGGA ACCTTAATGG TCTTCTTTGG CAATGTGGAT    6600
TCATCTGGGA TAAAACACAA TATTTTTAAC CCTCCAATTA TTGCTCGATA CATCCGTTTG    6660
CACCCAACTC ATTATAGCAT TCGCAGCACT CTTCGCATGG AGTTGATGGG CTGTGATTTA    6720
AATAGTTGCA GCATGCCATT GGGAATGGAG AGTAAAGCAA TATCAGATGC ACAGATTACT    6780
GCTTCATCCT ACTTACCAA TATGTTTGCC ACCTGGTCTC CTTCAAAAGC TCGACTTCAC    6840
CTCCAAGGGA GGAGTAATGC CTGGAGACCT CAGGTGAATA ATCCAAAAGA GTGGCTGCAA    6900
GTGGACTTCC AGAAGACAAT GAAAGTCACA GGAGTAACTA CTCAGGGAGT AAAATCTCTG    6960
CTTACCAGCA TGTATGTGAA GGAGTTCCTC ATCTCCAGCA GTCAAGATGG CCATCAGTGG    7020
ACTCTCTTTT TTCAGAATGG CAAAGTAAAG GTTTTCAGG GAAATCAAGA CTCCTTCACA     7080
CCTGTGGTGA ACTCTCTAGA CCCACCGTTA CTGACTCGCT ACCTTCGAAT TCACCCCCAG    7140
AGTTGGGTGC ACCAGATTGC CCTGAGGATG GAGGTTCTGG GCTGCGAGGC ACAGGACCTC    7200
TACTGAGGGT GGCCACTGCA GCACCTGCCA CTGCCGTCAC CTCTCCCTCC TCAGCTCCAG    7260
GGCAGTGTCC CTCCCTGGCT TGCCTTCTAC CTTTGTGCTA AATCCTAGCA GACACTGCCT    7320
TGAAGCCTCC TGAATTAACT ATCATCAGTC CTGCATTTCT TTGGTGGGGG CCAGGAGGG    7380
TGCATCCAAT TTAACTTAAC TCTTACCTAT TTTCTGCAGC TGCTCCCAGA TTACTCCTTC    7440
CTTCCAATAT AACTAGGCAA AAAGAAGTGA GGAGAAACCT GCATGAAAGC ATTCTTCCCT    7500
GAAAAGTTAG GCCTCTCAGA GTCACCACTT CCTCTGTTGT AGAAAAACTA TGTGATGAAA    7560
CTTTGAAAAA GATATTTATG ATGTTAACAT TTCAGGTTAA GCCTCATACG TTTAAAATAA    7620
AACTCTCAGT TGTTTATTAT CCTGATCAAG CATGGAACAA AGCATGTTTC AGGATCAGAT    7680
CAATACAATC TTGGAGTCAA AAGGCAAATC ATTTGGACAA TCTGCAAAAT GGAGAGAATA    7740
CAATAACTAC TACAGTAAAG TCTGTTTCTG CTTCCTTACA CATAGATATA ATTATGTTAT    7800
TTAGTCATTA TGAGGGGCAC ATTCTTATCT CCAAAACTAG CATTCTTAAA CTGAGAATTA    7860
TAGATGGGGT TCAAGAATCC CTAAGTCCCC TGAAATTATA TAAGGCATTC TGTATAAATG    7920
CAAATGTGCA TTTTTCTGAC GAGTGTCCAT AGATATAAAG CCATTGGTCT TAATTCTGAC    7980
CAATAAAAAA ATAAGTCAGG AGGATGCAAT TGTTGAAAGC TTTGAAATAA AATAACATGT    8040
CTTCTTGAAA TTTGTGATGG CCAAGAAAGA AAATGATGAT GACATTAGGC TTCTAAAGGA    8100
CATACATTTA ATATTTCTGT GGAAATATGA GGAAAATCCA TGGTTATCTG AGATAGGAGA    8160
TACAAACTTT GTAATTCTAA TAATGCACTC AGTTTACTCT CTCCCTCTAC TAATTTCCTG    8220
CTGAAAATAA CACAACAAA ATGTAACAGG GGAAATTATA TACCGTGACT GAAAACTAGA     8280
GTCCTACTTA CATAGTTGAA ATATCAAGGA GGTCAGAAGA AAATTGGACT GGTGAAAACA    8340
GAAAAAACAC TCCAGTCTGC CATATCACCA CACAATAGGA TCCCCCTTCT TGCCCTCCAC    8400
CCCCATAAGA TTGTGAAGGG TTTACTGCTC CTTCCATCTG CCTGCACCCC TTCACTATGA    8460
CTACACAGAA CTCTCCTGAT AGTAAAGGGG GCTGGAGGCA AGGATAAGTT ATAGAGCAGT    8520
TGGAGGAAGC ATCCAAAGAC TGCAACCCAG GGCAAATGGA AAACAGGAGA TCCTAATATG    8580
AAAGAAAAAT GGATCCCAAT CTGAGAAAAG GCAAAAGAAT GGCTACTTTT TTCTATGCTG    8640
GAGTATTTTC TAATAATCCT GCTTGACCCT TATCTGACCT CTTTGGAAAC TATAACATAG    8700
CTGTCACAGT ATAGTCACAA TCCACAAATG ATGCAGGTGC AAATGGTTTA TAGCCCTGTG    8760
AAGTTCTTAA AGTTTAGAGG CTAACTTACA GAAATGAATA AGTTGTTTTG TTTTATAGCC    8820
```

CGGTAGAGGA GTTAACCCCA AAGGTGATAT GGTTTTATTT CCTGTTATGT TTAACTTGAT  8880

AATCTTATTT TGGCATTCTT TTCCCATTGA CTATATACAT CTCTATTTCT CAAATGTTCA  8940

TGGAACTAGC TCTTTTATTT TCCTGCTGGT TTCTTCAGTA ATGAGTTAAA TAAAACATTG  9000

ACACATACA  9009

( 2 ) INFORMATION FOR SEQ ID NO:2:

( i ) SEQUENCE CHARACTERISTICS:
  ( A ) LENGTH: 2332 amino acids
  ( B ) TYPE: amino acid
  ( C ) STRANDEDNESS: single
  ( D ) TOPOLOGY: Not Relevant ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
  ( A ) ORGANISM: Homo sapiens
  ( F ) TISSUE TYPE: Liver ( x i ) SEQUENCE DESCRIPTION: SEQ ID NO:2:

```
Ala  Thr  Arg  Arg  Tyr  Tyr  Leu  Gly  Ala  Val  Glu  Leu  Ser  Trp  Asp  Tyr
 1              5                        10                       15

Met  Gln  Ser  Asp  Leu  Gly  Glu  Leu  Pro  Val  Asp  Ala  Arg  Phe  Pro  Pro
               20                       25                       30

Arg  Val  Pro  Lys  Ser  Phe  Pro  Phe  Asn  Thr  Ser  Val  Val  Tyr  Lys  Lys
                35                       40                       45

Thr  Leu  Phe  Val  Glu  Phe  Thr  Val  His  Leu  Phe  Asn  Ile  Ala  Lys  Pro
           50                       55                       60

Arg  Pro  Pro  Trp  Met  Gly  Leu  Leu  Gly  Pro  Thr  Ile  Gln  Ala  Glu  Val
 65                      70                       75                       80

Tyr  Asp  Thr  Val  Val  Ile  Thr  Leu  Lys  Asn  Met  Ala  Ser  His  Pro  Val
                     85                       90                       95

Ser  Leu  His  Ala  Val  Gly  Val  Ser  Tyr  Trp  Lys  Ala  Ser  Glu  Gly  Ala
                    100                      105                      110

Glu  Tyr  Asp  Asp  Gln  Thr  Ser  Gln  Arg  Glu  Lys  Glu  Asp  Asp  Lys  Val
               115                      120                      125

Phe  Pro  Gly  Gly  Ser  His  Thr  Tyr  Val  Trp  Gln  Val  Leu  Lys  Glu  Asn
          130                      135                      140

Gly  Pro  Met  Ala  Ser  Asp  Pro  Leu  Cys  Leu  Thr  Tyr  Ser  Tyr  Leu  Ser
145                      150                      155                      160

His  Val  Asp  Leu  Val  Lys  Asp  Leu  Asn  Ser  Gly  Leu  Ile  Gly  Ala  Leu
                    165                      170                      175

Leu  Val  Cys  Arg  Glu  Gly  Ser  Leu  Ala  Lys  Glu  Lys  Thr  Gln  Thr  Leu
               180                      185                      190

His  Lys  Phe  Ile  Leu  Leu  Phe  Ala  Val  Phe  Asp  Glu  Gly  Lys  Ser  Trp
          195                      200                      205

His  Ser  Glu  Thr  Lys  Asn  Ser  Leu  Met  Gln  Asp  Arg  Asp  Ala  Ala  Ser
     210                      215                      220

Ala  Arg  Ala  Trp  Pro  Lys  Met  His  Thr  Val  Asn  Gly  Tyr  Val  Asn  Arg
225                      230                      235                      240

Ser  Leu  Pro  Gly  Leu  Ile  Gly  Cys  His  Arg  Lys  Ser  Val  Tyr  Trp  His
                    245                      250                      255
```

-continued

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Met Asp Leu Gly
    290                 295                 300

Gln Phe Leu Leu Phe Cys His Ile Ser Ser His Gln His Asp Gly Met
305                     310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                     390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                     470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                     550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                     630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685
```

| | | | | | | | | | | | | | | |
|---|---|---|---|---|---|---|---|---|---|---|---|---|---|---|
| Ile | Leu | Gly | Cys | His | Asn | Ser | Asp | Phe | Arg | Asn | Arg | Gly | Met | Thr | Ala |
| | 690 | | | | 695 | | | | | 700 | | | | |
| Leu | Leu | Lys | Val | Ser | Ser | Cys | Asp | Lys | Asn | Thr | Gly | Asp | Tyr | Tyr | Glu |
| 705 | | | | | 710 | | | | | 715 | | | | | 720 |
| Asp | Ser | Tyr | Glu | Asp | Ile | Ser | Ala | Tyr | Leu | Leu | Ser | Lys | Asn | Asn | Ala |
| | | | | 725 | | | | | 730 | | | | | 735 | |
| Ile | Glu | Pro | Arg | Ser | Phe | Ser | Gln | Asn | Ser | Arg | His | Pro | Ser | Thr | Arg |
| | | | 740 | | | | | 745 | | | | | 750 | | |
| Gln | Lys | Gln | Phe | Asn | Ala | Thr | Thr | Ile | Pro | Glu | Asn | Asp | Ile | Glu | Lys |
| | | 755 | | | | | 760 | | | | | 765 | | | |
| Thr | Asp | Pro | Trp | Phe | Ala | His | Arg | Thr | Pro | Met | Pro | Lys | Ile | Gln | Asn |
| | 770 | | | | | 775 | | | | | 780 | | | | |
| Val | Ser | Ser | Ser | Asp | Leu | Leu | Met | Leu | Leu | Arg | Gln | Ser | Pro | Thr | Pro |
| 785 | | | | | 790 | | | | | 795 | | | | | 800 |
| His | Gly | Leu | Ser | Leu | Ser | Asp | Leu | Gln | Glu | Ala | Lys | Tyr | Glu | Thr | Phe |
| | | | | | 805 | | | | | 810 | | | | | 815 |
| Ser | Asp | Asp | Pro | Ser | Pro | Gly | Ala | Ile | Asp | Ser | Asn | Asn | Ser | Leu | Ser |
| | | | | 820 | | | | | 825 | | | | | 830 | |
| Glu | Met | Thr | His | Phe | Arg | Pro | Gln | Leu | His | His | Ser | Gly | Asp | Met | Val |
| | | | 835 | | | | | 840 | | | | | 845 | | |
| Phe | Thr | Pro | Glu | Ser | Gly | Leu | Gln | Leu | Arg | Leu | Asn | Glu | Lys | Leu | Gly |
| | 850 | | | | | 855 | | | | | 860 | | | | |
| Thr | Thr | Ala | Ala | Thr | Glu | Leu | Lys | Lys | Leu | Asp | Phe | Lys | Val | Ser | Ser |
| 865 | | | | | 870 | | | | | 875 | | | | | 880 |
| Thr | Ser | Asn | Asn | Leu | Ile | Ser | Thr | Ile | Pro | Ser | Asp | Asn | Leu | Ala | Ala |
| | | | | 885 | | | | | 890 | | | | | 895 | |
| Gly | Thr | Asp | Asn | Thr | Ser | Ser | Leu | Gly | Pro | Pro | Ser | Met | Pro | Val | His |
| | | | 900 | | | | | 905 | | | | | 910 | | |
| Tyr | Asp | Ser | Gln | Leu | Asp | Thr | Thr | Leu | Phe | Gly | Lys | Lys | Ser | Ser | Pro |
| | | 915 | | | | | 920 | | | | | 925 | | | |
| Leu | Thr | Glu | Ser | Gly | Gly | Pro | Leu | Ser | Leu | Ser | Glu | Glu | Asn | Asn | Asp |
| | 930 | | | | | 935 | | | | | 940 | | | | |
| Ser | Lys | Leu | Leu | Glu | Ser | Gly | Leu | Met | Asn | Ser | Gln | Glu | Ser | Ser | Trp |
| 945 | | | | | 950 | | | | | 955 | | | | | 960 |
| Gly | Lys | Asn | Val | Ser | Ser | Thr | Glu | Ser | Gly | Arg | Leu | Phe | Lys | Gly | Lys |
| | | | | 965 | | | | | 970 | | | | | 975 | |
| Arg | Ala | His | Gly | Pro | Ala | Leu | Leu | Thr | Lys | Asp | Asn | Ala | Leu | Phe | Lys |
| | | | 980 | | | | | 985 | | | | | 990 | | |
| Val | Ser | Ile | Ser | Leu | Leu | Lys | Thr | Asn | Lys | Thr | Ser | Asn | Asn | Ser | Ala |
| | | 995 | | | | | 1000 | | | | | 1005 | | | |
| Thr | Asn | Arg | Lys | Thr | His | Ile | Asp | Gly | Pro | Ser | Leu | Leu | Ile | Glu | Asn |
| | 1010 | | | | | 1015 | | | | | 1020 | | | | |
| Ser | Pro | Ser | Val | Trp | Gln | Asn | Ile | Leu | Glu | Ser | Asp | Thr | Glu | Phe | Lys |
| 1025 | | | | | 1030 | | | | | 1035 | | | | | 1040 |
| Lys | Val | Thr | Pro | Leu | Ile | His | Asp | Arg | Met | Leu | Met | Asp | Lys | Asn | Ala |
| | | | | | 1045 | | | | | 1050 | | | | | 1055 |
| Thr | Ala | Leu | Arg | Leu | Asn | His | Met | Ser | Asn | Lys | Thr | Thr | Ser | Ser | Lys |
| | | | | 1060 | | | | | 1065 | | | | | 1070 | |
| Asn | Met | Glu | Met | Val | Gln | Gln | Lys | Lys | Glu | Gly | Pro | Ile | Pro | Pro | Asp |
| | | | 1075 | | | | | 1080 | | | | | 1085 | | |
| Ala | Gln | Asn | Pro | Asp | Met | Ser | Phe | Phe | Lys | Met | Leu | Phe | Leu | Pro | Glu |
| | 1090 | | | | | 1095 | | | | | 1100 | | | | |
| Ser | Ala | Arg | Trp | Ile | Gln | Arg | Thr | His | Gly | Lys | Asn | Ser | Leu | Asn | Ser |

```
        1105                1110                1115                1120

Gly  Gln  Gly  Pro  Ser  Pro  Lys  Gln  Leu  Val  Ser  Leu  Gly  Pro  Glu  Lys
                    1125                1130                1135

Ser  Val  Glu  Gly  Gln  Asn  Phe  Leu  Ser  Glu  Lys  Asn  Lys  Val  Val  Val
               1140                1145                1150

Gly  Lys  Gly  Glu  Phe  Thr  Lys  Asp  Val  Gly  Leu  Lys  Glu  Met  Val  Phe
                    1155                1160                1165

Pro  Ser  Ser  Arg  Asn  Leu  Phe  Leu  Thr  Asn  Leu  Asp  Asn  Leu  His  Glu
          1170                1175                1180

Asn  Asn  Thr  His  Asn  Gln  Glu  Lys  Lys  Ile  Gln  Glu  Glu  Ile  Glu  Lys
1185                1190                1195                          1200

Lys  Glu  Thr  Leu  Ile  Gln  Glu  Asn  Val  Val  Leu  Pro  Gln  Ile  His  Thr
                    1205                1210                1215

Val  Thr  Gly  Thr  Lys  Asn  Phe  Met  Lys  Asn  Leu  Phe  Leu  Leu  Ser  Thr
                    1220                1225                1230

Arg  Gln  Asn  Val  Glu  Gly  Ser  Tyr  Glu  Gly  Ala  Tyr  Ala  Pro  Val  Leu
               1235                1240                1245

Gln  Asp  Phe  Arg  Ser  Leu  Asn  Asp  Ser  Thr  Asn  Arg  Thr  Lys  Lys  His
     1250                1255                1260

Thr  Ala  His  Phe  Ser  Lys  Lys  Gly  Glu  Glu  Glu  Asn  Leu  Glu  Gly  Leu
1265                1270                1275                          1280

Gly  Asn  Gln  Thr  Lys  Gln  Ile  Val  Glu  Lys  Tyr  Ala  Cys  Thr  Thr  Arg
                    1285                1290                1295

Ile  Ser  Pro  Asn  Thr  Ser  Gln  Gln  Asn  Phe  Val  Thr  Gln  Arg  Ser  Lys
                    1300                1305                1310

Arg  Ala  Leu  Lys  Gln  Phe  Arg  Leu  Pro  Leu  Glu  Glu  Thr  Glu  Leu  Glu
               1315                1320                1325

Lys  Arg  Ile  Ile  Val  Asp  Asp  Thr  Ser  Thr  Gln  Trp  Ser  Lys  Asn  Met
                    1330                1335                1340

Lys  His  Leu  Thr  Pro  Ser  Thr  Leu  Thr  Gln  Ile  Asp  Tyr  Asn  Glu  Lys
1345                1350                1355                          1360

Glu  Lys  Gly  Ala  Ile  Thr  Gln  Ser  Pro  Leu  Ser  Asp  Cys  Leu  Thr  Arg
                    1365                1370                1375

Ser  His  Ser  Ile  Pro  Gln  Ala  Asn  Arg  Ser  Pro  Leu  Pro  Ile  Ala  Lys
                    1380                1385                1390

Val  Ser  Ser  Phe  Pro  Ser  Ile  Arg  Pro  Ile  Tyr  Leu  Thr  Arg  Val  Leu
                    1395                1400                1405

Phe  Gln  Asp  Asn  Ser  Ser  His  Leu  Pro  Ala  Ala  Ser  Tyr  Arg  Lys  Lys
                    1410                1415                1420

Asp  Ser  Gly  Val  Gln  Glu  Ser  Ser  His  Phe  Leu  Gln  Gly  Ala  Lys  Lys
1425                1430                1435                          1440

Asn  Asn  Leu  Ser  Leu  Ala  Ile  Leu  Thr  Leu  Glu  Met  Thr  Gly  Asp  Gln
                    1445                1450                1455

Arg  Glu  Val  Gly  Ser  Leu  Gly  Thr  Ser  Ala  Thr  Asn  Ser  Val  Thr  Tyr
                    1460                1465                1470

Lys  Lys  Val  Glu  Asn  Thr  Val  Leu  Pro  Lys  Pro  Asp  Leu  Pro  Lys  Thr
                    1475                1480                1485

Ser  Gly  Lys  Val  Glu  Leu  Leu  Pro  Lys  Val  His  Ile  Tyr  Gln  Lys  Asp
                    1490                1495                1500

Leu  Phe  Pro  Thr  Glu  Thr  Ser  Asn  Gly  Ser  Pro  Gly  His  Leu  Asp  Leu
                    1505                1510                1515                1520

Val  Glu  Gly  Ser  Leu  Leu  Gln  Gly  Thr  Glu  Gly  Ala  Ile  Lys  Trp  Asn
                    1525                1530                1535
```

-continued

```
Glu Ala Asn Arg Pro Gly Lys Val Pro Phe Leu Arg Val Ala Thr Glu
            1540                1545                1550

Ser Ser Ala Lys Thr Pro Ser Lys Leu Leu Asp Pro Leu Ala Trp Asp
        1555                1560                1565

Asn His Tyr Gly Thr Gln Ile Pro Lys Glu Glu Trp Lys Ser Gln Glu
    1570                1575                1580

Lys Ser Pro Glu Lys Thr Ala Phe Lys Lys Asp Thr Ile Leu Ser
1585                1590                1595                1600

Leu Asn Ala Cys Glu Ser Asn His Ala Ile Ala Ala Ile Asn Glu Gly
            1605                1610                1615

Gln Asn Lys Pro Glu Ile Glu Val Thr Trp Ala Lys Gln Gly Arg Thr
        1620                1625                1630

Glu Arg Leu Cys Ser Gln Asn Pro Pro Val Leu Lys Arg His Gln Arg
    1635                1640                1645

Glu Ile Thr Arg Thr Thr Leu Gln Ser Asp Gln Glu Glu Ile Asp Tyr
1650                1655                1660

Asp Asp Thr Ile Ser Val Glu Met Lys Lys Glu Asp Phe Asp Ile Tyr
            1665                1670                1675                1680

Asp Glu Asp Glu Asn Gln Ser Pro Arg Ser Phe Gln Lys Lys Thr Arg
        1685                1690                1695

His Tyr Phe Ile Ala Ala Val Glu Arg Leu Trp Asp Tyr Gly Met Ser
    1700                1705                1710

Ser Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe Thr
            1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
        1780                1785                1790

Glu Glu Asp Gln Arg Gln Gly Ala Glu Pro Arg Lys Asn Phe Val Lys
    1795                1800                1805

Pro Asn Glu Thr Lys Thr Tyr Phe Trp Lys Val Gln His His Met Ala
    1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
        1860                1865                1870

Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
            1890                1895                1900

Ile Gln Met Glu Asp Pro Thr Phe Lys Glu Asn Tyr Arg Phe His Ala
        1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
        1955                1960                1965
```

Glu Glu Tyr Lys Met Ala Leu Tyr Asn Leu Tyr Pro Gly Val Phe Glu
1970                     1975                    1980

Thr Val Glu Met Leu Pro Ser Lys Ala Gly Ile Trp Arg Val Glu Cys
1985                    1990                    1995                    2000

Leu Ile Gly Glu His Leu His Ala Gly Met Ser Thr Leu Phe Leu Val
            2005                    2010                    2015

Tyr Ser Asn Lys Cys Gln Thr Pro Leu Gly Met Ala Ser Gly His Ile
            2020                    2025                    2030

Arg Asp Phe Gln Ile Thr Ala Ser Gly Gln Tyr Gly Gln Trp Ala Pro
            2035                    2040                    2045

Lys Leu Ala Arg Leu His Tyr Ser Gly Ser Ile Asn Ala Trp Ser Thr
            2050                    2055                    2060

Lys Glu Pro Phe Ser Trp Ile Lys Val Asp Leu Leu Ala Pro Met Ile
2065                    2070                    2075                    2080

Ile His Gly Ile Lys Thr Gln Gly Ala Arg Gln Lys Phe Ser Ser Leu
            2085                    2090                    2095

Tyr Ile Ser Gln Phe Ile Ile Met Tyr Ser Leu Asp Gly Lys Lys Trp
            2100                    2105                    2110

Gln Thr Tyr Arg Gly Asn Ser Thr Gly Thr Leu Met Val Phe Phe Gly
            2115                    2120                    2125

Asn Val Asp Ser Ser Gly Ile Lys His Asn Ile Phe Asn Pro Pro Ile
            2130                    2135                    2140

Ile Ala Arg Tyr Ile Arg Leu His Pro Thr His Tyr Ser Ile Arg Ser
2145                    2150                    2155                    2160

Thr Leu Arg Met Glu Leu Met Gly Cys Asp Leu Asn Ser Cys Ser Met
                2165                    2170                    2175

Pro Leu Gly Met Glu Ser Lys Ala Ile Ser Asp Ala Gln Ile Thr Ala
                2180                    2185                    2190

Ser Ser Tyr Phe Thr Asn Met Phe Ala Thr Trp Ser Pro Ser Lys Ala
            2195                    2200                    2205

Arg Leu His Leu Gln Gly Arg Ser Asn Ala Trp Arg Pro Gln Val Asn
            2210                    2215                    2220

Asn Pro Lys Glu Trp Leu Gln Val Asp Phe Gln Lys Thr Met Lys Val
2225                    2230                    2235                    2240

Thr Gly Val Thr Thr Gln Gly Val Lys Ser Leu Leu Thr Ser Met Tyr
                2245                    2250                    2255

Val Lys Glu Phe Leu Ile Ser Ser Ser Gln Asp Gly His Gln Trp Thr
            2260                    2265                    2270

Leu Phe Phe Gln Asn Gly Lys Val Lys Val Phe Gln Gly Asn Gln Asp
            2275                    2280                    2285

Ser Phe Thr Pro Val Val Asn Ser Leu Asp Pro Pro Leu Leu Thr Arg
            2290                    2295                    2300

Tyr Leu Arg Ile His Pro Gln Ser Trp Val His Gln Ile Ala Leu Arg
2305                    2310                    2315                    2320

Met Glu Val Leu Gly Cys Glu Ala Gln Asp Leu Tyr
                2325                    2330

( 2 ) INFORMATION FOR SEQ ID NO:3:

( i ) SEQUENCE CHARACTERISTICS:
        ( A ) LENGTH: 1130 base pairs
        ( B ) TYPE: nucleic acid
        ( C ) STRANDEDNESS: double
        ( D ) TOPOLOGY: Not Relevant ( i i ) MOLECULE TYPE: cDNA to mRNA (  i i i ) HYPOTHETICAL: NO (  i v ) ANTI-SENSE: NO (  v i ) ORIGINAL SOURCE:
       ( A ) ORGANISM: Porcine
       ( F ) TISSUE TYPE: blood (  i x ) FEATURE:
       ( A ) NAME/KEY: misc_feature
       ( B ) LOCATION: 1..1130
       ( D ) OTHER INFORMATION: /product="region"
              / note= "cDNA encoding A2 domain of porcine factorVIII"

(  x i ) SEQUENCE DESCRIPTION: SEQ ID NO:3:

```
TAAGCACCCT   AAGACGTGGG   TGCACTACAT   CTCTGCAGAG   GAGGAGGACT   GGGACTACGC        60
CCCCGCGGTC   CCCAGCCCCA   GTGACAGAAG   TTATAAAAGT   CTCTACTTGA   ACAGTGGTCC       120
TCAGCGAATT   GGTAGGAAAT   ACAAAAAAGC   TCGATTCGTC   GCTTACACGG   ATGTAACATT       180
TAAGACTCGT   AAAGCTATTC   CGTATGAATC   AGGAATCCTG   GGACCTTTAC   TTTATGGAGA       240
AGTTGGAGAC   ACACTTTTGA   TTATATTTAA   GAATAAAGCG   AGCCGACCAT   ATAACATCTA       300
CCCTCATGGA   ATCACTGATG   TCAGCGCTTT   GCACCCAGGG   AGACTTCTAA   AAGGTTGGAA       360
ACATTTGAAA   GACATGCCAA   TTCTGCCAGG   AGAGACTTTC   AAGTATAAAT   GGACAGTGAC       420
TGTGGAAGAT   GGGCCAACCA   AGTCCGATCC   TCGGTGCCTG   ACCCGCTACT   ACTCGAGCTC       480
CATTAATCTA   GAGAAAGATC   TGGCTTCGGG   ACTCATTGGC   CCTCTCCTCA   TCTGCTACAA       540
AGAATCTGTA   GACCAAAGAG   GAAACCAGAT   GATGTCAGAC   AAGAGAAACG   TCATCCTGTT       600
TTCTGTATTC   GATGAGAATC   AAAGCTGGTA   CCTCGCAGAG   AATATTCAGC   GCTTCCTCCC       660
CAATCCGGAT   GGATTACAGC   CCCAGGATCC   AGAGTTCCAA   GCTTCTAACA   TCATGCACAG       720
CATCAATGGC   TATGTTTTTG   ATAGCTTGCA   GCTGTCGGTT   TGTTTGCACG   AGGTGGCATA       780
CTGGTACATT   CTAAGTGTTG   GAGCACAGAC   GGACTTCCTC   TCCGTCTTCT   TCTCTGGCTA       840
CACCTTCAAA   CACAAAATGG   TCTATGAAGA   CACACTCACC   CTGTTCCCCT   TCTCAGGAGA       900
AACGGTCTTC   ATGTCAATGG   AAAACCCAGG   TCTCTGGGTC   CTAGGGTGCC   ACAACTCAGA       960
CTTGCGGAAC   AGAGGGATGA   CAGCCTTACT   GAAGGTGTAT   AGTTGTGACA   GGGACATTGG      1020
TGATTATTAT   GACAACACTT   ATGAAGATAT   TCCAGGCTTC   TTGCTGAGTG   GAAAGAATGT      1080
CATTGAACCC   AGAAGCTTTG   CCCAGAATTC   AAGACCCCCT   AGTGCGAGCA                   1130
```

( 2 ) INFORMATION FOR SEQ ID NO:4:

(  i ) SEQUENCE CHARACTERISTICS:
              ( A ) LENGTH: 368 amino acids
              ( B ) TYPE: amino acid
              ( C ) STRANDEDNESS: single
              ( D ) TOPOLOGY: linear (  i i ) MOLECULE TYPE: protein (  i i i ) HYPOTHETICAL: YES (  i v ) ANTI-SENSE: NO (  v ) FRAGMENT TYPE: N-terminal (  v i ) ORIGINAL SOURCE:
       ( A ) ORGANISM: Porcine
       ( F ) TISSUE TYPE: spleen (  i x ) FEATURE:
       ( A ) NAME/KEY: Protein
       ( B ) LOCATION: 1..368
       ( D ) OTHER INFORMATION: /note= "Predicted amino acid -continued sequence of porcine factor VIII A2 domain, defined as
residues homologous to human factor VIII, amino acids
373-740. Residues 1-4 are from known porcine amino
acid sequence."

( x i ) SEQUENCE DESCRIPTION: SEQ ID NO:4:

| Ser | Val | Ala | Lys | Lys | His | Pro | Lys | Thr | Trp | Val | His | Tyr | Ile | Ser | Ala |
|-----|-----|-----|-----|-----|-----|-----|-----|-----|-----|-----|-----|-----|-----|-----|-----|
| 1 | | | | 5 | | | | 10 | | | | | | 15 | |
| Glu | Glu | Glu | Asp | Trp | Asp | Tyr | Ala | Pro | Ala | Val | Pro | Ser | Pro | Ser | Asp |
| | | | 20 | | | | | 25 | | | | | 30 | | |
| Arg | Ser | Tyr | Lys | Ser | Leu | Tyr | Leu | Asn | Ser | Gly | Pro | Gln | Arg | Ile | Gly |
| | | 35 | | | | | 40 | | | | | 45 | | | |
| Arg | Lys | Tyr | Lys | Lys | Ala | Arg | Phe | Val | Ala | Tyr | Thr | Asp | Val | Thr | Phe |
| | 50 | | | | | 55 | | | | | 60 | | | | |
| Lys | Thr | Arg | Lys | Ala | Ile | Pro | Tyr | Glu | Ser | Gly | Ile | Leu | Gly | Pro | Leu |
| 65 | | | | | 70 | | | | | 75 | | | | | 80 |
| Leu | Tyr | Gly | Glu | Val | Gly | Asp | Thr | Leu | Leu | Ile | Ile | Phe | Lys | Asn | Lys |
| | | | | 85 | | | | | 90 | | | | | 95 | |
| Ala | Ser | Arg | Pro | Tyr | Asn | Ile | Tyr | Pro | His | Gly | Ile | Thr | Asp | Val | Ser |
| | | | 100 | | | | | 105 | | | | | 110 | | |
| Ala | Leu | His | Pro | Gly | Arg | Leu | Leu | Lys | Gly | Trp | Lys | His | Leu | Lys | Asp |
| | | 115 | | | | | 120 | | | | | 125 | | | |
| Met | Pro | Ile | Leu | Pro | Gly | Glu | Thr | Phe | Lys | Tyr | Lys | Trp | Thr | Val | Thr |
| | 130 | | | | | 135 | | | | | 140 | | | | |
| Val | Glu | Asp | Gly | Pro | Thr | Lys | Ser | Asp | Pro | Arg | Cys | Leu | Thr | Arg | Tyr |
| 145 | | | | | 150 | | | | | 155 | | | | | 160 |
| Tyr | Ser | Ser | Ser | Ile | Asn | Leu | Glu | Lys | Asp | Leu | Ala | Ser | Gly | Leu | Ile |
| | | | | 165 | | | | | 170 | | | | | 175 | |
| Gly | Pro | Leu | Leu | Ile | Cys | Tyr | Lys | Glu | Ser | Val | Asp | Gln | Arg | Gly | Asn |
| | | | 180 | | | | | 185 | | | | | 190 | | |
| Gln | Met | Met | Ser | Asp | Lys | Arg | Asn | Val | Ile | Leu | Phe | Ser | Val | Phe | Asp |
| | | 195 | | | | | 200 | | | | | 205 | | | |
| Glu | Asn | Gln | Ser | Trp | Tyr | Leu | Ala | Glu | Asn | Ile | Gln | Arg | Phe | Leu | Pro |
| | 210 | | | | | 215 | | | | | 220 | | | | |
| Asn | Pro | Asp | Gly | Leu | Gln | Pro | Gln | Asp | Pro | Glu | Phe | Gln | Ala | Ser | Asn |
| 225 | | | | | 230 | | | | | 235 | | | | | 240 |
| Ile | Met | His | Ser | Ile | Asn | Gly | Tyr | Val | Phe | Asp | Ser | Leu | Gln | Leu | Ser |
| | | | | 245 | | | | | 250 | | | | | 255 | |
| Val | Cys | Leu | His | Glu | Val | Ala | Tyr | Trp | Tyr | Ile | Leu | Ser | Val | Gly | Ala |
| | | | 260 | | | | | 265 | | | | | 270 | | |
| Gln | Thr | Asp | Phe | Leu | Ser | Val | Phe | Phe | Ser | Gly | Tyr | Thr | Phe | Lys | His |
| | | 275 | | | | | 280 | | | | | 285 | | | |
| Lys | Met | Val | Tyr | Glu | Asp | Thr | Leu | Thr | Leu | Phe | Pro | Phe | Ser | Gly | Glu |
| | 290 | | | | | 295 | | | | | 300 | | | | |
| Thr | Val | Phe | Met | Ser | Met | Glu | Asn | Pro | Gly | Leu | Trp | Val | Leu | Gly | Cys |
| 305 | | | | | 310 | | | | | 315 | | | | | 320 |
| His | Asn | Ser | Asp | Leu | Arg | Asn | Arg | Gly | Met | Thr | Ala | Leu | Leu | Lys | Val |
| | | | | 325 | | | | | 330 | | | | | 335 | |
| Tyr | Ser | Cys | Asp | Arg | Asp | Ile | Gly | Asp | Tyr | Tyr | Asp | Asn | Thr | Tyr | Glu |
| | | | 340 | | | | | 345 | | | | | 350 | | |
| Asp | Ile | Pro | Gly | Phe | Leu | Leu | Ser | Gly | Lys | Asn | Val | Ile | Glu | Pro | Arg |
| | | 355 | | | | | 360 | | | | | 365 | | | |

( 2 ) INFORMATION FOR SEQ ID NO:5:

( i ) SEQUENCE CHARACTERISTICS:

(A) LENGTH: 7493 base pairs
(B) TYPE: nucleic acid
(C) STRANDEDNESS: double
(D) TOPOLOGY: Not Relevant (ii) MOLECULE TYPE: cDNA to mRNA (iii) HYPOTHETICAL: NO (iv) ANTI-SENSE: NO (vi) ORIGINAL SOURCE:
(A) ORGANISM: Mus musculus (ix) FEATURE:
(A) NAME/KEY: repeat_unit
(B) LOCATION: 1..407
(D) OTHER INFORMATION: /rpt_type="terminal"
/ note= "5'UTR"

(ix) FEATURE:
(A) NAME/KEY: misc_feature
(B) LOCATION: 7471..7476
(D) OTHER INFORMATION: /function="polyA signal"

(ix) FEATURE:
(A) NAME/KEY: repeat_unit
(B) LOCATION: 7368..7493
(D) OTHER INFORMATION: /rpt_type="terminal"
/ note= "3'UTR"

(ix) FEATURE:
(A) NAME/KEY: misc_feature
(B) LOCATION: 408..7367
(D) OTHER INFORMATION: /product="coagulation factor VIII"

(x) PUBLICATION INFORMATION:
(A) AUTHORS: Elder, F.
Lakich, D.
Gitschier, J.
(B) TITLE: Sequence of the murine Factor VIII cDNA
(C) JOURNAL: Genomics
(D) VOLUME: 16
(F) PAGES: 374-379
(G) DATE: 1993

(xi) SEQUENCE DESCRIPTION: SEQ ID NO:5:

| | | | | | | |
|---|---|---|---|---|---|---|
| TCTAGAGTTT | CTTTGCTACA | GGTACCAAGG | AACAGTCTTT | TAGAATAGGC | TAGGAATTTA | 60 |
| AATACACCTG | AACGCCCCTC | CTCAGTATTC | TGTTCCTTTT | CTTAAGGATT | CAAACTTGTT | 120 |
| AGGATGCACC | CAGCAGGAAA | TGGGTTAAGC | CTTAGCTCAG | CCACTCTTCC | TATTCCAGTT | 180 |
| TTCCTGTGCC | TGCTTCCTAC | TACCCAAAAG | GAAGTAATCC | TTCAGATCTG | TTTTGTGCTA | 240 |
| ATGCTACTTT | CACTCACAGT | AGATAAACTT | CCAGAAAATC | CTCTGCAAAA | TATTTAGGAC | 300 |
| TTTTTACTAA | ATCATTACAT | TTCTTTTGT | TCTTAAAAGC | TAAAGTTATT | TTAGAGAAGA | 360 |
| GTTAAATTTT | CATTTCTTTA | GTTGAACATT | TTCTAGTAAT | AAAAGCCATG | CAAATAGCAC | 420 |
| TCTTCGCTTG | CTTCTTTCTG | AGCCTTTTCA | ATTTCTGCTC | TAGTGCCATC | AGAAGATACT | 480 |
| ACCTTGGTGC | AGTGGAATTG | TCCTGGAACT | ATATTCAGAG | TGATCTGCTC | AGTGTGCTGC | 540 |
| ATACAGACTC | AAGATTTCTT | CCTAGAATGT | CAACATCTTT | TCCATTCAAC | ACCTCCATCA | 600 |
| TGTATAAAAA | GACTGTGTTT | GTAGAGTACA | AGGACCAGCT | TTTCAACATT | GCCAAGCCCA | 660 |
| GGCCACCCTG | GATGGGTTTG | CTAGGTCCTA | CCATTTGGAC | TGAGGTTCAT | GACACAGTGG | 720 |
| TCATTACACT | TAAAAACATG | GCTTCTCATC | CTGTCAGTCT | TCATGCTGTT | GGTGTGTCCT | 780 |
| ACTGGAAAGC | TTCTGAGGGA | GATGAATATG | AAGATCAGAC | AAGCCAAATG | GAGAAGGAAG | 840 |
| ATGATAAAGT | TTTCCCTGGT | GAAAGTCATA | CTTATGTTTG | GCAAGTCCTG | AAAGAGAATG | 900 |
| GTCCAATGGC | CTCTGACCCT | CCATGTCTCA | CTTACTCATA | TATGTCTCAT | GTGGATCTGG | 960 |

-continued

| | | | | | | |
|---|---|---|---|---|---|---|
| TGAAAGATTT | GAATTCAGGC | CTCATTGGAG | CTCTGCTAGT | ATGTAAAGAA | GGCAGTCTCT | 1020 |
| CCAAAGAAAG | AACACAGATG | TTGTACCAAT | TTGTACTGCT | TTTTGCTGTA | TTTGATGAAG | 1080 |
| GGAAGAGCTG | GCACTCAGAA | ACAAACGACT | CTTATACACA | GTCTATGGAT | TCTGCATCTG | 1140 |
| CTAGAGACTG | GCCTAAAATG | CACACAGTCA | ATGGCTATGT | AAACAGGTCT | CTTCCAGGTC | 1200 |
| TGATTGGATG | CCATAGGAAA | TCAGTCTACT | GGCACGTGAT | TGGAATGGGC | ACCACTCCTG | 1260 |
| AAATACACTC | AATATTCCTC | GAAGGTCACA | CATTTTTGT | GAGGAACCAC | CGTCAAGCTT | 1320 |
| CATTGGAGAT | ATCACCAATA | ACTTTCCTTA | CTGCTCAAAC | ACTCTTGATA | GATCTTGGGC | 1380 |
| AGTTCCTACT | ATTTTGTCAT | ATCTCTTCCC | ATAAACATGA | TGGCATGGAA | GCTTATGTCA | 1440 |
| AAGTAGATAG | CTGCCCTGAG | GAATCCCAAT | GGCAAAAGAA | AATAATAAT | GAGGAAATGG | 1500 |
| AAGATTATGA | TGATGATCTT | TATTCAGAAA | TGGATATGTT | CACATTGGAT | TATGACAGCT | 1560 |
| CTCCTTTTAT | CCAAATTCGC | TCGGTTGCTA | AAAAGTACCC | TAAAACTTGG | ATACATTATA | 1620 |
| TTTCTGCTGA | GGAGGAAGAC | TGGGACTATG | CACCTTCAGT | TCCTACCTCG | GATAATGGAA | 1680 |
| GTTATAAAAG | CCAGTATCTG | AGCAATGGTC | CTCATCGGAT | TGGTAGGAAA | TATAAAAAAG | 1740 |
| TCAGATTTAT | AGCATACACA | GATGAAACCT | TTAAGACTCG | TGAAACTATT | CAGCATGAAT | 1800 |
| CAGGACTCTT | GGGACCTTTA | CTTTATGGAG | AAGTTGGAGA | CACACTGTTG | ATTATTTTTA | 1860 |
| AGAATCAAGC | AAGCCGACCA | TATAACATTT | ACCCTCATGG | AATCACTGAT | GTCAGTCCTC | 1920 |
| TACATGCAAG | GAGATTGCCA | AGAGGTATAA | AGCACGTGAA | GGATTTGCCA | ATTCATCCAG | 1980 |
| GAGAGATATT | CAAGTACAAG | TGGACAGTTA | CAGTAGAAGA | TGGACCAACT | AAATCAGATC | 2040 |
| CACGGTGCCT | GACCCGCTAT | TATTCAAGTT | TCATTAACCC | TGAGAGAGAT | CTAGCTTCAG | 2100 |
| GACTGATTGG | CCCTCTTCTC | ATCTGCTACA | AAGAATCTGT | AGATCAAAGG | GGAAACCAGA | 2160 |
| TGATGTCAGA | CAAAAGAAAT | GTCATCCTGT | TTTCTATATT | TGATGAGAAC | CAAAGCTGGT | 2220 |
| ACATCACAGA | GAACATGCAA | CGCTTCCTCC | CCAATGCAGC | TAAAACACAG | CCCCAGGACC | 2280 |
| CTGGGTTCCA | GGCCTCCAAC | ATCATGCACA | GCATCAATGG | CTATGTTTTT | GATAGCTTGG | 2340 |
| AGTTGACAGT | TTGTTTGCAT | GAGGTGGCAT | ACTGGCACAT | TCTCAGTGTT | GGAGCACAGA | 2400 |
| CAGACTTCTT | ATCTATCTTC | TTCTCTGGAT | ATACTTTCAA | ACACAAAATG | GTCTATGAAG | 2460 |
| ATACACTTAC | CCTGTTCCCA | TTCTCAGGAG | AAACTGTCTT | TATGTCGATG | GAAAACCCAG | 2520 |
| GTCTATGGGT | CTTGGGGTGT | CATAATTCAG | ACTTTCGGAA | GAGAGGTATG | ACAGCATTGC | 2580 |
| TGAAAGTTTC | TAGTTGTGAC | AAGAGCACTA | GTGATTATTA | TGAAGAAATA | TATGAAGATA | 2640 |
| TTCCAACACA | GTTGGTGAAT | GAGAACAATG | TCATTGATCC | CAGAAGCTTC | TTCCAGAATA | 2700 |
| CAAATCATCC | TAATACTAGG | AAAAAGAAAT | TCAAAGATTC | CACAATTCCA | AAAAATGATA | 2760 |
| TGGAGAAGAT | TGAGCCTCAG | TTTGAAGAGA | TAGCAGAGAT | GCTTAAAGTA | CAGAGTGTCT | 2820 |
| CAGTTAGTGA | CATGTTGATG | CTCTTGGGAC | AGAGTCATCC | TACTCCACAT | GGCTTATTTT | 2880 |
| TATCAGATGG | CCAAGAAGCC | ATCTATGAGG | CTATTCATGA | TGATCATTCA | CCAAATGCAA | 2940 |
| TAGACAGCAA | TGAAGGCCCA | TCTAAAGTGA | CCCAACTCAG | GCCAGAATCC | CATCACAGTG | 3000 |
| AGAAAATAGT | ATTTACTCCT | CAGCCCGGCC | TCCAGTTAAG | ATCCAATAAA | AGTTTGGAGA | 3060 |
| CAACTATAGA | AGTAAAGTGG | AAGAAACTTG | GTTTGCAAGT | TTCTAGTTTG | CCAAGTAATC | 3120 |
| TAATGACTAC | AACAATTCTG | TCAGACAATT | TGAAAGCAAC | TTTTGAAAAG | ACAGATTCTT | 3180 |
| CAGGATTTCC | AGATATGCCA | GTTCACTCTA | GTAGTAAATT | AAGTACTACT | GCATTTGGTA | 3240 |
| AGAAAGCATA | TTCCCTTGTT | GGGTCTCATG | TACCTTTAAA | CGCGAGTGAA | GAAAATAGTG | 3300 |
| ATTCCAACAT | ATTGGATTCA | ACTTTAATGT | ATAGTCAAGA | AAGTTTACCA | AGAGATAATA | 3360 |

-continued

| | | | | | | |
|---|---|---|---|---|---|---|
|TATTATCAAT|AGAGAATGAT|AGATTACTCA|GAGAGAAGAG|GTTTCATGGA|ATTGCTTTAT|3420|
|TGACCAAAGA|TAATACTTTA|TTCAAAGACA|ATGTCTCCTT|AATGAAAACA|AACAAAACAT|3480|
|ATAATCATTC|AACAACTAAT|GAAAAACTAC|ACACTGAGAG|CCCAACATCA|ATTGAGAATA|3540|
|GTACAACAGA|CTTGCAAGAT|GCCATATTAA|AGGTCAATAG|TGAGATTCAA|GAAGTAACAG|3600|
|CTTTGATTCA|TGATGGAACA|CTTTTAGGCA|AAAATTCTAC|ATATTTGAGA|CTAAACCATA|3660|
|TGCTAAATAG|AACTACCTCA|ACAAAAAATA|AAGACATATT|TCATAGAAAA|GATGAAGATC|3720|
|CTATTCCACA|AGATGAAGAG|AATACAATCA|TGCCATTTTC|CAAGATGTTG|TTCTTGTCAG|3780|
|AATCTTCAAA|TTGGTTTAAA|AAGACCAATG|GAAATAATTC|CTTGAACTCT|GAGCAAGAAC|3840|
|ATAGTCCAAA|GCAATTAGTA|TATTTAATGT|TTAAAAAATA|TGTAAAAAAT|CAAAGTTTCT|3900|
|TGTCAGAGAA|AAATAAAGTC|ACAGTAGAAC|AGGATGGATT|TACAAAGAAC|ATAGGACTTA|3960|
|AAGACATGGC|TTTTCCACAT|AATATGAGCA|TATTTCTTAC|CACTTTGTCT|AACGTACATG|4020|
|AAAATGGTAG|GCACAATCAA|GAAAAAAATA|TTCAGGAAGA|GATAGAGAAG|GAAGCACTAA|4080|
|TTGAAGAGAA|AGTAGTTTTG|CCCCAGGTGC|ACGAAGCAAC|TGGCTCTAAG|AATTTCTTGA|4140|
|AAGACATATT|GATACTAGGC|ACTAGGCAAA|ATATAAGTTT|ATATGAAGTA|CATGTACCAG|4200|
|TACTTCAAAA|CATCACATCA|ATAAACAATT|CAACAAATAC|AGTACAGATT|CACATGGAGC|4260|
|ATTTCTTTAA|AAGAAGGAAG|GACAAGGAAA|CAAATTCAGA|AGGCTTGGTA|AATAAAACCA|4320|
|GAGAAATGGT|AAAAAACTAT|CCAAGCCAGA|AGAATATTAC|TACTCAACGT|AGTAAACGGG|4380|
|CTTTGGGACA|ATTCAGACTG|TCAACTCAAT|GGCTTAAAAC|CATAAACTGT|TCAACACAGT|4440|
|GTATCATTAA|ACAGATAGAC|CACAGCAAGG|AAATGAAAAA|GTTCATTACT|AAATCTTCCT|4500|
|TATCAGATTC|TTCTGTGATT|AAAAGCACCA|CTCAGACAAA|TAGTTCTGAC|TCACACATTG|4560|
|TAAAAACATC|AGCATTTCCA|CCAATAGATC|TCAAAGGAG|TCCATTCCAA|AACAAATTTT|4620|
|CTCATGTTCA|AGCATCATCC|TACATTTATG|ACTTTAAGAC|AAAAAGTTCA|AGAATTCAAG|4680|
|AAAGCAATAA|TTTCTTAAAA|GAAACCAAAA|TAAATAACCC|TTCTTTAGCC|ATTCTACCAT|4740|
|GGAATATGTT|CATAGATCAA|GGAAAATTTA|CCTCCCCAGG|GAAAAGTAAC|ACAAACTCAG|4800|
|TCACATATAA|GAAACGTGAG|AACATTATTT|TCTTGAAACC|AACTTTGCCT|GAAGAATCTG|4860|
|GCAAAATTGA|ATTGCTTCCT|CAAGTTTCCA|TTCAAGAGGA|AGAAATTTTA|CCTACAGAAA|4920|
|CTAGCCATGG|ATCTCCTGGA|CACTTGAATC|TCATGAAAGA|GGTCTTTCTT|CAGAAAATAC|4980|
|AGGGGCCTAC|TAAATGGAAT|AAAGCAAAGA|GGCATGGAGA|AAGTATAAAA|GGTAAAACAG|5040|
|AGAGCTCTAA|AAATACTCGC|TCAAAACTGC|TAAATCATCA|TGCTTGGGAT|TATCATTATG|5100|
|CTGCACAGAT|ACCAAAAGAT|ATGTGGAAAT|CCAAGAGAA|GTCACCAGAA|ATTATATCCA|5160|
|TTAAGCAAGA|GGACACCATT|TTGTCTCTGA|GGCCTCATGG|AAACAGTCAT|TCAATAGGGG|5220|
|CAAATGAGAA|ACAAATTGG|CCTCAAAGAG|AAACCACTTG|GGTAAAGCAA|GGCCAAACTC|5280|
|AAAGGACATG|CTCTCAAATC|CCACCAGTGT|TGAAACGACA|TCAAAGGGAA|CTTAGTGCTT|5340|
|TTCAATCAGA|ACAAGAAGCA|ACTGACTATG|ATGATGCCAT|CACCATTGAA|ACAATCGAGG|5400|
|ATTTTGACAT|TTACAGTGAG|GACATAAAGC|AAGGTCCCCG|CAGCTTTCAA|CAGAAAACAA|5460|
|GGCACTATTT|TATTGCAGCT|GTGGAACGAC|TCTGGGACTA|TGGGATGAGT|ACATCTCATG|5520|
|TTCTACGAAA|TAGGTATCAA|AGTGACAATG|TACCTCAGTT|CAAGAAAGTA|GTTTTCCAGG|5580|
|AATTTACTGA|TGGCTCCTTT|AGTCAGCCCT|TATATCGTGG|AGAATTAAAT|GAACACCTGG|5640|
|GGTTGTTGGG|CCCATATATA|AGAGCAGAAG|TTGAAGACAA|CATTATGGTA|ACTTTCAAAA|5700|
|ACCAGGCCTC|CCGTCCCTAC|TCCTTCTATT|CTAGCCTCAT|TTCTTATAAA|GAAGATCAGA|5760|

| | | | | | | |
|---|---|---|---|---|---|---|
|GAGGAGAAGA|ACCTAGAAGA|AACTTTGTCA|AGCCTAATGA|AACCAAAATT|TATTTTTGGA|5820|
|AAGTACAACA|TCATATGGCA|CCCACAGAAG|ATGAGTTTGA|CTGCAAGGCC|TGGGCTTATT|5880|
|TCTCTGATGT|TGATCTTGAA|AGAGATATGC|ACTCGGGATT|AATTGGACCC|CTTCTGATTT|5940|
|GCCACGCGAA|CACACTGAAT|CCTGCTCATG|GGAGACAAGT|GTCAGTACAG|GAATTTGCTC|6000|
|TGCTTTTCAC|TATCTTTGAT|GAGACCAAGA|GCTGGTACTT|CACTGAAAAC|GTGAAAAGGA|6060|
|ACTGCAAGAC|ACCCTGCAAT|TTCCAGATGG|AAGACCCCAC|TTTGAAAGAG|AATTATCGCT|6120|
|TCCATGCAAT|CAATGGTTAT|GTAATGGATA|CCCTACCAGG|CTTAGTAATG|GCTCAAGATC|6180|
|AAAGGATTCG|ATGGTATCTT|CTCAGCATGG|GCAACAATGA|GAACATCCAA|TCTATTCATT|6240|
|TCAGTGGACA|TGTTTTCACT|GTACGGAAAA|AAGAGGAGTA|TAAAATGGCA|GTGTACAACC|6300|
|TCTACCCAGG|TGTTTTTGAG|ACTCTGGAAA|TGATACCATC|CAGAGCTGGA|ATATGGCGAG|6360|
|TAGAATGCCT|TATTGGCGAG|CACTTACAGG|CTGGGATGAG|CACTCTTTTT|CTGGTGTACA|6420|
|GCAAGCAGTG|TCAGATTCCT|CTTGGAATGG|CTTCTGGAAG|CATCCGTGAT|TTCCAGATTA|6480|
|CAGCTTCAGG|ACATTATGGA|CAGTGGGCCC|CAAACCTGGC|AAGACTTCAT|TATTCCGGAT|6540|
|CAATCAATGC|CTGGAGTACC|AAGGAGCCCT|TTTCTTGGAT|CAAGGTAGAT|CTGTTGGCAC|6600|
|CAATGATTGT|TCATGGCATC|AAGACTCAGG|GTGCTCGTCA|GAAATTTTCC|AGCCTTTATA|6660|
|TCTCTCAATT|TATCATCATG|TATAGCCTGG|ATGGGAAGAA|GTGGCTGAGT|TATCAAGGAA|6720|
|ATTCCACTGG|AACCTTAATG|GTTTTCTTTG|GCAATGTGGA|CTCATCTGGG|ATTAAGCATA|6780|
|ATAGTTTTAA|TCCTCCAATT|ATTGCTCGAT|ATATCCGTTT|GCACCCCACT|CATTCTAGCA|6840|
|TCCGTAGTAC|TCTTCGCATG|GAGTTGATGG|GCTGTGATTT|AAACAGTTGC|AGCATACCAT|6900|
|TGGGAATGGA|AAGTAAAGTA|ATATCAGATA|CACAAATCAC|TGCCTCATCC|TACTTCACCA|6960|
|ACATGTTTGC|TACTTGGTCT|CCTTCACAAG|CTCGACTTCA|CCTCCAGGGA|AGGACTAATG|7020|
|CCTGGCGACC|TCAGGTGAAT|GATCCAAAAC|AATGGTTGCA|AGTGGACTTA|CAAAAGACAA|7080|
|TGAAAGTCAC|TGGAATAATA|ACCCAGGGAG|TGAAATCTCT|CTTTACCAGC|ATGTTTGTGA|7140|
|AAGAGTTCCT|TATTTCCAGC|AGTCAAGATG|GCCATCACTG|GACTCAAATT|TTATACAATG|7200|
|GCAAGGTAAA|GGTTTTTCAG|GGGAATCAGG|ACTCATCCAC|ACCTATGATG|AATTCTCTAG|7260|
|ACCCACCATT|ACTCACTCGC|TATCTTCGAA|TTCACCCCCA|GATCTGGGAG|CACCAAATTG|7320|
|CTCTGAGGCT|TGAGATTCTA|GGATGTGAGG|CCCAGCAGCA|ATACTGAGGT|AGCCTCTGCA|7380|
|TCACCTGCTT|ATTCCCCTTC|CTCAGCTCAA|AGATTGTCTT|AATGTTTTAT|TGCTGTGAAG|7440|
|AGACACTATG|ACCATGGCAA|CTCTTTATAA|AATAAAGCAT|TTAATCAGGG|CTT|7493|

( 2 ) INFORMATION FOR SEQ ID NO:6:

( i ) SEQUENCE CHARACTERISTICS:
        ( A ) LENGTH: 2319 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Mus musculus ( x ) PUBLICATION INFORMATION:
        ( A ) AUTHORS: Elder, F.

Lakich, D.
Gitschier, J.
(B) TITLE: Sequence of the Murine Factor VIII cDNA
(C) JOURNAL: Genomics
(D) VOLUME: 16
(F) PAGES: 374-379
(G) DATE: 1993
(K) RELEVANT RESIDUES IN SEQ ID NO:6: FROM 1 TO 2319

(xi) SEQUENCE DESCRIPTION: SEQ ID NO:6:

```
Met Gln Ile Ala Leu Phe Ala Cys Phe Phe Leu Ser Leu Phe Asn Phe
 1               5                  10                  15
Cys Ser Ser Ala Ile Arg Arg Tyr Tyr Leu Gly Ala Val Glu Leu Ser
            20                  25                  30
Trp Asn Tyr Ile Gln Ser Asp Leu Leu Ser Val Leu His Thr Asp Ser
        35                  40                  45
Arg Phe Leu Pro Arg Met Ser Thr Ser Phe Pro Phe Asn Thr Ser Ile
    50                  55                  60
Met Tyr Lys Lys Thr Val Phe Val Glu Tyr Lys Asp Gln Leu Phe Asn
65                  70                  75                  80
Ile Ala Lys Pro Arg Pro Pro Trp Met Gly Leu Leu Gly Pro Thr Ile
                85                  90                  95
Trp Thr Glu Val His Asp Thr Val Val Ile Thr Leu Lys Asn Met Ala
            100                 105                 110
Ser His Pro Val Ser Leu His Ala Val Gly Val Ser Tyr Trp Lys Ala
            115                 120                 125
Ser Glu Gly Asp Glu Tyr Glu Asp Gln Thr Ser Gln Met Glu Lys Glu
    130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                165                 170                 175
Ser Tyr Met Ser His Val Asp Leu Val Lys Asp Leu Asn Ser Gly Leu
            180                 185                 190
Ile Gly Ala Leu Leu Val Cys Lys Glu Gly Ser Leu Ser Lys Glu Arg
        195                 200                 205
Thr Gln Met Leu Tyr Gln Phe Val Leu Leu Phe Ala Val Phe Asp Glu
    210                 215                 220
Gly Lys Ser Trp His Ser Glu Thr Asn Asp Ser Tyr Thr Gln Ser Met
225                 230                 235                 240
Asp Ser Ala Ser Ala Arg Asp Trp Pro Lys Met His Thr Val Asn Gly
                245                 250                 255
Tyr Val Asn Arg Ser Leu Pro Gly Leu Ile Gly Cys His Arg Lys Ser
            260                 265                 270
Val Tyr Trp His Val Ile Gly Met Gly Thr Thr Pro Glu Ile His Ser
            275                 280                 285
Ile Phe Leu Glu Gly His Thr Phe Phe Val Arg Asn His Arg Gln Ala
    290                 295                 300
Ser Leu Glu Ile Ser Pro Ile Thr Phe Leu Thr Ala Gln Thr Leu Leu
305                 310                 315                 320
Ile Asp Leu Gly Gln Phe Leu Leu Phe Cys His Ile Ser Ser His Lys
                325                 330                 335
His Asp Gly Met Glu Ala Tyr Val Lys Val Asp Ser Cys Pro Glu Glu
            340                 345                 350
Ser Gln Trp Gln Lys Lys Asn Asn Asn Glu Glu Met Glu Asp Tyr Asp
    355                 360                 365
```

```
Asp  Asp  Leu  Tyr  Ser  Glu  Met  Asp  Met  Phe  Thr  Leu  Asp  Tyr  Asp  Ser
     370                 375                 380

Ser  Pro  Phe  Ile  Gln  Ile  Arg  Ser  Val  Ala  Lys  Lys  Tyr  Pro  Lys  Thr
385                      390                 395                           400

Trp  Ile  His  Tyr  Ile  Ser  Ala  Glu  Glu  Asp  Trp  Asp  Tyr  Ala  Pro
                    405                      410                      415

Ser  Val  Pro  Thr  Ser  Asp  Asn  Gly  Ser  Tyr  Lys  Ser  Gln  Tyr  Leu  Ser
               420                      425                 430

Asn  Gly  Pro  His  Arg  Ile  Gly  Arg  Lys  Tyr  Lys  Lys  Val  Arg  Phe  Ile
               435                 440                      445

Ala  Tyr  Thr  Asp  Glu  Thr  Phe  Lys  Thr  Arg  Glu  Thr  Ile  Gln  His  Glu
     450                      455                      460

Ser  Gly  Leu  Leu  Gly  Pro  Leu  Leu  Tyr  Gly  Glu  Val  Gly  Asp  Thr  Leu
465                      470                      475                      480

Leu  Ile  Ile  Phe  Lys  Asn  Gln  Ala  Ser  Arg  Pro  Tyr  Asn  Ile  Tyr  Pro
                    485                      490                      495

His  Gly  Ile  Thr  Asp  Val  Ser  Pro  Leu  His  Ala  Arg  Arg  Leu  Pro  Arg
               500                 505                      510

Gly  Ile  Lys  His  Val  Lys  Asp  Leu  Pro  Ile  His  Pro  Gly  Glu  Ile  Phe
          515                 520                      525

Lys  Tyr  Lys  Trp  Thr  Val  Thr  Val  Glu  Asp  Gly  Pro  Thr  Lys  Ser  Asp
     530                 535                      540

Pro  Arg  Cys  Leu  Thr  Arg  Tyr  Tyr  Ser  Ser  Phe  Ile  Asn  Pro  Glu  Arg
545                 550                 555                           560

Asp  Leu  Ala  Ser  Gly  Leu  Ile  Gly  Pro  Leu  Leu  Ile  Cys  Tyr  Lys  Glu
               565                      570                      575

Ser  Val  Asp  Gln  Arg  Gly  Asn  Gln  Met  Met  Ser  Asp  Lys  Arg  Asn  Val
               580                 585                 590

Ile  Leu  Phe  Ser  Ile  Phe  Asp  Glu  Asn  Gln  Ser  Trp  Tyr  Ile  Thr  Glu
          595                      600                 605

Asn  Met  Gln  Arg  Phe  Leu  Pro  Asn  Ala  Ala  Lys  Thr  Gln  Pro  Gln  Asp
     610                      615                 620

Pro  Gly  Phe  Gln  Ala  Ser  Asn  Ile  Met  His  Ser  Ile  Asn  Gly  Tyr  Val
625                      630                 635                           640

Phe  Asp  Ser  Leu  Glu  Leu  Thr  Val  Cys  Leu  His  Glu  Val  Ala  Tyr  Trp
               645                 650                      655

His  Ile  Leu  Ser  Val  Gly  Ala  Gln  Thr  Asp  Phe  Leu  Ser  Ile  Phe  Phe
               660                 665                      670

Ser  Gly  Tyr  Thr  Phe  Lys  His  Lys  Met  Val  Tyr  Glu  Asp  Thr  Leu  Thr
          675                 680                 685

Leu  Phe  Pro  Phe  Ser  Gly  Glu  Thr  Val  Phe  Met  Ser  Met  Glu  Asn  Pro
     690                 695                 700

Gly  Leu  Trp  Val  Leu  Gly  Cys  His  Asn  Ser  Asp  Phe  Arg  Lys  Arg  Gly
705                      710                 715                           720

Met  Thr  Ala  Leu  Leu  Lys  Val  Ser  Ser  Cys  Asp  Lys  Ser  Thr  Ser  Asp
                    725                 730                      735

Tyr  Tyr  Glu  Glu  Ile  Tyr  Glu  Asp  Ile  Pro  Thr  Gln  Leu  Val  Asn  Glu
               740                 745                      750

Asn  Asn  Val  Ile  Asp  Pro  Arg  Ser  Phe  Phe  Gln  Asn  Thr  Asn  His  Pro
               755                 760                      765

Asn  Thr  Arg  Lys  Lys  Lys  Phe  Lys  Asp  Ser  Thr  Ile  Pro  Lys  Asn  Asp
     770                      775                 780

Met  Glu  Lys  Ile  Glu  Pro  Gln  Phe  Glu  Glu  Ile  Ala  Glu  Met  Leu  Lys
785                      790                 795                           800
```

-continued

| | | | | | | | | | | | | | | |
|---|---|---|---|---|---|---|---|---|---|---|---|---|---|---|
|Val|Gln|Ser|Val|Ser|Val|Ser|Asp|Met|Leu|Met|Leu|Leu|Gly|Gln|Ser|
| | | | |805| | | |810| | | | |815| |
|His|Pro|Thr|Pro|His|Gly|Leu|Phe|Leu|Ser|Asp|Gly|Gln|Glu|Ala|Ile|
| | | |820| | | |825| | | | |830| | |
|Tyr|Glu|Ala|Ile|His|Asp|Asp|His|Ser|Pro|Asn|Ala|Ile|Asp|Ser|Asn|
| | |835| | | |840| | | |845| | | | |
|Glu|Gly|Pro|Ser|Lys|Val|Thr|Gln|Leu|Arg|Pro|Glu|Ser|His|His|Ser|
| |850| | | |855| | | |860| | | | | | |
|Glu|Lys|Ile|Val|Phe|Thr|Pro|Gln|Pro|Gly|Leu|Gln|Leu|Arg|Ser|Asn|
|865| | | | |870| | | |875| | | | |880| |
|Lys|Ser|Leu|Glu|Thr|Thr|Ile|Glu|Val|Lys|Trp|Lys|Lys|Leu|Gly|Leu|
| | | | |885| | | |890| | | | |895| | |
|Gln|Val|Ser|Ser|Leu|Pro|Ser|Asn|Leu|Met|Thr|Thr|Thr|Ile|Leu|Ser|
| | | |900| | | |905| | | | |910| | | |
|Asp|Asn|Leu|Lys|Ala|Thr|Phe|Glu|Lys|Thr|Asp|Ser|Ser|Gly|Phe|Pro|
| | |915| | | |920| | | | |925| | | | |
|Asp|Met|Pro|Val|His|Ser|Ser|Ser|Lys|Leu|Ser|Thr|Thr|Ala|Phe|Gly|
| |930| | | | |935| | | | |940| | | | |
|Lys|Lys|Ala|Tyr|Ser|Leu|Val|Gly|Ser|His|Val|Pro|Leu|Asn|Ala|Ser|
|945| | | |950| | | |955| | | | | |960| |
|Glu|Glu|Asn|Ser|Asp|Ser|Asn|Ile|Leu|Asp|Ser|Thr|Leu|Met|Tyr|Ser|
| | | | |965| | | |970| | | | |975| | |
|Gln|Glu|Ser|Leu|Pro|Arg|Asp|Asn|Ile|Leu|Ser|Ile|Glu|Asn|Asp|Arg|
| | | |980| | | |985| | | | |990| | | |
|Leu|Leu|Arg|Glu|Lys|Arg|Phe|His|Gly|Ile|Ala|Leu|Leu|Thr|Lys|Asp|
| | |995| | | |1000| | | | |1005| | | | |
|Asn|Thr|Leu|Phe|Lys|Asp|Asn|Val|Ser|Leu|Met|Lys|Thr|Asn|Lys|Thr|
| |1010| | | |1015| | | | |1020| | | | | |
|Tyr|Asn|His|Ser|Thr|Thr|Asn|Glu|Lys|Leu|His|Thr|Glu|Ser|Pro|Thr|
|1025| | | |1030| | | |1035| | | | |1040| | |
|Ser|Ile|Glu|Asn|Ser|Thr|Thr|Asp|Leu|Gln|Asp|Ala|Ile|Leu|Lys|Val|
| | | | |1045| | | |1050| | | | |1055| | |
|Asn|Ser|Glu|Ile|Gln|Glu|Val|Thr|Ala|Leu|Ile|His|Asp|Gly|Thr|Leu|
| | | |1060| | | |1065| | | | |1070| | | |
|Leu|Gly|Lys|Asn|Ser|Thr|Tyr|Leu|Arg|Leu|Asn|His|Met|Leu|Asn|Arg|
| | |1075| | | |1080| | | | |1085| | | | |
|Thr|Thr|Ser|Thr|Lys|Asn|Lys|Asp|Ile|Phe|His|Arg|Lys|Asp|Glu|Asp|
| | |1090| | | |1095| | | | |1100| | | | |
|Pro|Ile|Pro|Gln|Asp|Glu|Glu|Asn|Thr|Ile|Met|Pro|Phe|Ser|Lys|Met|
|1105| | | | |1110| | | |1115| | | | | |1120|
|Leu|Phe|Leu|Ser|Glu|Ser|Ser|Asn|Trp|Phe|Lys|Lys|Thr|Asn|Gly|Asn|
| | | | |1125| | | |1130| | | | |1135| | |
|Asn|Ser|Leu|Asn|Ser|Glu|Gln|Glu|His|Ser|Pro|Lys|Gln|Leu|Val|Tyr|
| | | |1140| | | |1145| | | | |1150| | | |
|Leu|Met|Phe|Lys|Lys|Tyr|Val|Lys|Asn|Gln|Ser|Phe|Leu|Ser|Glu|Lys|
| | | |1155| | | |1160| | | | |1165| | | |
|Asn|Lys|Val|Thr|Val|Glu|Gln|Asp|Gly|Phe|Thr|Lys|Asn|Ile|Gly|Leu|
| | |1170| | | |1175| | | | |1180| | | | |
|Lys|Asp|Met|Ala|Phe|Pro|His|Asn|Met|Ser|Ile|Phe|Leu|Thr|Thr|Leu|
|1185| | | | |1190| | | |1195| | | | | |1200|
|Ser|Asn|Val|His|Glu|Asn|Gly|Arg|His|Asn|Gln|Glu|Lys|Asn|Ile|Gln|
| | | | |1205| | | |1210| | | | |1215| | |
|Glu|Glu|Ile|Glu|Lys|Glu|Ala|Leu|Ile|Glu|Glu|Lys|Val|Val|Leu|Pro|

```
                              1220                      1225                      1230
        Gln  Val  His  Glu  Ala  Thr  Gly  Ser  Lys  Asn  Phe  Leu  Lys  Asp  Ile  Leu
                         1235                      1240                      1245
        Ile  Leu  Gly  Thr  Arg  Gln  Asn  Ile  Ser  Leu  Tyr  Glu  Val  His  Val  Pro
                         1250                      1255                      1260
        Val  Leu  Gln  Asn  Ile  Thr  Ser  Ile  Asn  Asn  Ser  Thr  Asn  Thr  Val  Gln
        1265                      1270                      1275                      1280
        Ile  His  Met  Glu  His  Phe  Phe  Lys  Arg  Arg  Lys  Asp  Lys  Glu  Thr  Asn
                         1285                      1290                      1295
        Ser  Glu  Gly  Leu  Val  Asn  Lys  Thr  Arg  Glu  Met  Val  Lys  Asn  Tyr  Pro
                         1300                      1305                      1310
        Ser  Gln  Lys  Asn  Ile  Thr  Thr  Gln  Arg  Ser  Lys  Arg  Ala  Leu  Gly  Gln
                         1315                      1320                      1325
        Phe  Arg  Leu  Ser  Thr  Gln  Trp  Leu  Lys  Thr  Ile  Asn  Cys  Ser  Thr  Gln
                         1330                      1335                      1340
        Cys  Ile  Ile  Lys  Gln  Ile  Asp  His  Ser  Lys  Glu  Met  Lys  Lys  Phe  Ile
        1345                      1350                      1355                      1360
        Thr  Lys  Ser  Ser  Leu  Ser  Asp  Ser  Ser  Val  Ile  Lys  Ser  Thr  Thr  Gln
                         1365                      1370                      1375
        Thr  Asn  Ser  Ser  Asp  Ser  His  Ile  Val  Lys  Thr  Ser  Ala  Phe  Pro  Pro
                         1380                      1385                      1390
        Ile  Asp  Leu  Lys  Arg  Ser  Pro  Phe  Gln  Asn  Lys  Phe  Ser  His  Val  Gln
                         1395                      1400                      1405
        Ala  Ser  Ser  Tyr  Ile  Tyr  Asp  Phe  Lys  Thr  Lys  Ser  Ser  Arg  Ile  Gln
                         1410                      1415                      1420
        Glu  Ser  Asn  Asn  Phe  Leu  Lys  Glu  Thr  Lys  Ile  Asn  Asn  Pro  Ser  Leu
        1425                      1430                      1435                      1440
        Ala  Ile  Leu  Pro  Trp  Asn  Met  Phe  Ile  Asp  Gln  Gly  Lys  Phe  Thr  Ser
                         1445                      1450                      1455
        Pro  Gly  Lys  Ser  Asn  Thr  Asn  Ser  Val  Thr  Tyr  Lys  Lys  Arg  Glu  Asn
                         1460                      1465                      1470
        Ile  Ile  Phe  Leu  Lys  Pro  Thr  Leu  Pro  Glu  Glu  Ser  Gly  Lys  Ile  Glu
                         1475                      1480                      1485
        Leu  Leu  Pro  Gln  Val  Ser  Ile  Gln  Glu  Glu  Glu  Ile  Leu  Pro  Thr  Glu
                         1490                      1495                      1500
        Thr  Ser  His  Gly  Ser  Pro  Gly  His  Leu  Asn  Leu  Met  Lys  Glu  Val  Phe
        1505                      1510                      1515                      1520
        Leu  Gln  Lys  Ile  Gln  Gly  Pro  Thr  Lys  Trp  Asn  Lys  Ala  Lys  Arg  His
                         1525                      1530                      1535
        Gly  Glu  Ser  Ile  Lys  Gly  Lys  Thr  Glu  Ser  Ser  Lys  Asn  Thr  Arg  Ser
                         1540                      1545                      1550
        Lys  Leu  Leu  Asn  His  His  Ala  Trp  Asp  Tyr  His  Tyr  Ala  Ala  Gln  Ile
                         1555                      1560                      1565
        Pro  Lys  Asp  Met  Trp  Lys  Ser  Lys  Glu  Lys  Ser  Pro  Glu  Ile  Ile  Ser
                         1570                      1575                      1580
        Ile  Lys  Gln  Glu  Asp  Thr  Ile  Leu  Ser  Leu  Arg  Pro  His  Gly  Asn  Ser
        1585                      1590                      1595                      1600
        His  Ser  Ile  Gly  Ala  Asn  Glu  Lys  Gln  Asn  Trp  Pro  Gln  Arg  Glu  Thr
                         1605                      1610                      1615
        Thr  Trp  Val  Lys  Gln  Gly  Gln  Thr  Gln  Arg  Thr  Cys  Ser  Gln  Ile  Pro
                         1620                      1625                      1630
        Pro  Val  Leu  Lys  Arg  His  Gln  Arg  Glu  Leu  Ser  Ala  Phe  Gln  Ser  Glu
                         1635                      1640                      1645
```

```
Gln Glu Ala Thr Asp Tyr Asp Asp Ala Ile Thr Ile Glu Thr Ile Glu
        1650                1655                1660
Asp Phe Asp Ile Tyr Ser Glu Asp Ile Lys Gln Gly Pro Arg Ser Phe
1665                1670                1675                1680
Gln Gln Lys Thr Arg His Tyr Phe Ile Ala Ala Val Glu Arg Leu Trp
                1685                1690                1695
Asp Tyr Gly Met Ser Thr Ser His Val Leu Arg Asn Arg Tyr Gln Ser
                    1700                1705                1710
Asp Asn Val Pro Gln Phe Lys Lys Val Val Phe Gln Glu Phe Thr Asp
                1715                1720                1725
Gly Ser Phe Ser Gln Pro Leu Tyr Arg Gly Glu Leu Asn Glu His Leu
            1730                1735                1740
Gly Leu Leu Gly Pro Tyr Ile Arg Ala Glu Val Glu Asp Asn Ile Met
1745                1750                1755                1760
Val Thr Phe Lys Asn Gln Ala Ser Arg Pro Tyr Ser Phe Tyr Ser Ser
                1765                1770                1775
Leu Ile Ser Tyr Lys Glu Asp Gln Arg Gly Glu Glu Pro Arg Arg Asn
                1780                1785                1790
Phe Val Lys Pro Asn Glu Thr Lys Ile Tyr Phe Trp Lys Val Gln His
            1795                1800                1805
His Met Ala Pro Thr Glu Asp Glu Phe Asp Cys Lys Ala Trp Ala Tyr
        1810                1815                1820
Phe Ser Asp Val Asp Leu Glu Arg Asp Met His Ser Gly Leu Ile Gly
1825                1830                1835                1840
Pro Leu Leu Ile Cys His Ala Asn Thr Leu Asn Pro Ala His Gly Arg
                1845                1850                1855
Gln Val Ser Val Gln Glu Phe Ala Leu Leu Phe Thr Ile Phe Asp Glu
            1860                1865                1870
Thr Lys Ser Trp Tyr Phe Thr Glu Asn Val Lys Arg Asn Cys Lys Thr
        1875                1880                1885
Pro Cys Asn Phe Gln Met Glu Asp Pro Thr Leu Lys Glu Asn Tyr Arg
    1890                1895                1900
Phe His Ala Ile Asn Gly Tyr Val Met Asp Thr Leu Pro Gly Leu Val
1905                1910                1915                1920
Met Ala Gln Asp Gln Arg Ile Arg Trp Tyr Leu Leu Ser Met Gly Asn
                1925                1930                1935
Asn Glu Asn Ile Gln Ser Ile His Phe Ser Gly His Val Phe Thr Val
                1940                1945                1950
Arg Lys Lys Glu Glu Tyr Lys Met Ala Val Tyr Asn Leu Tyr Pro Gly
            1955                1960                1965
Val Phe Glu Thr Leu Glu Met Ile Pro Ser Arg Ala Gly Ile Trp Arg
        1970                1975                1980
Val Glu Cys Leu Ile Gly Glu His Leu Gln Ala Gly Met Ser Thr Leu
1985                1990                1995                2000
Phe Leu Val Tyr Ser Lys Gln Cys Gln Ile Pro Leu Gly Met Ala Ser
                2005                2010                2015
Gly Ser Ile Arg Asp Phe Gln Ile Thr Ala Ser Gly His Tyr Gly Gln
                2020                2025                2030
Trp Ala Pro Asn Leu Ala Arg Leu His Tyr Ser Gly Ser Ile Asn Ala
            2035                2040                2045
Trp Ser Thr Lys Glu Pro Phe Ser Trp Ile Lys Val Asp Leu Leu Ala
            2050                2055                2060
Pro Met Ile Val His Gly Ile Lys Thr Gln Gly Ala Arg Gln Lys Phe
    2065                2070                2075                2080
```

Ser  Ser  Leu  Tyr  Ile  Ser  Gln  Phe  Ile  Ile  Met  Tyr  Ser  Leu  Asp  Gly
               2085               2090                    2095

Lys  Lys  Trp  Leu  Ser  Tyr  Gln  Gly  Asn  Ser  Thr  Gly  Thr  Leu  Met  Val
               2100                    2105                    2110

Phe  Phe  Gly  Asn  Val  Asp  Ser  Ser  Gly  Ile  Lys  His  Asn  Ser  Phe  Asn
               2115               2120                    2125

Pro  Pro  Ile  Ile  Ala  Arg  Tyr  Ile  Arg  Leu  His  Pro  Thr  His  Ser  Ser
          2130                    2135                    2140

Ile  Arg  Ser  Thr  Leu  Arg  Met  Glu  Leu  Met  Gly  Cys  Asp  Leu  Asn  Ser
2145                         2150                    2155                    2160

Cys  Ser  Ile  Pro  Leu  Gly  Met  Glu  Ser  Lys  Val  Ile  Ser  Asp  Thr  Gln
               2165                    2170                    2175

Ile  Thr  Ala  Ser  Ser  Tyr  Phe  Thr  Asn  Met  Phe  Ala  Thr  Trp  Ser  Pro
               2180                    2185                    2190

Ser  Gln  Ala  Arg  Leu  His  Leu  Gln  Gly  Arg  Thr  Asn  Ala  Trp  Arg  Pro
          2195                    2200                    2205

Gln  Val  Asn  Asp  Pro  Lys  Gln  Trp  Leu  Gln  Val  Asp  Leu  Gln  Lys  Thr
          2210                    2215                    2220

Met  Lys  Val  Thr  Gly  Ile  Ile  Thr  Gln  Gly  Val  Lys  Ser  Leu  Phe  Thr
2225                         2230                    2235                    2240

Ser  Met  Phe  Val  Lys  Glu  Phe  Leu  Ile  Ser  Ser  Ser  Gln  Asp  Gly  His
               2245                    2250                    2255

His  Trp  Thr  Gln  Ile  Leu  Tyr  Asn  Gly  Lys  Val  Lys  Val  Phe  Gln  Gly
          2260                    2265                    2270

Asn  Gln  Asp  Ser  Ser  Thr  Pro  Met  Met  Asn  Ser  Leu  Asp  Pro  Pro  Leu
          2275                    2280                    2285

Leu  Thr  Arg  Tyr  Leu  Arg  Ile  His  Pro  Gln  Ile  Trp  Glu  His  Gln  Ile
          2290                    2295                    2300

Ala  Leu  Arg  Leu  Glu  Ile  Leu  Gly  Cys  Glu  Ala  Gln  Gln  Gln  Tyr
2305                         2310                    2315

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:7:

CCTTCCTTTA  TCCAAATACG  TAGATCAAGA  GGAAATTGAC          40

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO (xi) SEQUENCE DESCRIPTION: SEQ ID NO:8:

GTAGCGTTGC CAAGAAGCAC CCTAAGACG 29

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

GAAGAGTAGT ACGAGTTATT TCTCTGGGTT CAATGAC 37

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

CCTTTATCCA AATACGTAGC GTTTGCCAAG AAG 33

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: misc_feature
        (B) LOCATION: 1..19
        (D) OTHER INFORMATION: /note= "R is A or G and N is A, T,
            G or C."

(xi) SEQUENCE DESCRIPTION: SEQ ID NO:11:

AARCAYCCNA ARACNTGGG 19

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO ( i v ) ANTI-SENSE: NO ( x i ) SEQUENCE DESCRIPTION: SEQ ID NO:12:

GCTCGCACTA GGGGGTCTTG AATTC 25

( 2 ) INFORMATION FOR SEQ ID NO:13:

( i ) SEQUENCE CHARACTERISTICS:
        ( A ) LENGTH: 44 base pairs
        ( B ) TYPE: nucleic acid
        ( C ) STRANDEDNESS: both
        ( D ) TOPOLOGY: linear ( i i ) MOLECULE TYPE: other nucleic acid
        ( A ) DESCRIPTION: /desc = "oligonucleotide primer,
            double- stranded from nucleotide 37-44, 3'end of short
            strand blocked with amino group."

( i i i ) HYPOTHETICAL: NO ( i v ) ANTI-SENSE: NO ( i x ) FEATURE:
        ( A ) NAME/KEY: misc_feature
        ( B ) LOCATION: 37..44
        ( D ) OTHER INFORMATION: /note= "Double stranded in the
            region from nucleotides 37-44, the 3'end is blocked
            with an amino group to reduce non-specific priming."

( x i ) SEQUENCE DESCRIPTION: SEQ ID NO:13:

CTAATACGAC TCACTATAGG GCTCGAGCGG CCGCCCGGGC AGGT 44

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:14:

CCATCCTAAT ACGACTCACT ATAGGGC 27

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:15:

CCATTGACAT GAAGACCGTT TCTC 24

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

ACTCACTATA GGGCTCGAGC GGC                                                                          23

(2) INFORMATION FOR SEQ ID NO:17:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:17:

GGGTGCAAAG CGCTGACATC AGTG                                                                         24

(2) INFORMATION FOR SEQ ID NO:18:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:18:

CCTCTCGAGC CACCATGTCG AGCCACCATG CAGCTAGAGC TCTCCACCTG                                              50

(2) INFORMATION FOR SEQ ID NO:19:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:19:

CGCGCGGCCG CGCATCTGGC AAAGCTGAGT T                                                                  31

(2) INFORMATION FOR SEQ ID NO:20:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: YES (ix) FEATURE:
  (A) NAME/KEY: misc_feature
  (B) LOCATION: 25..27
  (D) OTHER INFORMATION: /note= "At position 25, R is A or G."

(xi) SEQUENCE DESCRIPTION: SEQ ID NO:20:

GAAATAAGCC CAGGCTTTGC AGTCRAA 27

(2) INFORMATION FOR SEQ ID NO:21:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: NO (ix) FEATURE:
    (A) NAME/KEY: misc_feature
    (B) LOCATION: 21..22
    (D) OTHER INFORMATION: /note= "At position 22, N is A, G, C or T."

(xi) SEQUENCE DESCRIPTION: SEQ ID NO:21:

AGGAAATTCC ACTGGAACCT TN 22

(2) INFORMATION FOR SEQ ID NO:22:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: YES (ix) FEATURE:
    (A) NAME/KEY: misc_feature
    (B) LOCATION: 1..25
    (D) OTHER INFORMATION: /note= "At position 25, N is A, G, C or T."

(xi) SEQUENCE DESCRIPTION: SEQ ID NO:22:

CTGGGGGTGA ATTCGAAGGT AGCGN 25

(2) INFORMATION FOR SEQ ID NO:23:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:23:

```
GAGTTCATCG GGAAGACCTG TTG                                                          23
```

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:24:

```
ACAGCCCATC AACTCCATGC GAAG                                                         24
```

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:25:

```
TCAGGGCAAT CAGGACTCC                                                               19
```

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:26:

```
CCGTGGTGAA CGCTCTGGAC C                                                            21
```

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:27:

```
GTAGAGGTCC TGTGCCTCGC AGCC                                                         24
```

( 2 ) INFORMATION FOR SEQ ID NO:28:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..27
        ( D ) OTHER INFORMATION: /note= "S is G or C, K is G or T, R
            is A or G, and Y is C or T."

( x i ) SEQUENCE DESCRIPTION: SEQ ID NO:28:

GTAGAGSTSC TGKGCCTCRC AKCCYAG     27

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:29:

CTTCGCATGG AGTTGATGGG CTGT     24

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:30:

AATCAGGACT CCTCCACCCC CG     22

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:31:

GGATCCACCC CACGAGCTGG     20

( 2 ) INFORMATION FOR SEQ ID NO:32:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:32:

CGCCCTGAGG CTCGAGGTTC TAGG     24

( 2 ) INFORMATION FOR SEQ ID NO:33:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:33:

AATCAGGACT CCTCCACCCC CG     22

( 2 ) INFORMATION FOR SEQ ID NO:34:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:34:

CCTTGCAGGA ATTCGATTCA     20

( 2 ) INFORMATION FOR SEQ ID NO:35:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:35:

CCGTGGTGAA CGCTCTGGAC C     21

( 2 ) INFORMATION FOR SEQ ID NO:36:

-continued ( i ) SEQUENCE CHARACTERISTICS:
    ( A ) LENGTH: 6402 base pairs
    ( B ) TYPE: nucleic acid
    ( C ) STRANDEDNESS: double
    ( D ) TOPOLOGY: Not Relevant ( i i ) MOLECULE TYPE: cDNA to mRNA ( i i i ) HYPOTHETICAL: NO ( v i ) ORIGINAL SOURCE:
    ( A ) ORGANISM: Pig ( i x ) FEATURE:
    ( A ) NAME/KEY: CDS
    ( B ) LOCATION: 1..6402

( x i ) SEQUENCE DESCRIPTION: SEQ ID NO:36:

```
ATG CAG CTA GAG CTC TCC ACC TGT GTC TTT CTG TGT CTC TTG CCA CTC     48
Met Gln Leu Glu Leu Ser Thr Cys Val Phe Leu Cys Leu Leu Pro Leu
 1               5                  10                  15

GGC TTT AGT GCC ATC AGG AGA TAC TAC CTG GGC GCA GTG GAA CTG TCC     96
Gly Phe Ser Ala Ile Arg Arg Tyr Tyr Leu Gly Ala Val Glu Leu Ser
             20                  25                  30

TGG GAC TAC CGG CAA AGT GAA CTC CTC CGT GAG CTG CAC GTG GAC ACC    144
Trp Asp Tyr Arg Gln Ser Glu Leu Leu Arg Glu Leu His Val Asp Thr
         35                  40                  45

AGA TTT CCT GCT ACA GCG CCA GGA GCT CTT CCG TTG GGC CCG TCA GTC    192
Arg Phe Pro Ala Thr Ala Pro Gly Ala Leu Pro Leu Gly Pro Ser Val
     50                  55                  60

CTG TAC AAA AAG ACT GTG TTC GTA GAG TTC ACG GAT CAA CTT TTC AGC    240
Leu Tyr Lys Lys Thr Val Phe Val Glu Phe Thr Asp Gln Leu Phe Ser
 65                  70                  75                  80

GTT GCC AGG CCC AGG CCA CCA TGG ATG GGT CTG CTG GGT CCT ACC ATC    288
Val Ala Arg Pro Arg Pro Pro Trp Met Gly Leu Leu Gly Pro Thr Ile
                 85                  90                  95

CAG GCT GAG GTT TAC GAC ACG GTG GTC GTT ACC CTG AAG AAC ATG GCT    336
Gln Ala Glu Val Tyr Asp Thr Val Val Val Thr Leu Lys Asn Met Ala
             100                 105                 110

TCT CAT CCC GTT AGT CTT CAC GCT GTC GGC GTC TCC TTC TGG AAA TCT    384
Ser His Pro Val Ser Leu His Ala Val Gly Val Ser Phe Trp Lys Ser
         115                 120                 125

TCC GAA GGC GCT GAA TAT GAG GAT CAC ACC AGC CAA AGG GAG AAG GAA    432
Ser Glu Gly Ala Glu Tyr Glu Asp His Thr Ser Gln Arg Glu Lys Glu
     130                 135                 140

GAC GAT AAA GTC CTT CCC GGT AAA AGC CAA ACC TAC GTC TGG CAG GTC    480
Asp Asp Lys Val Leu Pro Gly Lys Ser Gln Thr Tyr Val Trp Gln Val
145                 150                 155                 160

CTG AAA GAA AAT GGT CCA ACA GCC TCT GAC CCA CCA TGT CTC ACC TAC    528
Leu Lys Glu Asn Gly Pro Thr Ala Ser Asp Pro Pro Cys Leu Thr Tyr
                 165                 170                 175

TCA TAC CTG TCT CAC GTG GAC CTG GTG AAA GAC CTG AAT TCG GGC CTC    576
Ser Tyr Leu Ser His Val Asp Leu Val Lys Asp Leu Asn Ser Gly Leu
             180                 185                 190

ATT GGA GCC CTG CTG GTT TGT AGA GAA GGG AGT CTG ACC AGA GAA AGG    624
Ile Gly Ala Leu Leu Val Cys Arg Glu Gly Ser Leu Thr Arg Glu Arg
         195                 200                 205

ACC CAG AAC CTG CAC GAA TTT GTA CTA CTT TTT GCT GTC TTT GAT GAA    672
Thr Gln Asn Leu His Glu Phe Val Leu Leu Phe Ala Val Phe Asp Glu
     210                 215                 220

GGG AAA AGT TGG CAC TCA GCA AGA AAT GAC TCC TGG ACA CGG GCC ATG    720
Gly Lys Ser Trp His Ser Ala Arg Asn Asp Ser Trp Thr Arg Ala Met
225                 230                 235                 240

GAT CCC GCA CCT GCC AGG GCC CAG CCT GCA ATG CAC ACA GTC AAT GGC    768
```

|  |  |  |  |  |  |  |  |  |  |  |  |  |  |  |  |
|---|---|---|---|---|---|---|---|---|---|---|---|---|---|---|---|
| Asp | Pro | Ala | Pro | Ala | Arg | Ala | Gln | Pro | Ala | Met | His | Thr | Val | Asn | Gly |
|  |  |  |  | 245 |  |  |  | 250 |  |  |  |  | 255 |  |  |

| TAT | GTC | AAC | AGG | TCT | CTG | CCA | GGT | CTG | ATC | GGA | TGT | CAT | AAG | AAA | TCA | 816 |
|---|---|---|---|---|---|---|---|---|---|---|---|---|---|---|---|---|
| Tyr | Val | Asn | Arg | Ser | Leu | Pro | Gly | Leu | Ile | Gly | Cys | His | Lys | Lys | Ser |  |
|  |  |  | 260 |  |  |  |  | 265 |  |  |  | 270 |  |  |  |  |

| GTC | TAC | TGG | CAC | GTG | ATT | GGA | ATG | GGC | ACC | AGC | CCG | GAA | GTG | CAC | TCC | 864 |
|---|---|---|---|---|---|---|---|---|---|---|---|---|---|---|---|---|
| Val | Tyr | Trp | His | Val | Ile | Gly | Met | Gly | Thr | Ser | Pro | Glu | Val | His | Ser |  |
|  |  | 275 |  |  |  |  | 280 |  |  |  |  | 285 |  |  |  |  |

| ATT | TTT | CTT | GAA | GGC | CAC | ACG | TTT | CTC | GTG | AGG | CAC | CAT | CGC | CAG | GCT | 912 |
|---|---|---|---|---|---|---|---|---|---|---|---|---|---|---|---|---|
| Ile | Phe | Leu | Glu | Gly | His | Thr | Phe | Leu | Val | Arg | His | His | Arg | Gln | Ala |  |
|  | 290 |  |  |  |  | 295 |  |  |  |  | 300 |  |  |  |  |  |

| TCC | TTG | GAG | ATC | TCG | CCA | CTA | ACT | TTC | CTC | ACT | GCT | CAG | ACA | TTC | CTG | 960 |
|---|---|---|---|---|---|---|---|---|---|---|---|---|---|---|---|---|
| Ser | Leu | Glu | Ile | Ser | Pro | Leu | Thr | Phe | Leu | Thr | Ala | Gln | Thr | Phe | Leu |  |
| 305 |  |  |  |  | 310 |  |  |  |  | 315 |  |  |  |  | 320 |  |

| ATG | GAC | CTT | GGC | CAG | TTC | CTA | CTG | TTT | TGT | CAT | ATC | TCT | TCC | CAC | CAC | 1008 |
|---|---|---|---|---|---|---|---|---|---|---|---|---|---|---|---|---|
| Met | Asp | Leu | Gly | Gln | Phe | Leu | Leu | Phe | Cys | His | Ile | Ser | Ser | His | His |  |
|  |  |  |  | 325 |  |  |  |  | 330 |  |  |  |  | 335 |  |  |

| CAT | GGT | GGC | ATG | GAG | GCT | CAC | GTC | AGA | GTA | GAA | AGC | TGC | GCC | GAG | GAG | 1056 |
|---|---|---|---|---|---|---|---|---|---|---|---|---|---|---|---|---|
| His | Gly | Gly | Met | Glu | Ala | His | Val | Arg | Val | Glu | Ser | Cys | Ala | Glu | Glu |  |
|  |  |  | 340 |  |  |  |  | 345 |  |  |  | 350 |  |  |  |  |

| CCC | CAG | CTG | CGG | AGG | AAA | GCT | GAT | GAA | GAG | GAA | GAT | TAT | GAT | GAC | AAT | 1104 |
|---|---|---|---|---|---|---|---|---|---|---|---|---|---|---|---|---|
| Pro | Gln | Leu | Arg | Arg | Lys | Ala | Asp | Glu | Glu | Glu | Asp | Tyr | Asp | Asp | Asn |  |
|  |  | 355 |  |  |  |  | 360 |  |  |  |  | 365 |  |  |  |  |

| TTG | TAC | GAC | TCG | GAC | ATG | GAC | GTG | GTC | CGG | CTC | GAT | GGT | GAC | GAC | GTG | 1152 |
|---|---|---|---|---|---|---|---|---|---|---|---|---|---|---|---|---|
| Leu | Tyr | Asp | Ser | Asp | Met | Asp | Val | Val | Arg | Leu | Asp | Gly | Asp | Asp | Val |  |
| 370 |  |  |  |  | 375 |  |  |  |  | 380 |  |  |  |  |  |  |

| TCT | CCC | TTT | ATC | CAA | ATC | CGC | TCG | GTT | GCC | AAG | AAG | CAT | CCC | AAA | ACC | 1200 |
|---|---|---|---|---|---|---|---|---|---|---|---|---|---|---|---|---|
| Ser | Pro | Phe | Ile | Gln | Ile | Arg | Ser | Val | Ala | Lys | Lys | His | Pro | Lys | Thr |  |
| 385 |  |  |  |  | 390 |  |  |  |  | 395 |  |  |  |  | 400 |  |

| TGG | GTG | CAC | TAC | ATC | TCT | GCA | GAG | GAG | GAG | GAC | TGG | GAC | TAC | GCC | CCC | 1248 |
|---|---|---|---|---|---|---|---|---|---|---|---|---|---|---|---|---|
| Trp | Val | His | Tyr | Ile | Ser | Ala | Glu | Glu | Glu | Asp | Trp | Asp | Tyr | Ala | Pro |  |
|  |  |  |  | 405 |  |  |  |  | 410 |  |  |  |  | 415 |  |  |

| GCG | GTC | CCC | AGC | CCC | AGT | GAC | AGA | AGT | TAT | AAA | AGT | CTC | TAC | TTG | AAC | 1296 |
|---|---|---|---|---|---|---|---|---|---|---|---|---|---|---|---|---|
| Ala | Val | Pro | Ser | Pro | Ser | Asp | Arg | Ser | Tyr | Lys | Ser | Leu | Tyr | Leu | Asn |  |
|  |  |  | 420 |  |  |  |  | 425 |  |  |  | 430 |  |  |  |  |

| AGT | GGT | CCT | CAG | CGA | ATT | GGT | AGG | AAA | TAC | AAA | AAA | GCT | CGA | TTC | GTC | 1344 |
|---|---|---|---|---|---|---|---|---|---|---|---|---|---|---|---|---|
| Ser | Gly | Pro | Gln | Arg | Ile | Gly | Arg | Lys | Tyr | Lys | Lys | Ala | Arg | Phe | Val |  |
|  |  | 435 |  |  |  |  | 440 |  |  |  |  | 445 |  |  |  |  |

| GCT | TAC | ACG | GAT | GTA | ACA | TTT | AAG | ACT | CGT | AAA | GCT | ATT | CCG | TAT | GAA | 1392 |
|---|---|---|---|---|---|---|---|---|---|---|---|---|---|---|---|---|
| Ala | Tyr | Thr | Asp | Val | Thr | Phe | Lys | Thr | Arg | Lys | Ala | Ile | Pro | Tyr | Glu |  |
| 450 |  |  |  |  | 455 |  |  |  |  | 460 |  |  |  |  |  |  |

| TCA | GGA | ATC | CTG | GGA | CCT | TTA | CTT | TAT | GGA | GAA | GTT | GGA | GAC | ACA | CTT | 1440 |
|---|---|---|---|---|---|---|---|---|---|---|---|---|---|---|---|---|
| Ser | Gly | Ile | Leu | Gly | Pro | Leu | Leu | Tyr | Gly | Glu | Val | Gly | Asp | Thr | Leu |  |
| 465 |  |  |  |  | 470 |  |  |  |  | 475 |  |  |  |  | 480 |  |

| TTG | ATT | ATA | TTT | AAG | AAT | AAA | GCG | AGC | CGA | CCA | TAT | AAC | ATC | TAC | CCT | 1488 |
|---|---|---|---|---|---|---|---|---|---|---|---|---|---|---|---|---|
| Leu | Ile | Ile | Phe | Lys | Asn | Lys | Ala | Ser | Arg | Pro | Tyr | Asn | Ile | Tyr | Pro |  |
|  |  |  | 485 |  |  |  |  | 490 |  |  |  |  | 495 |  |  |  |

| CAT | GGA | ATC | ACT | GAT | GTC | AGC | GCT | TTG | CAC | CCA | GGG | AGA | CTT | CTA | AAA | 1536 |
|---|---|---|---|---|---|---|---|---|---|---|---|---|---|---|---|---|
| His | Gly | Ile | Thr | Asp | Val | Ser | Ala | Leu | His | Pro | Gly | Arg | Leu | Leu | Lys |  |
|  |  | 500 |  |  |  |  | 505 |  |  |  |  | 510 |  |  |  |  |

| GGT | TGG | AAA | CAT | TTG | AAA | GAC | ATG | CCA | ATT | CTG | CCA | GGA | GAG | ACT | TTC | 1584 |
|---|---|---|---|---|---|---|---|---|---|---|---|---|---|---|---|---|
| Gly | Trp | Lys | His | Leu | Lys | Asp | Met | Pro | Ile | Leu | Pro | Gly | Glu | Thr | Phe |  |
|  |  | 515 |  |  |  |  | 520 |  |  |  |  | 525 |  |  |  |  |

| AAG | TAT | AAA | TGG | ACA | GTG | ACT | GTG | GAA | GAT | GGG | CCA | ACC | AAG | TCC | GAT | 1632 |
|---|---|---|---|---|---|---|---|---|---|---|---|---|---|---|---|---|
| Lys | Tyr | Lys | Trp | Thr | Val | Thr | Val | Glu | Asp | Gly | Pro | Thr | Lys | Ser | Asp |  |
|  | 530 |  |  |  |  | 535 |  |  |  |  | 540 |  |  |  |  |  |

| CCT | CGG | TGC | CTG | ACC | CGC | TAC | TAC | TCG | AGC | TCC | ATT | AAT | CTA | GAG | AAA | 1680 |
|---|---|---|---|---|---|---|---|---|---|---|---|---|---|---|---|---|
| Pro | Arg | Cys | Leu | Thr | Arg | Tyr | Tyr | Ser | Ser | Ser | Ile | Asn | Leu | Glu | Lys |  |
| 545 |  |  |  |  | 550 |  |  |  |  | 555 |  |  |  |  | 560 |  |

| GAT | CTG | GCT | TCG | GGA | CTC | ATT | GGC | CCT | CTC | CTC | ATC | TGC | TAC | AAA | GAA | 1728 |
|---|---|---|---|---|---|---|---|---|---|---|---|---|---|---|---|---|

```
              Asp  Leu  Ala  Ser  Gly  Leu  Ile  Gly  Pro  Leu  Leu  Ile  Cys  Tyr  Lys  Glu
                             565                 570                     575

TCT  GTA  GAC  CAA  AGA  GGA  AAC  CAG  ATG  ATG  TCA  GAC  AAG  AGA  AAC  GTC                  1776
Ser  Val  Asp  Gln  Arg  Gly  Asn  Gln  Met  Met  Ser  Asp  Lys  Arg  Asn  Val
               580                      585                     590

ATC  CTG  TTT  TCT  GTA  TTC  GAT  GAG  AAT  CAA  AGC  TGG  TAC  CTC  GCA  GAG                  1824
Ile  Leu  Phe  Ser  Val  Phe  Asp  Glu  Asn  Gln  Ser  Trp  Tyr  Leu  Ala  Glu
               595                      600                     605

AAT  ATT  CAG  CGC  TTC  CTC  CCC  AAT  CCG  GAT  GGA  TTA  CAG  CCC  CAG  GAT                  1872
Asn  Ile  Gln  Arg  Phe  Leu  Pro  Asn  Pro  Asp  Gly  Leu  Gln  Pro  Gln  Asp
          610                      615                     620

CCA  GAG  TTC  CAA  GCT  TCT  AAC  ATC  ATG  CAC  AGC  ATC  AAT  GGC  TAT  GTT                  1920
Pro  Glu  Phe  Gln  Ala  Ser  Asn  Ile  Met  His  Ser  Ile  Asn  Gly  Tyr  Val
625                      630                     635                          640

TTT  GAT  AGC  TTG  CAG  CTG  TCG  GTT  TGT  TTG  CAC  GAG  GTG  GCA  TAC  TGG                  1968
Phe  Asp  Ser  Leu  Gln  Leu  Ser  Val  Cys  Leu  His  Glu  Val  Ala  Tyr  Trp
                    645                      650                     655

TAC  ATT  CTA  AGT  GTT  GGA  GCA  CAG  ACG  GAC  TTC  CTC  TCC  GTC  TTC  TTC                  2016
Tyr  Ile  Leu  Ser  Val  Gly  Ala  Gln  Thr  Asp  Phe  Leu  Ser  Val  Phe  Phe
                    660                      665                     670

TCT  GGC  TAC  ACC  TTC  AAA  CAC  AAA  ATG  GTC  TAT  GAA  GAC  ACA  CTC  ACC                  2064
Ser  Gly  Tyr  Thr  Phe  Lys  His  Lys  Met  Val  Tyr  Glu  Asp  Thr  Leu  Thr
               675                      680                     685

CTG  TTC  CCC  TTC  TCA  GGA  GAA  ACG  GTC  TTC  ATG  TCA  ATG  GAA  AAC  CCA                  2112
Leu  Phe  Pro  Phe  Ser  Gly  Glu  Thr  Val  Phe  Met  Ser  Met  Glu  Asn  Pro
     690                      695                     700

GGT  CTC  TGG  GTC  CTA  GGG  TGC  CAC  AAC  TCA  GAC  TTG  CGG  AAC  AGA  GGG                  2160
Gly  Leu  Trp  Val  Leu  Gly  Cys  His  Asn  Ser  Asp  Leu  Arg  Asn  Arg  Gly
705                      710                     715                          720

ATG  ACA  GCC  TTA  CTG  AAG  GTG  TAT  AGT  TGT  GAC  AGG  GAC  ATT  GGT  GAT                  2208
Met  Thr  Ala  Leu  Leu  Lys  Val  Tyr  Ser  Cys  Asp  Arg  Asp  Ile  Gly  Asp
                    725                      730                     735

TAT  TAT  GAC  AAC  ACT  TAT  GAA  GAT  ATT  CCA  GGC  TTC  TTG  CTG  AGT  GGA                  2256
Tyr  Tyr  Asp  Asn  Thr  Tyr  Glu  Asp  Ile  Pro  Gly  Phe  Leu  Leu  Ser  Gly
               740                      745                     750

AAG  AAT  GTC  ATT  GAA  CCC  AGA  AGC  TTT  GCC  CAG  AAT  TCA  AGA  CCC  CCT                  2304
Lys  Asn  Val  Ile  Glu  Pro  Arg  Ser  Phe  Ala  Gln  Asn  Ser  Arg  Pro  Pro
               755                      760                     765

AGT  GCG  AGC  CAA  AAG  CAA  TTC  CAA  ACC  ATC  ACA  AGT  CCA  GAA  GAT  GAC                  2352
Ser  Ala  Ser  Gln  Lys  Gln  Phe  Gln  Thr  Ile  Thr  Ser  Pro  Glu  Asp  Asp
     770                      775                     780

GTG  GAG  CTT  GAC  CCG  CAG  TCT  GGA  GAG  AGA  ACC  CAA  GCA  CTG  GAA  GAA                  2400
Val  Glu  Leu  Asp  Pro  Gln  Ser  Gly  Glu  Arg  Thr  Gln  Ala  Leu  Glu  Glu
785                      790                     795                          800

CTA  AGT  GTC  CCC  TCT  GGT  GAT  GGG  TCG  ATG  CTC  TTG  GGA  CAG  AAT  CCT                  2448
Leu  Ser  Val  Pro  Ser  Gly  Asp  Gly  Ser  Met  Leu  Leu  Gly  Gln  Asn  Pro
                    805                      810                     815

GCT  CCA  CAT  GGC  TCA  TCC  TCA  TCT  GAT  CTT  CAA  GAA  GCC  AGG  AAT  GAG                  2496
Ala  Pro  His  Gly  Ser  Ser  Ser  Ser  Asp  Leu  Gln  Glu  Ala  Arg  Asn  Glu
               820                      825                     830

GCT  GAT  GAT  TAT  TTA  CCT  GGA  GCA  AGA  GAA  AGA  AAC  ACG  GCC  CCA  TCC                  2544
Ala  Asp  Asp  Tyr  Leu  Pro  Gly  Ala  Arg  Glu  Arg  Asn  Thr  Ala  Pro  Ser
               835                      840                     845

GCA  GCG  GCA  CGT  CTC  AGA  CCA  GAG  CTG  CAT  CAC  AGT  GCC  GAA  AGA  GTA                  2592
Ala  Ala  Ala  Arg  Leu  Arg  Pro  Glu  Leu  His  His  Ser  Ala  Glu  Arg  Val
850                      855                     860

CTT  ACT  CCT  GAG  CCA  GAG  AAA  GAG  TTG  AAG  AAA  CTT  GAT  TCA  AAA  ATG                  2640
Leu  Thr  Pro  Glu  Pro  Glu  Lys  Glu  Leu  Lys  Lys  Leu  Asp  Ser  Lys  Met
865                      870                     875                          880

TCT  AGT  TCA  TCA  GAC  CTT  CTA  AAG  ACT  TCG  CCA  ACA  ATT  CCA  TCA  GAC                  2688
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Ser   | Ser   | Ser   | Ser   | Asp   | Leu   | Leu   | Lys   | Thr   | Ser   | Pro   | Thr   | Ile   | Pro   | Ser   | Asp   |      |
|       |       |       |       | 885   |       |       |       |       | 890   |       |       |       |       | 895   |       |      |

```
ACG TTG TCA GCG GAG ACT GAA AGG ACA CAT TCC TTA GGC CCC CCA CAC       2736
Thr Leu Ser Ala Glu Thr Glu Arg Thr His Ser Leu Gly Pro Pro His
            900             905             910

CCG CAG GTT AAT TTC AGG AGT CAA TTA GGT GCC ATT GTA CTT GGC AAA       2784
Pro Gln Val Asn Phe Arg Ser Gln Leu Gly Ala Ile Val Leu Gly Lys
            915             920             925

AAT TCA TCT CAC TTT ATT GGG GCT GGT GTC CCT TTG GGC TCG ACT GAG       2832
Asn Ser Ser His Phe Ile Gly Ala Gly Val Pro Leu Gly Ser Thr Glu
            930             935             940

GAG GAT CAT GAA AGC TCC CTG GGA GAA AAT GTA TCA CCA GTG GAG AGT       2880
Glu Asp His Glu Ser Ser Leu Gly Glu Asn Val Ser Pro Val Glu Ser
945             950             955             960

GAC GGG ATA TTT GAA AAG GAA AGA GCT CAT GGA CCT GCT TCA CTG ACC       2928
Asp Gly Ile Phe Glu Lys Glu Arg Ala His Gly Pro Ala Ser Leu Thr
            965             970             975

AAA GAC GAT GTT TTA TTT AAA GTT AAT ATC TCT TTG GTA AAG ACA AAC       2976
Lys Asp Asp Val Leu Phe Lys Val Asn Ile Ser Leu Val Lys Thr Asn
            980             985             990

AAG GCA CGA GTT TAC TTA AAA ACT AAT AGA AAG ATT CAC ATT GAT GAC       3024
Lys Ala Arg Val Tyr Leu Lys Thr Asn Arg Lys Ile His Ile Asp Asp
            995             1000            1005

GCA GCT TTA TTA ACT GAG AAT AGG GCA TCT GCA ACG TTT ATG GAC AAA       3072
Ala Ala Leu Leu Thr Glu Asn Arg Ala Ser Ala Thr Phe Met Asp Lys
1010            1015            1020

AAT ACT ACA GCT TCG GGA TTA AAT CAT GTG TCA AAT TGG ATA AAA GGG       3120
Asn Thr Thr Ala Ser Gly Leu Asn His Val Ser Asn Trp Ile Lys Gly
1025            1030            1035            1040

CCC CTT GGC AAG AAC CCC CTA AGC TCG GAG CGA GGC CCC AGT CCA GAG       3168
Pro Leu Gly Lys Asn Pro Leu Ser Ser Glu Arg Gly Pro Ser Pro Glu
            1045            1050            1055

CTT CTG ACA TCT TCA GGA TCA GGA AAA TCT GTG AAA GGT CAG AGT TCT       3216
Leu Leu Thr Ser Ser Gly Ser Gly Lys Ser Val Lys Gly Gln Ser Ser
            1060            1065            1070

GGG CAG GGG AGA ATA CGG GTG GCA GTG GAA GAG GAA GAA CTG AGC AAA       3264
Gly Gln Gly Arg Ile Arg Val Ala Val Glu Glu Glu Glu Leu Ser Lys
1075            1080            1085

GGC AAA GAG ATG ATG CTT CCC AAC AGC GAG CTC ACC TTT CTC ACT AAC       3312
Gly Lys Glu Met Met Leu Pro Asn Ser Glu Leu Thr Phe Leu Thr Asn
1090            1095            1100

TCG GCT GAT GTC CAA GGA AAC GAT ACA CAC AGT CAA GGA AAA AAG TCT       3360
Ser Ala Asp Val Gln Gly Asn Asp Thr His Ser Gln Gly Lys Lys Ser
1105            1110            1115            1120

CGG GAA GAG ATG GAA AGG AGA GAA AAA TTA GTC CAA GAA AAA GTC GAC       3408
Arg Glu Glu Met Glu Arg Arg Glu Lys Leu Val Gln Glu Lys Val Asp
            1125            1130            1135

TTG CCT CAG GTG TAT ACA GCG ACT GGA ACT AAG AAT TTC CTG AGA AAC       3456
Leu Pro Gln Val Tyr Thr Ala Thr Gly Thr Lys Asn Phe Leu Arg Asn
            1140            1145            1150

ATT TTT CAC CAA AGC ACT GAG CCC AGT GTA GAA GGG TTT GAT GGG GGG       3504
Ile Phe His Gln Ser Thr Glu Pro Ser Val Glu Gly Phe Asp Gly Gly
            1155            1160            1165

TCA CAT GCG CCG GTG CCT CAA GAC AGC AGG TCA TTA AAT GAT TCG GCA       3552
Ser His Ala Pro Val Pro Gln Asp Ser Arg Ser Leu Asn Asp Ser Ala
            1170            1175            1180

GAG AGA GCA GAG ACT CAC ATA GCC CAT TTC TCA GCA ATT AGG GAA GAG       3600
Glu Arg Ala Glu Thr His Ile Ala His Phe Ser Ala Ile Arg Glu Glu
1185            1190            1195            1200

GCA CCC TTG GAA GCC CCG GGA AAT CGA ACA GGT CCA GGT CCG AGG AGT       3648
```

| | | | | | | | | | | | | | | | |
|---|---|---|---|---|---|---|---|---|---|---|---|---|---|---|---|
|Ala|Pro|Leu|Glu|Ala|Pro|Gly|Asn|Arg|Thr|Gly|Pro|Gly|Pro|Arg|Ser|
| | | | |1205| | | |1210| | | |1215| | | |

```
GCG GTT CCC CGC CGC GTT AAG CAG AGC TTG AAA CAG ATC AGA CTC CCG      3696
Ala Val Pro Arg Arg Val Lys Gln Ser Leu Lys Gln Ile Arg Leu Pro
            1220                1225                1230

CTA GAA GAA ATA AAG CCT GAA AGG GGG GTG GTT CTG AAT GCC ACC TCA      3744
Leu Glu Glu Ile Lys Pro Glu Arg Gly Val Val Leu Asn Ala Thr Ser
1235                1240                1245

ACC CGG TGG TCT GAA AGC AGT CCT ATC TTA CAA GGA GCC AAA AGA AAT      3792
Thr Arg Trp Ser Glu Ser Ser Pro Ile Leu Gln Gly Ala Lys Arg Asn
        1250                1255                1260

AAC CTT TCT TTA CCT TTC CTG ACC TTG GAA ATG GCC GGA GGT CAA GGA      3840
Asn Leu Ser Leu Pro Phe Leu Thr Leu Glu Met Ala Gly Gly Gln Gly
1265                1270                1275                1280

AAG ATC AGC GCC CTG GGG AAA AGT GCC GCA GGC CCG CTG GCG TCC GGG      3888
Lys Ile Ser Ala Leu Gly Lys Ser Ala Ala Gly Pro Leu Ala Ser Gly
                1285                1290                1295

AAG CTG GAG AAG GCT GTT CTC TCT TCA GCA GGC TTG TCT GAA GCA TCT      3936
Lys Leu Glu Lys Ala Val Leu Ser Ser Ala Gly Leu Ser Glu Ala Ser
            1300                1305                1310

GGC AAA GCT GAG TTT CTT CCT AAA GTT CGA GTT CAT CGG GAA GAC CTG      3984
Gly Lys Ala Glu Phe Leu Pro Lys Val Arg Val His Arg Glu Asp Leu
        1315                1320                1325

TTG CCT CAA AAA ACC AGC AAT GTT TCT TGC GCA CAC GGG GAT CTC GGC      4032
Leu Pro Gln Lys Thr Ser Asn Val Ser Cys Ala His Gly Asp Leu Gly
1330                1335                1340

CAG GAG ATC TTC CTG CAG AAA ACA CGG GGA CCT GTT AAC CTG AAC AAA      4080
Gln Glu Ile Phe Leu Gln Lys Thr Arg Gly Pro Val Asn Leu Asn Lys
1345                1350                1355                1360

GTA AAT AGA CCT GGA AGG ACT CCC TCC AAG CTT CTG GGT CCC CCG ATG      4128
Val Asn Arg Pro Gly Arg Thr Pro Ser Lys Leu Leu Gly Pro Pro Met
                1365                1370                1375

CCC AAA GAG TGG GAA TCC CTA GAG AAG TCA CCA AAA AGC ACA GCT CTC      4176
Pro Lys Glu Trp Glu Ser Leu Glu Lys Ser Pro Lys Ser Thr Ala Leu
            1380                1385                1390

AGG ACG AAA GAC ATC ATC AGT TTA CCC CTG GAC CGT CAC GAA AGC AAT      4224
Arg Thr Lys Asp Ile Ile Ser Leu Pro Leu Asp Arg His Glu Ser Asn
        1395                1400                1405

CAT TCA ATA GCA GCA AAA AAT GAA GGA CAA GCC GAG ACC CAA AGA GAA      4272
His Ser Ile Ala Ala Lys Asn Glu Gly Gln Ala Glu Thr Gln Arg Glu
1410                1415                1420

GCC GCC TGG ACG AAG CAG GGA GGG CCT GGA AGG CTG TGC GCT CCA AAG      4320
Ala Ala Trp Thr Lys Gln Gly Gly Pro Gly Arg Leu Cys Ala Pro Lys
1425                1430                1435                1440

CCT CCG GTC CTG CGA CGG CAT CAG AGG GAC ATA AGC CTT CCT ACT TTT      4368
Pro Pro Val Leu Arg Arg His Gln Arg Asp Ile Ser Leu Pro Thr Phe
                1445                1450                1455

CAG CCG GAG GAA GAC AAA ATG GAC TAT GAT GAT ATC TTC TCA ACT GAA      4416
Gln Pro Glu Glu Asp Lys Met Asp Tyr Asp Asp Ile Phe Ser Thr Glu
            1460                1465                1470

ACG AAG GGA GAA GAT TTT GAC ATT TAC GGT GAG GAT GAA AAT CAG GAC      4464
Thr Lys Gly Glu Asp Phe Asp Ile Tyr Gly Glu Asp Glu Asn Gln Asp
        1475                1480                1485

CCT CGC AGC TTT CAG AAG AGA ACC CGA CAC TAT TTC ATT GCT GCG GTG      4512
Pro Arg Ser Phe Gln Lys Arg Thr Arg His Tyr Phe Ile Ala Ala Val
1490                1495                1500

GAG CAG CTC TGG GAT TAC GGG ATG AGC GAA TCC CCC CGG GCG CTA AGA      4560
Glu Gln Leu Trp Asp Tyr Gly Met Ser Glu Ser Pro Arg Ala Leu Arg
1505                1510                1515                1520

AAC AGG GCT CAG AAC GGA GAG GTG CCT CGG TTC AAG AAG GTG GTC TTC      4608
```

-continued

```
Asn  Arg  Ala  Gln  Asn  Gly  Glu  Val  Pro  Arg  Phe  Lys  Lys  Val  Val  Phe
               1525                     1530                     1535

CGG  GAA  TTT  GCT  GAC  GGC  TCC  TTC  ACG  CAG  CCG  TCG  TAC  CGC  GGG  GAA       4656
Arg  Glu  Phe  Ala  Asp  Gly  Ser  Phe  Thr  Gln  Pro  Ser  Tyr  Arg  Gly  Glu
               1540                     1545                     1550

CTC  AAC  AAA  CAC  TTG  GGG  CTC  TTG  GGA  CCC  TAC  ATC  AGA  GCG  GAA  GTT       4704
Leu  Asn  Lys  His  Leu  Gly  Leu  Leu  Gly  Pro  Tyr  Ile  Arg  Ala  Glu  Val
               1555                     1560                     1565

GAA  GAC  AAC  ATC  ATG  GTA  ACT  TTC  AAA  AAC  CAG  GCG  TCT  CGT  CCC  TAT       4752
Glu  Asp  Asn  Ile  Met  Val  Thr  Phe  Lys  Asn  Gln  Ala  Ser  Arg  Pro  Tyr
               1570                     1575                     1580

TCC  TTC  TAC  TCG  AGC  CTT  ATT  TCT  TAT  CCG  GAT  GAT  CAG  GAG  CAA  GGG       4800
Ser  Phe  Tyr  Ser  Ser  Leu  Ile  Ser  Tyr  Pro  Asp  Asp  Gln  Glu  Gln  Gly
1585                1590                     1595                     1600

GCA  GAA  CCT  CGA  CAC  AAC  TTC  GTC  CAG  CCA  AAT  GAA  ACC  AGA  ACT  TAC       4848
Ala  Glu  Pro  Arg  His  Asn  Phe  Val  Gln  Pro  Asn  Glu  Thr  Arg  Thr  Tyr
               1605                     1610                     1615

TTT  TGG  AAA  GTG  CAG  CAT  CAC  ATG  GCA  CCC  ACA  GAA  GAC  GAG  TTT  GAC       4896
Phe  Trp  Lys  Val  Gln  His  His  Met  Ala  Pro  Thr  Glu  Asp  Glu  Phe  Asp
               1620                     1625                     1630

TGC  AAA  GCC  TGG  GCC  TAC  TTT  TCT  GAT  GTT  GAC  CTG  GAA  AAA  GAT  GTG       4944
Cys  Lys  Ala  Trp  Ala  Tyr  Phe  Ser  Asp  Val  Asp  Leu  Glu  Lys  Asp  Val
               1635                     1640                     1645

CAC  TCA  GGC  TTG  ATC  GGC  CCC  CTT  CTG  ATC  TGC  CGC  GCC  AAC  ACC  CTG       4992
His  Ser  Gly  Leu  Ile  Gly  Pro  Leu  Leu  Ile  Cys  Arg  Ala  Asn  Thr  Leu
               1650                     1655                     1660

AAC  GCT  GCT  CAC  GGT  AGA  CAA  GTG  ACC  GTG  CAA  GAA  TTT  GCT  CTG  TTT       5040
Asn  Ala  Ala  His  Gly  Arg  Gln  Val  Thr  Val  Gln  Glu  Phe  Ala  Leu  Phe
1665                1670                     1675                     1680

TTC  ACT  ATT  TTT  GAT  GAG  ACA  AAG  AGC  TGG  TAC  TTC  ACT  GAA  AAT  GTG       5088
Phe  Thr  Ile  Phe  Asp  Glu  Thr  Lys  Ser  Trp  Tyr  Phe  Thr  Glu  Asn  Val
               1685                     1690                     1695

GAA  AGG  AAC  TGC  CGG  GCC  CCC  TGC  CAC  CTG  CAG  ATG  GAG  GAC  CCC  ACT       5136
Glu  Arg  Asn  Cys  Arg  Ala  Pro  Cys  His  Leu  Gln  Met  Glu  Asp  Pro  Thr
               1700                     1705                     1710

CTG  AAA  GAA  AAC  TAT  CGC  TTC  CAT  GCA  ATC  AAT  GGC  TAT  GTG  ATG  GAT       5184
Leu  Lys  Glu  Asn  Tyr  Arg  Phe  His  Ala  Ile  Asn  Gly  Tyr  Val  Met  Asp
               1715                     1720                     1725

ACA  CTC  CCT  GGC  TTA  GTA  ATG  GCT  CAG  AAT  CAA  AGG  ATC  CGA  TGG  TAT       5232
Thr  Leu  Pro  Gly  Leu  Val  Met  Ala  Gln  Asn  Gln  Arg  Ile  Arg  Trp  Tyr
               1730                     1735                     1740

CTG  CTC  AGC  ATG  GGC  AGC  AAT  GAA  AAT  ATC  CAT  TCG  ATT  CAT  TTT  AGC       5280
Leu  Leu  Ser  Met  Gly  Ser  Asn  Glu  Asn  Ile  His  Ser  Ile  His  Phe  Ser
1745                1750                     1755                     1760

GGA  CAC  GTG  TTC  AGT  GTA  CGG  AAA  AAG  GAG  GAG  TAT  AAA  ATG  GCC  GTG       5328
Gly  His  Val  Phe  Ser  Val  Arg  Lys  Lys  Glu  Glu  Tyr  Lys  Met  Ala  Val
               1765                     1770                     1775

TAC  AAT  CTC  TAT  CCG  GGT  GTC  TTT  GAG  ACA  GTG  GAA  ATG  CTA  CCG  TCC       5376
Tyr  Asn  Leu  Tyr  Pro  Gly  Val  Phe  Glu  Thr  Val  Glu  Met  Leu  Pro  Ser
               1780                     1785                     1790

AAA  GTT  GGA  ATT  TGG  CGA  ATA  GAA  TGC  CTG  ATT  GGC  GAG  CAC  CTG  CAA       5424
Lys  Val  Gly  Ile  Trp  Arg  Ile  Glu  Cys  Leu  Ile  Gly  Glu  His  Leu  Gln
               1795                     1800                     1805

GCT  GGG  ATG  AGC  ACG  ACT  TTC  CTG  GTG  TAC  AGC  AAG  GAG  TGT  CAG  GCT       5472
Ala  Gly  Met  Ser  Thr  Thr  Phe  Leu  Val  Tyr  Ser  Lys  Glu  Cys  Gln  Ala
               1810                     1815                     1820

CCA  CTG  GGA  ATG  GCT  TCT  GGA  CGC  ATT  AGA  GAT  TTT  CAG  ATC  ACA  GCT       5520
Pro  Leu  Gly  Met  Ala  Ser  Gly  Arg  Ile  Arg  Asp  Phe  Gln  Ile  Thr  Ala
1825                1830                     1835                     1840

TCA  GGA  CAG  TAT  GGA  CAG  TGG  GCC  CCA  AAG  CTG  GCC  AGA  CTT  CAT  TAT       5568
```

```
Ser Gly Gln Tyr Gly Gln Trp Ala Pro Lys Leu Ala Arg Leu His Tyr
            1845                1850                1855

TCC GGA TCA ATC AAT GCC TGG AGC ACC AAG GAT CCC CAC TCC TGG ATC      5616
Ser Gly Ser Ile Asn Ala Trp Ser Thr Lys Asp Pro His Ser Trp Ile
        1860                1865                1870

AAG GTG GAT CTG TTG GCA CCA ATG ATC ATT CAC GGC ATC ATG ACC CAG      5664
Lys Val Asp Leu Leu Ala Pro Met Ile Ile His Gly Ile Met Thr Gln
            1875                1880                1885

GGT GCC CGT CAG AAG TTT TCC AGC CTC TAC ATC TCC CAG TTT ATC ATC      5712
Gly Ala Arg Gln Lys Phe Ser Ser Leu Tyr Ile Ser Gln Phe Ile Ile
        1890                1895                1900

ATG TAC AGT CTT GAC GGG AGG AAC TGG CAG AGT TAC CGA GGG AAT TCC      5760
Met Tyr Ser Leu Asp Gly Arg Asn Trp Gln Ser Tyr Arg Gly Asn Ser
1905                1910                1915                1920

ACG GGC ACC TTA ATG GTC TTC TTT GGC AAT GTG GAC GCA TCT GGG ATT      5808
Thr Gly Thr Leu Met Val Phe Phe Gly Asn Val Asp Ala Ser Gly Ile
            1925                1930                1935

AAA CAC AAT ATT TTT AAC CCT CCG ATT GTG GCT CGG TAC ATC CGT TTG      5856
Lys His Asn Ile Phe Asn Pro Pro Ile Val Ala Arg Tyr Ile Arg Leu
        1940                1945                1950

CAC CCA ACA CAT TAC AGC ATC CGC AGC ACT CTT CGC ATG GAG TTG ATG      5904
His Pro Thr His Tyr Ser Ile Arg Ser Thr Leu Arg Met Glu Leu Met
            1955                1960                1965

GGC TGT GAT TTA AAC AGT TGC AGC ATG CCC CTG GGA ATG CAG AAT AAA      5952
Gly Cys Asp Leu Asn Ser Cys Ser Met Pro Leu Gly Met Gln Asn Lys
        1970                1975                1980

GCG ATA TCA GAC TCA CAG ATC ACG GCC TCC TCC CAC CTA AGC AAT ATA      6000
Ala Ile Ser Asp Ser Gln Ile Thr Ala Ser Ser His Leu Ser Asn Ile
1985                1990                1995                2000

TTT GCC ACC TGG TCT CCT TCA CAA GCC CGA CTT CAC CTC CAG GGG CGG      6048
Phe Ala Thr Trp Ser Pro Ser Gln Ala Arg Leu His Leu Gln Gly Arg
            2005                2010                2015

ACG AAT GCC TGG CGA CCC CGG GTG AGC AGC GCA GAG GAG TGG CTG CAG      6096
Thr Asn Ala Trp Arg Pro Arg Val Ser Ser Ala Glu Glu Trp Leu Gln
        2020                2025                2030

GTG GAC CTG CAG AAG ACG GTG AAG GTC ACA GGC ATC ACC ACC CAG GGC      6144
Val Asp Leu Gln Lys Thr Val Lys Val Thr Gly Ile Thr Thr Gln Gly
            2035                2040                2045

GTG AAG TCC CTG CTC AGC AGC ATG TAT GTG AAG GAG TTC CTC GTG TCC      6192
Val Lys Ser Leu Leu Ser Ser Met Tyr Val Lys Glu Phe Leu Val Ser
        2050                2055                2060

AGT AGT CAG GAC GGC CGC CGC TGG ACC CTG TTT CTT CAG GAC GGC CAC      6240
Ser Ser Gln Asp Gly Arg Arg Trp Thr Leu Phe Leu Gln Asp Gly His
2065                2070                2075                2080

ACG AAG GTT TTT CAG GGC AAT CAG GAC TCC TCC ACC CCC GTG GTG AAC      6288
Thr Lys Val Phe Gln Gly Asn Gln Asp Ser Ser Thr Pro Val Val Asn
            2085                2090                2095

GCT CTG GAC CCC CCG CTG TTC ACG CGC TAC CTG AGG ATC CAC CCC ACG      6336
Ala Leu Asp Pro Pro Leu Phe Thr Arg Tyr Leu Arg Ile His Pro Thr
        2100                2105                2110

AGC TGG GCG CAG CAC ATC GCC CTG AGG CTC GAG GTT CTA GGA TGT GAG      6384
Ser Trp Ala Gln His Ile Ala Leu Arg Leu Glu Val Leu Gly Cys Glu
            2115                2120                2125

GCA CAG GAT CTC TAC TGA                                              6402
Ala Gln Asp Leu Tyr *
        2130
```

( 2 ) INFORMATION FOR SEQ ID NO:37:

( i ) SEQUENCE CHARACTERISTICS:

( A ) LENGTH: 2133 amino acids (B) TYPE: amino acid
(D) TOPOLOGY: linear (ii) MOLECULE TYPE: protein (xi) SEQUENCE DESCRIPTION: SEQ ID NO:37:

```
Met Gln Leu Glu Leu Ser Thr Cys Val Phe Leu Cys Leu Leu Pro Leu
 1               5                  10                  15
Gly Phe Ser Ala Ile Arg Arg Tyr Tyr Leu Gly Ala Val Glu Leu Ser
            20                  25                  30
Trp Asp Tyr Arg Gln Ser Glu Leu Leu Arg Glu Leu His Val Asp Thr
        35                  40                  45
Arg Phe Pro Ala Thr Ala Pro Gly Ala Leu Pro Leu Gly Pro Ser Val
    50                  55                  60
Leu Tyr Lys Lys Thr Val Phe Val Glu Phe Thr Asp Gln Leu Phe Ser
65                  70                  75                  80
Val Ala Arg Pro Arg Pro Pro Trp Met Gly Leu Leu Gly Pro Thr Ile
                85                  90                  95
Gln Ala Glu Val Tyr Asp Thr Val Val Thr Leu Lys Asn Met Ala
            100                 105                 110
Ser His Pro Val Ser Leu His Ala Val Gly Val Ser Phe Trp Lys Ser
        115                 120                 125
Ser Glu Gly Ala Glu Tyr Glu Asp His Thr Ser Gln Arg Glu Lys Glu
    130                 135                 140
Asp Asp Lys Val Leu Pro Gly Lys Ser Gln Thr Tyr Val Trp Gln Val
145                 150                 155                 160
Leu Lys Glu Asn Gly Pro Thr Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Thr Arg Glu Arg
        195                 200                 205
Thr Gln Asn Leu His Glu Phe Val Leu Leu Phe Ala Val Phe Asp Glu
    210                 215                 220
Gly Lys Ser Trp His Ser Ala Arg Asn Asp Ser Trp Thr Arg Ala Met
225                 230                 235                 240
Asp Pro Ala Pro Ala Arg Ala Gln Pro Ala Met His Thr Val Asn Gly
                245                 250                 255
Tyr Val Asn Arg Ser Leu Pro Gly Leu Ile Gly Cys His Lys Lys Ser
            260                 265                 270
Val Tyr Trp His Val Ile Gly Met Gly Thr Ser Pro Glu Val His Ser
        275                 280                 285
Ile Phe Leu Glu Gly His Thr Phe Leu Val Arg His His Arg Gln Ala
    290                 295                 300
Ser Leu Glu Ile Ser Pro Leu Thr Phe Leu Thr Ala Gln Thr Phe Leu
305                 310                 315                 320
Met Asp Leu Gly Gln Phe Leu Leu Phe Cys His Ile Ser Ser His His
                325                 330                 335
His Gly Gly Met Glu Ala His Val Arg Val Glu Ser Cys Ala Glu Glu
            340                 345                 350
Pro Gln Leu Arg Arg Lys Ala Asp Glu Glu Glu Asp Tyr Asp Asp Asn
        355                 360                 365
Leu Tyr Asp Ser Asp Met Asp Val Val Arg Leu Asp Gly Asp Asp Val
    370                 375                 380
Ser Pro Phe Ile Gln Ile Arg Ser Val Ala Lys Lys His Pro Lys Thr
```

-continued

```
             385                     390                     395                     400
Trp  Val  His  Tyr  Ile  Ser  Ala  Glu  Glu  Asp  Trp  Asp  Tyr  Ala  Pro
                    405                      410                      415

Ala  Val  Pro  Ser  Pro  Ser  Asp  Arg  Ser  Tyr  Lys  Ser  Leu  Tyr  Leu  Asn
                    420                      425                      430

Ser  Gly  Pro  Gln  Arg  Ile  Gly  Arg  Lys  Tyr  Lys  Lys  Ala  Arg  Phe  Val
                    435                      440                      445

Ala  Tyr  Thr  Asp  Val  Thr  Phe  Lys  Thr  Arg  Lys  Ala  Ile  Pro  Tyr  Glu
          450                      455                      460

Ser  Gly  Ile  Leu  Gly  Pro  Leu  Leu  Tyr  Gly  Glu  Val  Gly  Asp  Thr  Leu
465                      470                      475                      480

Leu  Ile  Ile  Phe  Lys  Asn  Lys  Ala  Ser  Arg  Pro  Tyr  Asn  Ile  Tyr  Pro
                    485                      490                      495

His  Gly  Ile  Thr  Asp  Val  Ser  Ala  Leu  His  Pro  Gly  Arg  Leu  Leu  Lys
                    500                      505                      510

Gly  Trp  Lys  His  Leu  Lys  Asp  Met  Pro  Ile  Leu  Pro  Gly  Glu  Thr  Phe
               515                      520                      525

Lys  Tyr  Lys  Trp  Thr  Val  Thr  Val  Glu  Asp  Gly  Pro  Thr  Lys  Ser  Asp
          530                      535                      540

Pro  Arg  Cys  Leu  Thr  Arg  Tyr  Tyr  Ser  Ser  Ser  Ile  Asn  Leu  Glu  Lys
545                      550                      555                      560

Asp  Leu  Ala  Ser  Gly  Leu  Ile  Gly  Pro  Leu  Leu  Ile  Cys  Tyr  Lys  Glu
                    565                      570                      575

Ser  Val  Asp  Gln  Arg  Gly  Asn  Gln  Met  Met  Ser  Asp  Lys  Arg  Asn  Val
                    580                      585                      590

Ile  Leu  Phe  Ser  Val  Phe  Asp  Glu  Asn  Gln  Ser  Trp  Tyr  Leu  Ala  Glu
          595                      600                      605

Asn  Ile  Gln  Arg  Phe  Leu  Pro  Asn  Pro  Asp  Gly  Leu  Gln  Pro  Gln  Asp
610                      615                      620

Pro  Glu  Phe  Gln  Ala  Ser  Asn  Ile  Met  His  Ser  Ile  Asn  Gly  Tyr  Val
625                      630                      635                      640

Phe  Asp  Ser  Leu  Gln  Leu  Ser  Val  Cys  Leu  His  Glu  Val  Ala  Tyr  Trp
                    645                      650                      655

Tyr  Ile  Leu  Ser  Val  Gly  Ala  Gln  Thr  Asp  Phe  Leu  Ser  Val  Phe  Phe
               660                      665                      670

Ser  Gly  Tyr  Thr  Phe  Lys  His  Lys  Met  Val  Tyr  Glu  Asp  Thr  Leu  Thr
          675                      680                      685

Leu  Phe  Pro  Phe  Ser  Gly  Glu  Thr  Val  Phe  Met  Ser  Met  Glu  Asn  Pro
          690                      695                      700

Gly  Leu  Trp  Val  Leu  Gly  Cys  His  Asn  Ser  Asp  Leu  Arg  Asn  Arg  Gly
705                      710                      715                      720

Met  Thr  Ala  Leu  Leu  Lys  Val  Tyr  Ser  Cys  Asp  Arg  Asp  Ile  Gly  Asp
                    725                      730                      735

Tyr  Tyr  Asp  Asn  Thr  Tyr  Glu  Asp  Ile  Pro  Gly  Phe  Leu  Leu  Ser  Gly
               740                      745                      750

Lys  Asn  Val  Ile  Glu  Pro  Arg  Ser  Phe  Ala  Gln  Asn  Ser  Arg  Pro  Pro
          755                      760                      765

Ser  Ala  Ser  Gln  Lys  Gln  Phe  Gln  Thr  Ile  Thr  Ser  Pro  Glu  Asp  Asp
     770                      775                      780

Val  Glu  Leu  Asp  Pro  Gln  Ser  Gly  Glu  Arg  Thr  Gln  Ala  Leu  Glu  Glu
785                      790                      795                      800

Leu  Ser  Val  Pro  Ser  Gly  Asp  Gly  Ser  Met  Leu  Leu  Gly  Gln  Asn  Pro
                    805                      810                      815
```

-continued

```
Ala Pro His Gly Ser Ser Ser Ser Asp Leu Gln Glu Ala Arg Asn Glu
             820                 825                 830
Ala Asp Asp Tyr Leu Pro Gly Ala Arg Glu Arg Asn Thr Ala Pro Ser
835                 840                 845
Ala Ala Ala Arg Leu Arg Pro Glu Leu His His Ala Glu Arg Val
    850                 855                 860
Leu Thr Pro Glu Pro Glu Lys Glu Leu Lys Lys Leu Asp Ser Lys Met
865                 870                 875                 880
Ser Ser Ser Ser Asp Leu Leu Lys Thr Ser Pro Thr Ile Pro Ser Asp
                885                 890                 895
Thr Leu Ser Ala Glu Thr Glu Arg Thr His Ser Leu Gly Pro Pro His
            900                 905                 910
Pro Gln Val Asn Phe Arg Ser Gln Leu Gly Ala Ile Val Leu Gly Lys
            915                 920                 925
Asn Ser Ser His Phe Ile Gly Ala Gly Val Pro Leu Gly Ser Thr Glu
930                 935                 940
Glu Asp His Glu Ser Ser Leu Gly Glu Asn Val Ser Pro Val Glu Ser
945                 950                 955                 960
Asp Gly Ile Phe Glu Lys Glu Arg Ala His Gly Pro Ala Ser Leu Thr
                965                 970                 975
Lys Asp Asp Val Leu Phe Lys Val Asn Ile Ser Leu Val Lys Thr Asn
            980                 985                 990
Lys Ala Arg Val Tyr Leu Lys Thr Asn Arg Lys Ile His Ile Asp Asp
            995                 1000                1005
Ala Ala Leu Leu Thr Glu Asn Arg Ala Ser Ala Thr Phe Met Asp Lys
    1010                1015                1020
Asn Thr Thr Ala Ser Gly Leu Asn His Val Ser Asn Trp Ile Lys Gly
1025                1030                1035                1040
Pro Leu Gly Lys Asn Pro Leu Ser Ser Glu Arg Gly Pro Ser Pro Glu
                1045                1050                1055
Leu Leu Thr Ser Ser Gly Ser Gly Lys Ser Val Lys Gly Gln Ser Ser
            1060                1065                1070
Gly Gln Gly Arg Ile Arg Val Ala Val Glu Glu Glu Glu Leu Ser Lys
            1075                1080                1085
Gly Lys Glu Met Met Leu Pro Asn Ser Glu Leu Thr Phe Leu Thr Asn
1090                1095                1100
Ser Ala Asp Val Gln Gly Asn Asp Thr His Ser Gln Gly Lys Lys Ser
1105                1110                1115                1120
Arg Glu Glu Met Glu Arg Arg Glu Lys Leu Val Gln Glu Lys Val Asp
                1125                1130                1135
Leu Pro Gln Val Tyr Thr Ala Thr Gly Thr Lys Asn Phe Leu Arg Asn
            1140                1145                1150
Ile Phe His Gln Ser Thr Glu Pro Ser Val Glu Gly Phe Asp Gly Gly
        1155                1160                1165
Ser His Ala Pro Val Pro Gln Asp Ser Arg Ser Leu Asn Asp Ser Ala
    1170                1175                1180
Glu Arg Ala Glu Thr His Ile Ala His Phe Ser Ala Ile Arg Glu Glu
1185                1190                1195                1200
Ala Pro Leu Glu Ala Pro Gly Asn Arg Thr Gly Pro Gly Pro Arg Ser
            1205                1210                1215
Ala Val Pro Arg Arg Val Lys Gln Ser Leu Lys Gln Ile Arg Leu Pro
            1220                1225                1230
Leu Glu Glu Ile Lys Pro Glu Arg Gly Val Val Leu Asn Ala Thr Ser
            1235                1240                1245
```

-continued

```
Thr Arg Trp Ser Glu Ser Ser Pro Ile Leu Gln Gly Ala Lys Arg Asn
        1250            1255                1260

Asn Leu Ser Leu Pro Phe Leu Thr Leu Glu Met Ala Gly Gly Gln Gly
1265            1270                1275                1280

Lys Ile Ser Ala Leu Gly Lys Ser Ala Ala Gly Pro Leu Ala Ser Gly
                1285                1290                1295

Lys Leu Glu Lys Ala Val Leu Ser Ser Ala Gly Leu Ser Glu Ala Ser
        1300            1305                1310

Gly Lys Ala Glu Phe Leu Pro Lys Val Arg Val His Arg Glu Asp Leu
        1315            1320                1325

Leu Pro Gln Lys Thr Ser Asn Val Ser Cys Ala His Gly Asp Leu Gly
        1330            1335                1340

Gln Glu Ile Phe Leu Gln Lys Thr Arg Gly Pro Val Asn Leu Asn Lys
1345            1350                1355                1360

Val Asn Arg Pro Gly Arg Thr Pro Ser Lys Leu Leu Gly Pro Pro Met
                1365                1370                1375

Pro Lys Glu Trp Glu Ser Leu Glu Lys Ser Pro Lys Ser Thr Ala Leu
                1380                1385                1390

Arg Thr Lys Asp Ile Ile Ser Leu Pro Leu Asp Arg His Glu Ser Asn
        1395            1400                1405

His Ser Ile Ala Ala Lys Asn Glu Gly Gln Ala Glu Thr Gln Arg Glu
        1410            1415                1420

Ala Ala Trp Thr Lys Gln Gly Gly Pro Gly Arg Leu Cys Ala Pro Lys
1425            1430                1435                1440

Pro Pro Val Leu Arg Arg His Gln Arg Asp Ile Ser Leu Pro Thr Phe
                1445                1450                1455

Gln Pro Glu Glu Asp Lys Met Asp Tyr Asp Asp Ile Phe Ser Thr Glu
                1460                1465                1470

Thr Lys Gly Glu Asp Phe Asp Ile Tyr Gly Glu Asp Glu Asn Gln Asp
                1475                1480                1485

Pro Arg Ser Phe Gln Lys Arg Thr Arg His Tyr Phe Ile Ala Ala Val
        1490            1495                1500

Glu Gln Leu Trp Asp Tyr Gly Met Ser Glu Ser Pro Arg Ala Leu Arg
1505            1510                1515                1520

Asn Arg Ala Gln Asn Gly Glu Val Pro Arg Phe Lys Lys Val Val Phe
                1525                1530                1535

Arg Glu Phe Ala Asp Gly Ser Phe Thr Gln Pro Ser Tyr Arg Gly Glu
                1540                1545                1550

Leu Asn Lys His Leu Gly Leu Leu Gly Pro Tyr Ile Arg Ala Glu Val
                1555                1560                1565

Glu Asp Asn Ile Met Val Thr Phe Lys Asn Gln Ala Ser Arg Pro Tyr
        1570            1575                1580

Ser Phe Tyr Ser Ser Leu Ile Ser Tyr Pro Asp Asp Gln Glu Gln Gly
1585            1590                1595                1600

Ala Glu Pro Arg His Asn Phe Val Gln Pro Asn Glu Thr Arg Thr Tyr
                1605                1610                1615

Phe Trp Lys Val Gln His His Met Ala Pro Thr Glu Asp Glu Phe Asp
                1620                1625                1630

Cys Lys Ala Trp Ala Tyr Phe Ser Asp Val Asp Leu Glu Lys Asp Val
                1635                1640                1645

His Ser Gly Leu Ile Gly Pro Leu Leu Ile Cys Arg Ala Asn Thr Leu
        1650            1655                1660

Asn Ala Ala His Gly Arg Gln Val Thr Val Gln Glu Phe Ala Leu Phe
```

```
                    1665                    1670                    1675                    1680
Phe  Thr  Ile  Phe  Asp  Glu  Thr  Lys  Ser  Trp  Tyr  Phe  Thr  Glu  Asn  Val
                         1685                    1690                    1695

Glu  Arg  Asn  Cys  Arg  Ala  Pro  Cys  His  Leu  Gln  Met  Glu  Asp  Pro  Thr
                1700                    1705                    1710

Leu  Lys  Glu  Asn  Tyr  Arg  Phe  His  Ala  Ile  Asn  Gly  Tyr  Val  Met  Asp
           1715                    1720                    1725

Thr  Leu  Pro  Gly  Leu  Val  Met  Ala  Gln  Asn  Gln  Arg  Ile  Arg  Trp  Tyr
      1730                    1735                    1740

Leu  Leu  Ser  Met  Gly  Ser  Asn  Glu  Asn  Ile  His  Ser  Ile  His  Phe  Ser
1745                    1750                    1755                    1760

Gly  His  Val  Phe  Ser  Val  Arg  Lys  Lys  Glu  Glu  Tyr  Lys  Met  Ala  Val
                1765                    1770                    1775

Tyr  Asn  Leu  Tyr  Pro  Gly  Val  Phe  Glu  Thr  Val  Glu  Met  Leu  Pro  Ser
           1780                    1785                    1790

Lys  Val  Gly  Ile  Trp  Arg  Ile  Glu  Cys  Leu  Ile  Gly  Glu  His  Leu  Gln
                1795                    1800                    1805

Ala  Gly  Met  Ser  Thr  Thr  Phe  Leu  Val  Tyr  Ser  Lys  Glu  Cys  Gln  Ala
      1810                    1815                    1820

Pro  Leu  Gly  Met  Ala  Ser  Gly  Arg  Ile  Arg  Asp  Phe  Gln  Ile  Thr  Ala
1825                    1830                    1835                    1840

Ser  Gly  Gln  Tyr  Gly  Gln  Trp  Ala  Pro  Lys  Leu  Ala  Arg  Leu  His  Tyr
                1845                    1850                    1855

Ser  Gly  Ser  Ile  Asn  Ala  Trp  Ser  Thr  Lys  Asp  Pro  His  Ser  Trp  Ile
                1860                    1865                    1870

Lys  Val  Asp  Leu  Leu  Ala  Pro  Met  Ile  Ile  His  Gly  Ile  Met  Thr  Gln
           1875                    1880                    1885

Gly  Ala  Arg  Gln  Lys  Phe  Ser  Ser  Leu  Tyr  Ile  Ser  Gln  Phe  Ile  Ile
      1890                    1895                    1900

Met  Tyr  Ser  Leu  Asp  Gly  Arg  Asn  Trp  Gln  Ser  Tyr  Arg  Gly  Asn  Ser
1905                    1910                    1915                    1920

Thr  Gly  Thr  Leu  Met  Val  Phe  Phe  Gly  Asn  Val  Asp  Ala  Ser  Gly  Ile
                1925                    1930                    1935

Lys  His  Asn  Ile  Phe  Asn  Pro  Pro  Ile  Val  Ala  Arg  Tyr  Ile  Arg  Leu
                1940                    1945                    1950

His  Pro  Thr  His  Tyr  Ser  Ile  Arg  Ser  Thr  Leu  Arg  Met  Glu  Leu  Met
           1955                    1960                    1965

Gly  Cys  Asp  Leu  Asn  Ser  Cys  Ser  Met  Pro  Leu  Gly  Met  Gln  Asn  Lys
      1970                    1975                    1980

Ala  Ile  Ser  Asp  Ser  Gln  Ile  Thr  Ala  Ser  Ser  His  Leu  Ser  Asn  Ile
1985                    1990                    1995                    2000

Phe  Ala  Thr  Trp  Ser  Pro  Ser  Gln  Ala  Arg  Leu  His  Leu  Gln  Gly  Arg
                2005                    2010                    2015

Thr  Asn  Ala  Trp  Arg  Pro  Arg  Val  Ser  Ser  Ala  Glu  Glu  Trp  Leu  Gln
                2020                    2025                    2030

Val  Asp  Leu  Gln  Lys  Thr  Val  Lys  Val  Thr  Gly  Ile  Thr  Thr  Gln  Gly
           2035                    2040                    2045

Val  Lys  Ser  Leu  Leu  Ser  Ser  Met  Tyr  Val  Lys  Glu  Phe  Leu  Val  Ser
      2050                    2055                    2060

Ser  Ser  Gln  Asp  Gly  Arg  Arg  Trp  Thr  Leu  Phe  Leu  Gln  Asp  Gly  His
2065                    2070                    2075                    2080

Thr  Lys  Val  Phe  Gln  Gly  Asn  Gln  Asp  Ser  Ser  Thr  Pro  Val  Val  Asn
           2085                    2090                    2095
```

| Ala | Leu | Asp | Pro | Pro | Leu | Phe | Thr | Arg | Tyr | Leu | Arg | Ile | His | Pro | Thr |
|---|---|---|---|---|---|---|---|---|---|---|---|---|---|---|---|
|   |   |   | 2100 |   |   |   | 2105 |   |   |   |   |   | 2110 |   |   |

| Ser | Trp | Ala | Gln | His | Ile | Ala | Leu | Arg | Leu | Glu | Val | Leu | Gly | Cys | Glu |
|---|---|---|---|---|---|---|---|---|---|---|---|---|---|---|---|
|   |   |   | 2115 |   |   |   | 2120 |   |   |   |   |   | 2125 |   |   |

| Ala | Gln | Asp | Leu | Tyr |
|---|---|---|---|---|
|   |   |   | 2130 |   |

( 2 ) INFORMATION FOR SEQ ID NO:38:

( i ) SEQUENCE CHARACTERISTICS:
      ( A ) LENGTH: 4334 base pairs
      ( B ) TYPE: nucleic acid
      ( C ) STRANDEDNESS: double
      ( D ) TOPOLOGY: Not Relevant ( i i ) MOLECULE TYPE: cDNA to mRNA ( i i i ) HYPOTHETICAL: NO ( v i ) ORIGINAL SOURCE:
      ( C ) INDIVIDUAL ISOLATE: Factor VIII lacking B domain ( i x ) FEATURE:
      ( A ) NAME/KEY: CDS
      ( B ) LOCATION: 3..4334

( x i ) SEQUENCE DESCRIPTION: SEQ ID NO:38:

```
GA ATG CAG CTA GAG CTC TCC ACC TGT GTC TTT CTG TGT CTC TTG CCA        47
   Met Gln Leu Glu Leu Ser Thr Cys Val Phe Leu Cys Leu Leu Pro
    1           5                  10                  15

CTC GGC TTT AGT GCC ATC AGG AGA TAC TAC CTG GGC GCA GTG GAA CTG        95
Leu Gly Phe Ser Ala Ile Arg Arg Tyr Tyr Leu Gly Ala Val Glu Leu
             20                  25                  30

TCC TGG GAC TAC CGG CAA AGT GAA CTC CTC CGT GAG CTG CAC GTG GAC       143
Ser Trp Asp Tyr Arg Gln Ser Glu Leu Leu Arg Glu Leu His Val Asp
                 35                  40                  45

ACC AGA TTT CCT GCT ACA GCG CCA GGA GCT CTT CCG TTG GGC CCG TCA       191
Thr Arg Phe Pro Ala Thr Ala Pro Gly Ala Leu Pro Leu Gly Pro Ser
             50                  55                  60

GTC CTG TAC AAA AAG ACT GTG TTC GTA GAG TTC ACG GAT CAA CTT TTC       239
Val Leu Tyr Lys Lys Thr Val Phe Val Glu Phe Thr Asp Gln Leu Phe
 65                  70                  75

AGC GTT GCC AGG CCC AGG CCA CCA TGG ATG GGT CTG CTG GGT CCT ACC       287
Ser Val Ala Arg Pro Arg Pro Pro Trp Met Gly Leu Leu Gly Pro Thr
 80                  85                  90                  95

ATC CAG GCT GAG GTT TAC GAC ACG GTG GTC GTT ACC CTG AAG AAC ATG       335
Ile Gln Ala Glu Val Tyr Asp Thr Val Val Val Thr Leu Lys Asn Met
                 100                 105                 110

GCT TCT CAT CCC GTT AGT CTT CAC GCT GTC GGC GTC TCC TTC TGG AAA       383
Ala Ser His Pro Val Ser Leu His Ala Val Gly Val Ser Phe Trp Lys
             115                 120                 125

TCT TCC GAA GGC GCT GAA TAT GAG GAT CAC ACC AGC CAA AGG GAG AAG       431
Ser Ser Glu Gly Ala Glu Tyr Glu Asp His Thr Ser Gln Arg Glu Lys
         130                 135                 140

GAA GAC GAT AAA GTC CTT CCC GGT AAA AGC CAA ACC TAC GTC TGG CAG       479
Glu Asp Asp Lys Val Leu Pro Gly Lys Ser Gln Thr Tyr Val Trp Gln
     145                 150                 155

GTC CTG AAA GAA AAT GGT CCA ACA GCC TCT GAC CCA CCA TGT CTC ACC       527
Val Leu Lys Glu Asn Gly Pro Thr Ala Ser Asp Pro Pro Cys Leu Thr
160                 165                 170                 175

TAC TCA TAC CTG TCT CAC GTG GAC CTG GTG AAA GAC CTG AAT TCG GGC       575
Tyr Ser Tyr Leu Ser His Val Asp Leu Val Lys Asp Leu Asn Ser Gly
                 180                 185                 190

CTC ATT GGA GCC CTG CTG GTT TGT AGA GAA GGG AGT CTG ACC AGA GAA       623
```

```
Leu Ile Gly Ala Leu Leu Val Cys Arg Glu Gly Ser Leu Thr Arg Glu
        195             200                 205

AGG ACC CAG AAC CTG CAC GAA TTT GTA CTA CTT TTT GCT GTC TTT GAT        671
Arg Thr Gln Asn Leu His Glu Phe Val Leu Leu Phe Ala Val Phe Asp
        210             215                 220

GAA GGG AAA AGT TGG CAC TCA GCA AGA AAT GAC TCC TGG ACA CGG GCC        719
Glu Gly Lys Ser Trp His Ser Ala Arg Asn Asp Ser Trp Thr Arg Ala
        225             230                 235

ATG GAT CCC GCA CCT GCC AGG GCC CAG CCT GCA ATG CAC ACA GTC AAT        767
Met Asp Pro Ala Pro Ala Arg Ala Gln Pro Ala Met His Thr Val Asn
240             245                 250             255

GGC TAT GTC AAC AGG TCT CTG CCA GGT CTG ATC GGA TGT CAT AAG AAA        815
Gly Tyr Val Asn Arg Ser Leu Pro Gly Leu Ile Gly Cys His Lys Lys
                260             265                 270

TCA GTC TAC TGG CAC GTG ATT GGA ATG GGC ACC AGC CCG GAA GTG CAC        863
Ser Val Tyr Trp His Val Ile Gly Met Gly Thr Ser Pro Glu Val His
            275             280             285

TCC ATT TTT CTT GAA GGC CAC ACG TTT CTC GTG AGG CAC CAT CGC CAG        911
Ser Ile Phe Leu Glu Gly His Thr Phe Leu Val Arg His His Arg Gln
        290             295                 300

GCT TCC TTG GAG ATC TCG CCA CTA ACT TTC CTC ACT GCT CAG ACA TTC        959
Ala Ser Leu Glu Ile Ser Pro Leu Thr Phe Leu Thr Ala Gln Thr Phe
        305             310                 315

CTG ATG GAC CTT GGC CAG TTC CTA CTG TTT TGT CAT ATC TCT TCC CAC       1007
Leu Met Asp Leu Gly Gln Phe Leu Leu Phe Cys His Ile Ser Ser His
320             325                 330             335

CAC CAT GGT GGC ATG GAG GCT CAC GTC AGA GTA GAA AGC TGC GCC GAG       1055
His His Gly Gly Met Glu Ala His Val Arg Val Glu Ser Cys Ala Glu
                340             345                 350

GAG CCC CAG CTG CGG AGG AAA GCT GAT GAA GAG GAA GAT TAT GAT GAC       1103
Glu Pro Gln Leu Arg Arg Lys Ala Asp Glu Glu Glu Asp Tyr Asp Asp
            355                 360             365

AAT TTG TAC GAC TCG GAC ATG GAC GTG GTC CGG CTC GAT GGT GAC GAC       1151
Asn Leu Tyr Asp Ser Asp Met Asp Val Val Arg Leu Asp Gly Asp Asp
        370             375                 380

GTG TCT CCC TTT ATC CAA ATC CGC TCG GTT GCC AAG AAG CAT CCC AAA       1199
Val Ser Pro Phe Ile Gln Ile Arg Ser Val Ala Lys Lys His Pro Lys
        385             390                 395

ACC TGG GTG CAC TAC ATC TCT GCA GAG GAG GAG GAC TGG GAC TAC GCC       1247
Thr Trp Val His Tyr Ile Ser Ala Glu Glu Glu Asp Trp Asp Tyr Ala
400             405                 410             415

CCC GCG GTC CCC AGC CCC AGT GAC AGA AGT TAT AAA AGT CTC TAC TTG       1295
Pro Ala Val Pro Ser Pro Ser Asp Arg Ser Tyr Lys Ser Leu Tyr Leu
                420             425                 430

AAC AGT GGT CCT CAG CGA ATT GGT AGG AAA TAC AAA AAA GCT CGA TTC       1343
Asn Ser Gly Pro Gln Arg Ile Gly Arg Lys Tyr Lys Lys Ala Arg Phe
            435                 440             445

GTC GCT TAC ACG GAT GTA ACA TTT AAG ACT CGT AAA GCT ATT CCG TAT       1391
Val Ala Tyr Thr Asp Val Thr Phe Lys Thr Arg Lys Ala Ile Pro Tyr
        450             455                 460

GAA TCA GGA ATC CTG GGA CCT TTA CTT TAT GGA GAA GTT GGA GAC ACA       1439
Glu Ser Gly Ile Leu Gly Pro Leu Leu Tyr Gly Glu Val Gly Asp Thr
        465             470                 475

CTT TTG ATT ATA TTT AAG AAT AAA GCG AGC CGA CCA TAT AAC ATC TAC       1487
Leu Leu Ile Ile Phe Lys Asn Lys Ala Ser Arg Pro Tyr Asn Ile Tyr
480             485                 490             495

CCT CAT GGA ATC ACT GAT GTC AGC GCT TTG CAC CCA GGG AGA CTT CTA       1535
Pro His Gly Ile Thr Asp Val Ser Ala Leu His Pro Gly Arg Leu Leu
                500             505                 510

AAA GGT TGG AAA CAT TTG AAA GAC ATG CCA ATT CTG CCA GGA GAG ACT       1583
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Lys | Gly | Trp | Lys | His | Leu | Lys | Asp | Met | Pro | Ile | Leu | Pro | Gly | Glu | Thr  |
|     |     |     | 515 |     |     |     | 520 |     |     |     |     | 525 |     |     |      |
| TTC | AAG | TAT | AAA | TGG | ACA | GTG | ACT | GTG | GAA | GAT | GGG | CCA | ACC | AAG | TCC  | 1631 |
| Phe | Lys | Tyr | Lys | Trp | Thr | Val | Thr | Val | Glu | Asp | Gly | Pro | Thr | Lys | Ser  |
|     |     | 530 |     |     |     | 535 |     |     |     |     | 540 |     |     |     |      |
| GAT | CCT | CGG | TGC | CTG | ACC | CGC | TAC | TAC | TCG | AGC | TCC | ATT | AAT | CTA | GAG  | 1679 |
| Asp | Pro | Arg | Cys | Leu | Thr | Arg | Tyr | Tyr | Ser | Ser | Ser | Ile | Asn | Leu | Glu  |
|     | 545 |     |     |     |     | 550 |     |     |     |     | 555 |     |     |     |      |
| AAA | GAT | CTG | GCT | TCG | GGA | CTC | ATT | GGC | CCT | CTC | CTC | ATC | TGC | TAC | AAA  | 1727 |
| Lys | Asp | Leu | Ala | Ser | Gly | Leu | Ile | Gly | Pro | Leu | Leu | Ile | Cys | Tyr | Lys  |
| 560 |     |     |     |     | 565 |     |     |     |     | 570 |     |     |     |     | 575  |
| GAA | TCT | GTA | GAC | CAA | AGA | GGA | AAC | CAG | ATG | ATG | TCA | GAC | AAG | AGA | AAC  | 1775 |
| Glu | Ser | Val | Asp | Gln | Arg | Gly | Asn | Gln | Met | Met | Ser | Asp | Lys | Arg | Asn  |
|     |     |     |     | 580 |     |     |     |     | 585 |     |     |     |     | 590 |      |
| GTC | ATC | CTG | TTT | TCT | GTA | TTC | GAT | GAG | AAT | CAA | AGC | TGG | TAC | CTC | GCA  | 1823 |
| Val | Ile | Leu | Phe | Ser | Val | Phe | Asp | Glu | Asn | Gln | Ser | Trp | Tyr | Leu | Ala  |
|     |     |     | 595 |     |     |     |     | 600 |     |     |     |     | 605 |     |      |
| GAG | AAT | ATT | CAG | CGC | TTC | CTC | CCC | AAT | CCG | GAT | GGA | TTA | CAG | CCC | CAG  | 1871 |
| Glu | Asn | Ile | Gln | Arg | Phe | Leu | Pro | Asn | Pro | Asp | Gly | Leu | Gln | Pro | Gln  |
|     |     | 610 |     |     |     |     | 615 |     |     |     |     | 620 |     |     |      |
| GAT | CCA | GAG | TTC | CAA | GCT | TCT | AAC | ATC | ATG | CAC | AGC | ATC | AAT | GGC | TAT  | 1919 |
| Asp | Pro | Glu | Phe | Gln | Ala | Ser | Asn | Ile | Met | His | Ser | Ile | Asn | Gly | Tyr  |
|     | 625 |     |     |     |     | 630 |     |     |     |     | 635 |     |     |     |      |
| GTT | TTT | GAT | AGC | TTG | CAG | CTG | TCG | GTT | TGT | TTG | CAC | GAG | GTG | GCA | TAC  | 1967 |
| Val | Phe | Asp | Ser | Leu | Gln | Leu | Ser | Val | Cys | Leu | His | Glu | Val | Ala | Tyr  |
| 640 |     |     |     |     | 645 |     |     |     |     | 650 |     |     |     |     | 655  |
| TGG | TAC | ATT | CTA | AGT | GTT | GGA | GCA | CAG | ACG | GAC | TTC | CTC | TCC | GTC | TTC  | 2015 |
| Trp | Tyr | Ile | Leu | Ser | Val | Gly | Ala | Gln | Thr | Asp | Phe | Leu | Ser | Val | Phe  |
|     |     |     |     | 660 |     |     |     |     | 665 |     |     |     |     | 670 |      |
| TTC | TCT | GGC | TAC | ACC | TTC | AAA | CAC | AAA | ATG | GTC | TAT | GAA | GAC | ACA | CTC  | 2063 |
| Phe | Ser | Gly | Tyr | Thr | Phe | Lys | His | Lys | Met | Val | Tyr | Glu | Asp | Thr | Leu  |
|     |     |     | 675 |     |     |     |     | 680 |     |     |     |     | 685 |     |      |
| ACC | CTG | TTC | CCC | TTC | TCA | GGA | GAA | ACG | GTC | TTC | ATG | TCA | ATG | GAA | AAC  | 2111 |
| Thr | Leu | Phe | Pro | Phe | Ser | Gly | Glu | Thr | Val | Phe | Met | Ser | Met | Glu | Asn  |
|     |     | 690 |     |     |     |     | 695 |     |     |     |     | 700 |     |     |      |
| CCA | GGT | CTC | TGG | GTC | CTA | GGG | TGC | CAC | AAC | TCA | GAC | TTG | CGG | AAC | AGA  | 2159 |
| Pro | Gly | Leu | Trp | Val | Leu | Gly | Cys | His | Asn | Ser | Asp | Leu | Arg | Asn | Arg  |
|     | 705 |     |     |     |     | 710 |     |     |     |     | 715 |     |     |     |      |
| GGG | ATG | ACA | GCC | TTA | CTG | AAG | GTG | TAT | AGT | TGT | GAC | AGG | GAC | ATT | GGT  | 2207 |
| Gly | Met | Thr | Ala | Leu | Leu | Lys | Val | Tyr | Ser | Cys | Asp | Arg | Asp | Ile | Gly  |
| 720 |     |     |     |     | 725 |     |     |     |     | 730 |     |     |     |     | 735  |
| GAT | TAT | TAT | GAC | AAC | ACT | TAT | GAA | GAT | ATT | CCA | GGC | TTC | TTG | CTG | AGT  | 2255 |
| Asp | Tyr | Tyr | Asp | Asn | Thr | Tyr | Glu | Asp | Ile | Pro | Gly | Phe | Leu | Leu | Ser  |
|     |     |     |     | 740 |     |     |     |     | 745 |     |     |     |     | 750 |      |
| GGA | AAG | AAT | GTC | ATT | GAA | CCC | AGA | GAC | ATA | AGC | CTT | CCT | ACT | TTT | CAG  | 2303 |
| Gly | Lys | Asn | Val | Ile | Glu | Pro | Arg | Asp | Ile | Ser | Leu | Pro | Thr | Phe | Gln  |
|     |     |     | 755 |     |     |     |     | 760 |     |     |     |     | 765 |     |      |
| CCG | GAG | GAA | GAC | AAA | ATG | GAC | TAT | GAT | GAT | ATC | TTC | TCA | ACT | GAA | ACG  | 2351 |
| Pro | Glu | Glu | Asp | Lys | Met | Asp | Tyr | Asp | Asp | Ile | Phe | Ser | Thr | Glu | Thr  |
|     |     | 770 |     |     |     |     | 775 |     |     |     |     | 780 |     |     |      |
| AAG | GGA | GAA | GAT | TTT | GAC | ATT | TAC | GGT | GAG | GAT | GAA | AAT | CAG | GAC | CCT  | 2399 |
| Lys | Gly | Glu | Asp | Phe | Asp | Ile | Tyr | Gly | Glu | Asp | Glu | Asn | Gln | Asp | Pro  |
|     | 785 |     |     |     |     | 790 |     |     |     |     | 795 |     |     |     |      |
| CGC | AGC | TTT | CAG | AAG | AGA | ACC | CGA | CAC | TAT | TTC | ATT | GCT | GCG | GTG | GAG  | 2447 |
| Arg | Ser | Phe | Gln | Lys | Arg | Thr | Arg | His | Tyr | Phe | Ile | Ala | Ala | Val | Glu  |
| 800 |     |     |     |     | 805 |     |     |     |     | 810 |     |     |     |     | 815  |
| CAG | CTC | TGG | GAT | TAC | GGG | ATG | AGC | GAA | TCC | CCC | CGG | GCG | CTA | AGA | AAC  | 2495 |
| Gln | Leu | Trp | Asp | Tyr | Gly | Met | Ser | Glu | Ser | Pro | Arg | Ala | Leu | Arg | Asn  |
|     |     |     |     | 820 |     |     |     |     | 825 |     |     |     |     | 830 |      |
| AGG | GCT | CAG | AAC | GGA | GAG | GTG | CCT | CGG | TTC | AAG | AAG | GTG | GTC | TTC | CGG  | 2543 |

| | | | | | | | | | | | | | | | | |
|---|---|---|---|---|---|---|---|---|---|---|---|---|---|---|---|---|
| Arg | Ala | Gln | Asn | Gly | Glu | Val | Pro | Arg | Phe | Lys | Lys | Val | Val | Phe | Arg | |
| | | | 835 | | | | 840 | | | | | 845 | | | | |
| GAA | TTT | GCT | GAC | GGC | TCC | TTC | ACG | CAG | CCG | TCG | TAC | CGC | GGG | GAA | CTC | 2591 |
| Glu | Phe | Ala | Asp | Gly | Ser | Phe | Thr | Gln | Pro | Ser | Tyr | Arg | Gly | Glu | Leu | |
| | | 850 | | | | 855 | | | | | 860 | | | | | |
| AAC | AAA | CAC | TTG | GGG | CTC | TTG | GGA | CCC | TAC | ATC | AGA | GCG | GAA | GTT | GAA | 2639 |
| Asn | Lys | His | Leu | Gly | Leu | Leu | Gly | Pro | Tyr | Ile | Arg | Ala | Glu | Val | Glu | |
| | 865 | | | | | 870 | | | | | 875 | | | | | |
| GAC | AAC | ATC | ATG | GTA | ACT | TTC | AAA | AAC | CAG | GCG | TCT | CGT | CCC | TAT | TCC | 2687 |
| Asp | Asn | Ile | Met | Val | Thr | Phe | Lys | Asn | Gln | Ala | Ser | Arg | Pro | Tyr | Ser | |
| 880 | | | | | 885 | | | | | 890 | | | | | 895 | |
| TTC | TAC | TCG | AGC | CTT | ATT | TCT | TAT | CCG | GAT | GAT | CAG | GAG | CAA | GGG | GCA | 2735 |
| Phe | Tyr | Ser | Ser | Leu | Ile | Ser | Tyr | Pro | Asp | Asp | Gln | Glu | Gln | Gly | Ala | |
| | | | | 900 | | | | | 905 | | | | | 910 | | |
| GAA | CCT | CGA | CAC | AAC | TTC | GTC | CAG | CCA | AAT | GAA | ACC | AGA | ACT | TAC | TTT | 2783 |
| Glu | Pro | Arg | His | Asn | Phe | Val | Gln | Pro | Asn | Glu | Thr | Arg | Thr | Tyr | Phe | |
| | | | 915 | | | | 920 | | | | | 925 | | | | |
| TGG | AAA | GTG | CAG | CAT | CAC | ATG | GCA | CCC | ACA | GAA | GAC | GAG | TTT | GAC | TGC | 2831 |
| Trp | Lys | Val | Gln | His | His | Met | Ala | Pro | Thr | Glu | Asp | Glu | Phe | Asp | Cys | |
| | | 930 | | | | 935 | | | | | 940 | | | | | |
| AAA | GCC | TGG | GCC | TAC | TTT | TCT | GAT | GTT | GAC | CTG | GAA | AAA | GAT | GTG | CAC | 2879 |
| Lys | Ala | Trp | Ala | Tyr | Phe | Ser | Asp | Val | Asp | Leu | Glu | Lys | Asp | Val | His | |
| | 945 | | | | | 950 | | | | | 955 | | | | | |
| TCA | GGC | TTG | ATC | GGC | CCC | CTT | CTG | ATC | TGC | CGC | GCC | AAC | ACC | TTG | AAC | 2927 |
| Ser | Gly | Leu | Ile | Gly | Pro | Leu | Leu | Ile | Cys | Arg | Ala | Asn | Thr | Leu | Asn | |
| 960 | | | | | 965 | | | | | 970 | | | | | 975 | |
| GCT | GCT | CAC | GGT | AGA | CAA | GTG | ACC | GTG | CAA | GAA | TTT | GCT | CTG | TTT | TTC | 2975 |
| Ala | Ala | His | Gly | Arg | Gln | Val | Thr | Val | Gln | Glu | Phe | Ala | Leu | Phe | Phe | |
| | | | | 980 | | | | | 985 | | | | | 990 | | |
| ACT | ATT | TTT | GAT | GAG | ACA | AAG | AGC | TGG | TAC | TTC | ACT | GAA | AAT | GTG | GAA | 3023 |
| Thr | Ile | Phe | Asp | Glu | Thr | Lys | Ser | Trp | Tyr | Phe | Thr | Glu | Asn | Val | Glu | |
| | | | 995 | | | | | 1000 | | | | | 1005 | | | |
| AGG | AAC | TGC | CGG | GCC | CCC | TGC | CAC | CTG | CAG | ATG | GAG | GAC | CCC | ACT | CTG | 3071 |
| Arg | Asn | Cys | Arg | Ala | Pro | Cys | His | Leu | Gln | Met | Glu | Asp | Pro | Thr | Leu | |
| | | 1010 | | | | 1015 | | | | | 1020 | | | | | |
| AAA | GAA | AAC | TAT | CGC | TTC | CAT | GCA | ATC | AAT | GGC | TAT | GTG | ATG | GAT | ACA | 3119 |
| Lys | Glu | Asn | Tyr | Arg | Phe | His | Ala | Ile | Asn | Gly | Tyr | Val | Met | Asp | Thr | |
| | 1025 | | | | | 1030 | | | | | 1035 | | | | | |
| CTC | CCT | GGC | TTA | GTA | ATG | GCT | CAG | AAT | CAA | AGG | ATC | CGA | TGG | TAT | CTG | 3167 |
| Leu | Pro | Gly | Leu | Val | Met | Ala | Gln | Asn | Gln | Arg | Ile | Arg | Trp | Tyr | Leu | |
| 1040 | | | | | 1045 | | | | | 1050 | | | | | 1055 | |
| CTC | AGC | ATG | GGC | AGC | AAT | GAA | AAT | ATC | CAT | TCG | ATT | CAT | TTT | AGC | GGA | 3215 |
| Leu | Ser | Met | Gly | Ser | Asn | Glu | Asn | Ile | His | Ser | Ile | His | Phe | Ser | Gly | |
| | | | | 1060 | | | | | 1065 | | | | | 1070 | | |
| CAC | GTG | TTC | AGT | GTA | CGG | AAA | AAG | GAG | GAG | TAT | AAA | ATG | GCC | GTG | TAC | 3263 |
| His | Val | Phe | Ser | Val | Arg | Lys | Lys | Glu | Glu | Tyr | Lys | Met | Ala | Val | Tyr | |
| | | | 1075 | | | | | 1080 | | | | | 1085 | | | |
| AAT | CTC | TAT | CCG | GGT | GTC | TTT | GAG | ACA | GTG | GAA | ATG | CTA | CCG | TCC | AAA | 3311 |
| Asn | Leu | Tyr | Pro | Gly | Val | Phe | Glu | Thr | Val | Glu | Met | Leu | Pro | Ser | Lys | |
| | | | 1090 | | | | | 1095 | | | | | 1100 | | | |
| GTT | GGA | ATT | TGG | CGA | ATA | GAA | TGC | CTG | ATT | GGC | GAG | CAC | CTG | CAA | GCT | 3359 |
| Val | Gly | Ile | Trp | Arg | Ile | Glu | Cys | Leu | Ile | Gly | Glu | His | Leu | Gln | Ala | |
| | | | 1105 | | | | | 1110 | | | | | 1115 | | | |
| GGG | ATG | AGC | ACG | ACT | TTC | CTG | GTG | TAC | AGC | AAG | GAG | TGT | CAG | GCT | CCA | 3407 |
| Gly | Met | Ser | Thr | Thr | Phe | Leu | Val | Tyr | Ser | Lys | Glu | Cys | Gln | Ala | Pro | |
| 1120 | | | | | 1125 | | | | | 1130 | | | | | 1135 | |
| CTG | GGA | ATG | GCT | TCT | GGA | CGC | ATT | AGA | GAT | TTT | CAG | ATC | ACA | GCT | TCA | 3455 |
| Leu | Gly | Met | Ala | Ser | Gly | Arg | Ile | Arg | Asp | Phe | Gln | Ile | Thr | Ala | Ser | |
| | | | | 1140 | | | | | 1145 | | | | | 1150 | | |
| GGA | CAG | TAT | GGA | CAG | TGG | GCC | CCA | AAG | CTG | GCC | AGA | CTT | CAT | TAT | TCC | 3503 |

```
Gly  Gln  Tyr  Gly  Gln  Trp  Ala  Pro  Lys  Leu  Ala  Arg  Leu  His  Tyr  Ser
               1155                    1160                    1165

GGA  TCA  ATC  AAT  GCC  TGG  AGC  ACC  AAG  GAT  CCC  CAC  TCC  TGG  ATC  AAG     3551
Gly  Ser  Ile  Asn  Ala  Trp  Ser  Thr  Lys  Asp  Pro  His  Ser  Trp  Ile  Lys
               1170                    1175                    1180

GTG  GAT  CTG  TTG  GCA  CCA  ATG  ATC  ATT  CAC  GGC  ATC  ATG  ACC  CAG  GGT     3599
Val  Asp  Leu  Leu  Ala  Pro  Met  Ile  Ile  His  Gly  Ile  Met  Thr  Gln  Gly
               1185                    1190                    1195

GCC  CGT  CAG  AAG  TTT  TCC  AGC  CTC  TAC  ATC  TCC  CAG  TTT  ATC  ATC  ATG     3647
Ala  Arg  Gln  Lys  Phe  Ser  Ser  Leu  Tyr  Ile  Ser  Gln  Phe  Ile  Ile  Met
1200                 1205                    1210                         1215

TAC  AGT  CTT  GAC  GGG  AGG  AAC  TGG  CAG  AGT  TAC  CGA  GGG  AAT  TCC  ACG     3695
Tyr  Ser  Leu  Asp  Gly  Arg  Asn  Trp  Gln  Ser  Tyr  Arg  Gly  Asn  Ser  Thr
                    1220                    1225                    1230

GGC  ACC  TTA  ATG  GTC  TTC  TTT  GGC  AAT  GTG  GAC  GCA  TCT  GGG  ATT  AAA     3743
Gly  Thr  Leu  Met  Val  Phe  Phe  Gly  Asn  Val  Asp  Ala  Ser  Gly  Ile  Lys
               1235                    1240                    1245

CAC  AAT  ATT  TTT  AAC  CCT  CCG  ATT  GTG  GCT  CGG  TAC  ATC  CGT  TTG  CAC     3791
His  Asn  Ile  Phe  Asn  Pro  Pro  Ile  Val  Ala  Arg  Tyr  Ile  Arg  Leu  His
               1250                    1255                    1260

CCA  ACA  CAT  TAC  AGC  ATC  CGC  AGC  ACT  CTT  CGC  ATG  GAG  TTG  ATG  GGC     3839
Pro  Thr  His  Tyr  Ser  Ile  Arg  Ser  Thr  Leu  Arg  Met  Glu  Leu  Met  Gly
               1265                    1270                    1275

TGT  GAT  TTA  AAC  AGT  TGC  AGC  ATG  CCC  CTG  GGA  ATG  CAG  AAT  AAA  GCG     3887
Cys  Asp  Leu  Asn  Ser  Cys  Ser  Met  Pro  Leu  Gly  Met  Gln  Asn  Lys  Ala
1280                 1285                    1290                         1295

ATA  TCA  GAC  TCA  CAG  ATC  ACG  GCC  TCC  TCC  CAC  CTA  AGC  AAT  ATA  TTT     3935
Ile  Ser  Asp  Ser  Gln  Ile  Thr  Ala  Ser  Ser  His  Leu  Ser  Asn  Ile  Phe
                    1300                    1305                    1310

GCC  ACC  TGG  TCT  CCT  TCA  CAA  GCC  CGA  CTT  CAC  CTC  CAG  GGG  CGG  ACG     3983
Ala  Thr  Trp  Ser  Pro  Ser  Gln  Ala  Arg  Leu  His  Leu  Gln  Gly  Arg  Thr
               1315                    1320                    1325

AAT  GCC  TGG  CGA  CCC  CGG  GTG  AGC  AGC  GCA  GAG  GAG  TGG  CTG  CAG  GTG     4031
Asn  Ala  Trp  Arg  Pro  Arg  Val  Ser  Ser  Ala  Glu  Glu  Trp  Leu  Gln  Val
               1330                    1335                    1340

GAC  CTG  CAG  AAG  ACG  GTG  AAG  GTC  ACA  GGC  ATC  ACC  ACC  CAG  GGC  GTG     4079
Asp  Leu  Gln  Lys  Thr  Val  Lys  Val  Thr  Gly  Ile  Thr  Thr  Gln  Gly  Val
               1345                    1350                    1355

AAG  TCC  CTG  CTC  AGC  AGC  ATG  TAT  GTG  AAG  GAG  TTC  CTC  GTG  TCC  AGT     4127
Lys  Ser  Leu  Leu  Ser  Ser  Met  Tyr  Val  Lys  Glu  Phe  Leu  Val  Ser  Ser
1360                 1365                    1370                         1375

AGT  CAG  GAC  GGC  CGC  CGC  TGG  ACC  CTG  TTT  CTT  CAG  GAC  GGC  CAC  ACG     4175
Ser  Gln  Asp  Gly  Arg  Arg  Trp  Thr  Leu  Phe  Leu  Gln  Asp  Gly  His  Thr
               1380                    1385                    1390

AAG  GTT  TTT  CAG  GGC  AAT  CAG  GAC  TCC  TCC  ACC  CCC  GTG  GTG  AAC  GCT     4223
Lys  Val  Phe  Gln  Gly  Asn  Gln  Asp  Ser  Ser  Thr  Pro  Val  Val  Asn  Ala
               1395                    1400                    1405

CTG  GAC  CCC  CCG  CTG  TTC  ACG  CGC  TAC  CTG  AGG  ATC  CAC  CCC  ACG  AGC     4271
Leu  Asp  Pro  Pro  Leu  Phe  Thr  Arg  Tyr  Leu  Arg  Ile  His  Pro  Thr  Ser
               1410                    1415                    1420

TGG  GCG  CAG  CAC  ATC  GCC  CTG  AGG  CTC  GAG  GTT  CTA  GGA  TGT  GAG  GCA     4319
Trp  Ala  Gln  His  Ile  Ala  Leu  Arg  Leu  Glu  Val  Leu  Gly  Cys  Glu  Ala
               1425                    1430                    1435

CAG  GAT  CTC  TAC  TGA                                                            4334
Gln  Asp  Leu  Tyr  *
1440
```

( 2 ) INFORMATION FOR SEQ ID NO:39:

( i ) SEQUENCE CHARACTERISTICS:
        ( A ) LENGTH: 1443 amino acids (B) TYPE: amino acid
(D) TOPOLOGY: linear (ii) MOLECULE TYPE: protein (xi) SEQUENCE DESCRIPTION: SEQ ID NO:39:

```
Met Gln Leu Glu Leu Ser Thr Cys Val Phe Leu Cys Leu Leu Pro Leu
 1               5                  10                  15
Gly Phe Ser Ala Ile Arg Arg Tyr Tyr Leu Gly Ala Val Glu Leu Ser
                20                  25                  30
Trp Asp Tyr Arg Gln Ser Glu Leu Leu Arg Glu Leu His Val Asp Thr
            35                  40                  45
Arg Phe Pro Ala Thr Ala Pro Gly Ala Leu Pro Leu Gly Pro Ser Val
        50                  55                  60
Leu Tyr Lys Lys Thr Val Phe Val Glu Phe Thr Asp Gln Leu Phe Ser
 65                  70                  75                  80
Val Ala Arg Pro Arg Pro Pro Trp Met Gly Leu Leu Gly Pro Thr Ile
                85                  90                  95
Gln Ala Glu Val Tyr Asp Thr Val Val Val Thr Leu Lys Asn Met Ala
                100                 105                 110
Ser His Pro Val Ser Leu His Ala Val Gly Val Ser Phe Trp Lys Ser
            115                 120                 125
Ser Glu Gly Ala Glu Tyr Glu Asp His Thr Ser Gln Arg Glu Lys Glu
        130                 135                 140
Asp Asp Lys Val Leu Pro Gly Lys Ser Gln Thr Tyr Val Trp Gln Val
145                 150                 155                 160
Leu Lys Glu Asn Gly Pro Thr Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Thr Arg Glu Arg
        195                 200                 205
Thr Gln Asn Leu His Glu Phe Val Leu Leu Phe Ala Val Phe Asp Glu
210                 215                 220
Gly Lys Ser Trp His Ser Ala Arg Asn Asp Ser Trp Thr Arg Ala Met
225                 230                 235                 240
Asp Pro Ala Pro Ala Arg Ala Gln Pro Ala Met His Thr Val Asn Gly
                245                 250                 255
Tyr Val Asn Arg Ser Leu Pro Gly Leu Ile Gly Cys His Lys Lys Ser
            260                 265                 270
Val Tyr Trp His Val Ile Gly Met Gly Thr Ser Pro Glu Val His Ser
        275                 280                 285
Ile Phe Leu Glu Gly His Thr Phe Leu Val Arg His His Arg Gln Ala
290                 295                 300
Ser Leu Glu Ile Ser Pro Leu Thr Phe Leu Thr Ala Gln Thr Phe Leu
305                 310                 315                 320
Met Asp Leu Gly Gln Phe Leu Leu Phe Cys His Ile Ser Ser His His
                325                 330                 335
His Gly Gly Met Glu Ala His Val Arg Val Glu Ser Cys Ala Glu Glu
            340                 345                 350
Pro Gln Leu Arg Arg Lys Ala Asp Glu Glu Glu Asp Tyr Asp Asp Asn
        355                 360                 365
Leu Tyr Asp Ser Asp Met Asp Val Val Arg Leu Asp Gly Asp Asp Val
370                 375                 380
Ser Pro Phe Ile Gln Ile Arg Ser Val Ala Lys Lys His Pro Lys Thr
```

```
385                    390                    395                    400
Trp Val His Tyr Ile Ser Ala Glu Glu Asp Trp Asp Tyr Ala Pro
            405                    410                    415
Ala Val Pro Ser Pro Ser Asp Arg Ser Tyr Lys Ser Leu Tyr Leu Asn
            420                    425                    430
Ser Gly Pro Gln Arg Ile Gly Arg Lys Tyr Lys Lys Ala Arg Phe Val
            435                    440                    445
Ala Tyr Thr Asp Val Thr Phe Lys Thr Arg Lys Ala Ile Pro Tyr Glu
    450                    455                    460
Ser Gly Ile Leu Gly Pro Leu Leu Tyr Gly Glu Val Gly Asp Thr Leu
465                    470                    475                    480
Leu Ile Ile Phe Lys Asn Lys Ala Ser Arg Pro Tyr Asn Ile Tyr Pro
            485                    490                    495
His Gly Ile Thr Asp Val Ser Ala Leu His Pro Gly Arg Leu Leu Lys
            500                    505                    510
Gly Trp Lys His Leu Lys Asp Met Pro Ile Leu Pro Gly Glu Thr Phe
            515                    520                    525
Lys Tyr Lys Trp Thr Val Thr Val Glu Asp Gly Pro Thr Lys Ser Asp
            530                    535                    540
Pro Arg Cys Leu Thr Arg Tyr Tyr Ser Ser Ser Ile Asn Leu Glu Lys
545                    550                    555                    560
Asp Leu Ala Ser Gly Leu Ile Gly Pro Leu Leu Ile Cys Tyr Lys Glu
            565                    570                    575
Ser Val Asp Gln Arg Gly Asn Gln Met Met Ser Asp Lys Arg Asn Val
            580                    585                    590
Ile Leu Phe Ser Val Phe Asp Glu Asn Gln Ser Trp Tyr Leu Ala Glu
            595                    600                    605
Asn Ile Gln Arg Phe Leu Pro Asn Pro Asp Gly Leu Gln Pro Gln Asp
    610                    615                    620
Pro Glu Phe Gln Ala Ser Asn Ile Met His Ser Ile Asn Gly Tyr Val
625                    630                    635                    640
Phe Asp Ser Leu Gln Leu Ser Val Cys Leu His Glu Val Ala Tyr Trp
            645                    650                    655
Tyr Ile Leu Ser Val Gly Ala Gln Thr Asp Phe Leu Ser Val Phe Phe
            660                    665                    670
Ser Gly Tyr Thr Phe Lys His Lys Met Val Tyr Glu Asp Thr Leu Thr
            675                    680                    685
Leu Phe Pro Phe Ser Gly Glu Thr Val Phe Met Ser Met Glu Asn Pro
            690                    695                    700
Gly Leu Trp Val Leu Gly Cys His Asn Ser Asp Leu Arg Asn Arg Gly
705                    710                    715                    720
Met Thr Ala Leu Leu Lys Val Tyr Ser Cys Asp Arg Asp Ile Gly Asp
            725                    730                    735
Tyr Tyr Asp Asn Thr Tyr Glu Asp Ile Pro Gly Phe Leu Leu Ser Gly
            740                    745                    750
Lys Asn Val Ile Glu Pro Arg Asp Ile Ser Leu Pro Thr Phe Gln Pro
            755                    760                    765
Glu Glu Asp Lys Met Asp Tyr Asp Asp Ile Phe Ser Thr Glu Thr Lys
            770                    775                    780
Gly Glu Asp Phe Asp Ile Tyr Gly Glu Asp Glu Asn Gln Asp Pro Arg
785                    790                    795                    800
Ser Phe Gln Lys Arg Thr Arg His Tyr Phe Ile Ala Ala Val Glu Gln
            805                    810                    815
```

```
Leu Trp Asp Tyr Gly Met Ser Glu Ser Pro Arg Ala Leu Arg Asn Arg
        820                 825                 830

Ala Gln Asn Gly Glu Val Pro Arg Phe Lys Lys Val Val Phe Arg Glu
        835                 840                 845

Phe Ala Asp Gly Ser Phe Thr Gln Pro Ser Tyr Arg Gly Glu Leu Asn
        850                 855                 860

Lys His Leu Gly Leu Leu Gly Pro Tyr Ile Arg Ala Glu Val Glu Asp
865                 870                 875                 880

Asn Ile Met Val Thr Phe Lys Asn Gln Ala Ser Arg Pro Tyr Ser Phe
                885                 890                 895

Tyr Ser Ser Leu Ile Ser Tyr Pro Asp Gln Glu Gln Gly Ala Glu
            900                 905                 910

Pro Arg His Asn Phe Val Gln Pro Asn Glu Thr Arg Thr Tyr Phe Trp
            915                 920                 925

Lys Val Gln His His Met Ala Pro Thr Glu Asp Glu Phe Asp Cys Lys
        930                 935                 940

Ala Trp Ala Tyr Phe Ser Asp Val Asp Leu Glu Lys Asp Val His Ser
945                 950                 955                 960

Gly Leu Ile Gly Pro Leu Leu Ile Cys Arg Ala Asn Thr Leu Asn Ala
                965                 970                 975

Ala His Gly Arg Gln Val Thr Val Gln Glu Phe Ala Leu Phe Phe Thr
            980                 985                 990

Ile Phe Asp Glu Thr Lys Ser Trp Tyr Phe Thr Glu Asn Val Glu Arg
        995                 1000                1005

Asn Cys Arg Ala Pro Cys His Leu Gln Met Glu Asp Pro Thr Leu Lys
    1010                1015                1020

Glu Asn Tyr Arg Phe His Ala Ile Asn Gly Tyr Val Met Asp Thr Leu
1025                1030                1035                1040

Pro Gly Leu Val Met Ala Gln Asn Gln Arg Ile Arg Trp Tyr Leu Leu
                1045                1050                1055

Ser Met Gly Ser Asn Glu Asn Ile His Ser Ile His Phe Ser Gly His
        1060                1065                1070

Val Phe Ser Val Arg Lys Lys Glu Glu Tyr Lys Met Ala Val Tyr Asn
        1075                1080                1085

Leu Tyr Pro Gly Val Phe Glu Thr Val Glu Met Leu Pro Ser Lys Val
1090                1095                1100

Gly Ile Trp Arg Ile Glu Cys Leu Ile Gly Glu His Leu Gln Ala Gly
1105                1110                1115                1120

Met Ser Thr Thr Phe Leu Val Tyr Ser Lys Glu Cys Gln Ala Pro Leu
                1125                1130                1135

Gly Met Ala Ser Gly Arg Ile Arg Asp Phe Gln Ile Thr Ala Ser Gly
            1140                1145                1150

Gln Tyr Gly Gln Trp Ala Pro Lys Leu Ala Arg Leu His Tyr Ser Gly
            1155                1160                1165

Ser Ile Asn Ala Trp Ser Thr Lys Asp Pro His Ser Trp Ile Lys Val
    1170                1175                1180

Asp Leu Leu Ala Pro Met Ile Ile His Gly Ile Met Thr Gln Gly Ala
1185                1190                1195                1200

Arg Gln Lys Phe Ser Ser Leu Tyr Ile Ser Gln Phe Ile Ile Met Tyr
                1205                1210                1215

Ser Leu Asp Gly Arg Asn Trp Gln Ser Tyr Arg Gly Asn Ser Thr Gly
            1220                1225                1230

Thr Leu Met Val Phe Phe Gly Asn Val Asp Ala Ser Gly Ile Lys His
        1235                1240                1245
```

| | | | | | | | | | | | | | | |
|---|---|---|---|---|---|---|---|---|---|---|---|---|---|---|
| Asn | Ile | Phe | Asn | Pro | Pro | Ile | Val | Ala | Arg | Tyr | Ile | Arg | Leu | His | Pro |
| | 1250 | | | | | 1255 | | | | | 1260 | | | | |
| Thr | His | Tyr | Ser | Ile | Arg | Ser | Thr | Leu | Arg | Met | Glu | Leu | Met | Gly | Cys |
| 1265 | | | | | 1270 | | | | | 1275 | | | | | 1280 |
| Asp | Leu | Asn | Ser | Cys | Ser | Met | Pro | Leu | Gly | Met | Gln | Asn | Lys | Ala | Ile |
| | | | | 1285 | | | | | 1290 | | | | | 1295 | |
| Ser | Asp | Ser | Gln | Ile | Thr | Ala | Ser | Ser | His | Leu | Ser | Asn | Ile | Phe | Ala |
| | | | | 1300 | | | | | 1305 | | | | | 1310 | |
| Thr | Trp | Ser | Pro | Ser | Gln | Ala | Arg | Leu | His | Leu | Gln | Gly | Arg | Thr | Asn |
| | | | 1315 | | | | | 1320 | | | | | 1325 | | |
| Ala | Trp | Arg | Pro | Arg | Val | Ser | Ser | Ala | Glu | Glu | Trp | Leu | Gln | Val | Asp |
| | | 1330 | | | | | 1335 | | | | | 1340 | | | |
| Leu | Gln | Lys | Thr | Val | Lys | Val | Thr | Gly | Ile | Thr | Thr | Gln | Gly | Val | Lys |
| 1345 | | | | | 1350 | | | | | 1355 | | | | | 1360 |
| Ser | Leu | Leu | Ser | Ser | Met | Tyr | Val | Lys | Glu | Phe | Leu | Val | Ser | Ser | Ser |
| | | | | 1365 | | | | | 1370 | | | | | 1375 | |
| Gln | Asp | Gly | Arg | Arg | Trp | Thr | Leu | Phe | Leu | Gln | Asp | Gly | His | Thr | Lys |
| | | | | 1380 | | | | | 1385 | | | | | 1390 | |
| Val | Phe | Gln | Gly | Asn | Gln | Asp | Ser | Ser | Thr | Pro | Val | Val | Asn | Ala | Leu |
| | | | 1395 | | | | | 1400 | | | | | 1405 | | |
| Asp | Pro | Pro | Leu | Phe | Thr | Arg | Tyr | Leu | Arg | Ile | His | Pro | Thr | Ser | Trp |
| | 1410 | | | | | 1415 | | | | | 1420 | | | | |
| Ala | Gln | His | Ile | Ala | Leu | Arg | Leu | Glu | Val | Leu | Gly | Cys | Glu | Ala | Gln |
| 1425 | | | | | 1430 | | | | | 1435 | | | | | 1440 |
| Asp | Leu | Tyr | | | | | | | | | | | | | |

( 2 ) INFORMATION FOR SEQ ID NO:40:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: Not Relevant ( i i ) MOLECULE TYPE: peptide ( i i i ) HYPOTHETICAL: YES ( v i ) ORIGINAL SOURCE:
        ( A ) ORGANISM: Homo sapiens ( i x ) FEATURE:
        ( A ) NAME/KEY: Peptide
        ( B ) LOCATION: 1..19
        ( D ) OTHER INFORMATION: /note= "Signal peptide of human
            Factor VIII."

( x i ) SEQUENCE DESCRIPTION: SEQ ID NO:40:

| Met | Gln | Ile | Glu | Leu | Ser | Thr | Cys | Phe | Phe | Leu | Cys | Leu | Leu | Arg | Phe |
|---|---|---|---|---|---|---|---|---|---|---|---|---|---|---|---|
| 1 | | | | 5 | | | | | 10 | | | | | 15 | |
| Cys | Phe | Ser | | | | | | | | | | | | | |

MODIFIED FACTOR VIII

This application is a continuation-in-part of PCT/US94/13200, filed Nov. 15, 1994, and of U.S. application Ser. No. 08/212,133, filed Mar. 11, 1994, now U.S. Pat. No. 5,663,060, which is in turn a continuation-in-part of U.S. application Ser. No, 07/864,004, now U.S. Pat. No. 5,364,771, filed Apr. 7, 1992. Priority is claimed from each of the foregoing applications.

The government has rights in this invention arising from National Institutes of Health Grant Nos. HL40921, HL46215, and HL36094 that partially funded the research leading to this invention.

BACKGROUND OF THE INVENTION

This invention relates generally to a hybrid factor VIII having human and animal factor VIII amino acid sequence or having human factor VIII and non-factor VIII amino acid sequence and methods of preparation and use thereof.

This application is a continuation-in-part of PCT/US94/13200 entitled "Hybrid Human/Animal Factor VIII" filed Nov. 15, 1994 by Emory University; which claims priority to U.S. Ser. No. 08/212,133 entitled "Hybrid Human/Animal Factor VIII" filed Mar. 11, 1994, by John S. Lollar and Marschall S. Runge; which is a continuation-in-part of U.S. Ser. No. 07/864,004 entitled "Hybrid Human/Porcine Factor VIII" filed Apr. 7, 1992 by John S. Lollar and Marschall S. Runge, which issued as U.S. Pat. No. 5,364,771 on Nov. 15, 1994.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a, protease that cleaves the next protein precursor in the series. Cofactors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNE®, Proplex®) or recombinant human factor VIIIa. Additionally, since porcine factor VIII usually has substantially less reactivity with inhibitors than human factor VIII, a partially purified porcine factor VIII preparation (HYATE:C®) is used. However, inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 $\mu$g/ml plasma), and has low specific clotting activity.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors to factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

It is an additional object of the present invention to provide a factor VIII against which less antibody is produced.

SUMMARY OF THE INVENTION

The present invention provides isolated, purified, hybrid factor VIII molecules and fragments thereof with coagulant activity including hybrid factor VIII having factor VIII amino acid sequence derived from human and pig or other non-human mammal (together referred to herein as "animal"); or in a second embodiment including a hybrid equivalent factor VIII having factor VIII amino acid sequence derived from human or animal or both and amino acid sequence having no known sequence identity to factor VIII ("non-factor VIII amino acid sequence"), preferably substituted in an antigenic and/or immunogenic region of the factor VIII, is described. One skilled in the art will realize that numerous hybrid factor VIII constructs can prepared including, but not limited to, human/animal factor VIII having greater coagulant activity than human factor VIII ("superior coagulant activity"); non-immunogenic human/ equivalent factor VIII; non-antigenic human/equivalent or human/animal factor VIII; non-immunogenic human/animal or human/equivalent factor VIII having superior coagulant activity; non-antigenic human/animal or human/animal/ equivalent factor VIII having superior coagulant activity; non-immunogenic, non-antigenic human/equivalent or human/equivalent/animal factor VIII; and non-immunogenic, non-antigenic human/animal/equivalent factor VIII having superior coagulant activity.

The hybrid factor VIII molecule is produced by isolation and recombination of human and animal factor VIII subunits or domains; or by genetic engineering of the human and animal factor VIII genes.

In a preferred embodiment, recombinant DNA methods are used to substitute elements of animal factor VIII for the corresponding elements of human factor VIII, resulting in hybrid human/animal factor VIII molecules. In a second preferred embodiment, recombinant DNA methods are used to replace one or more amino acids in the human or animal factor VIII or in a hybrid human/animal factor VIII with amino acids that have no known sequence identity to factor VIII, preferably a sequence of amino acids that has less immunoreactivity with naturally occurring inhibitory antibodies to factor VIII ("nonantigenic amino acid sequence") and/or is less apt to elicit the production of antibodies to factor VIII ("non-immunogenic amino acid sequence") than human factor VIII. An example of an amino acid sequence that can be used to replace immunogenic or antigenic sequence is a sequence of alanine residues.

In another embodiment, subunits of factor VIII are isolated and purified from human or animal plasma, and hybrid human/animal factor VIII is produced either by mixture of animal heavy chain subunits with human light chain subunits or by mixture of human heavy chain subunits with animal light chain subunits, thereby producing human light chain/animal heavy chain and human heavy chain/animal light chain hybrid molecules. These hybrid molecules are isolated by ion exchange chromatography.

Alternatively, one or more domains or partial domains of factor VIII are isolated and purified from human or animal plasma, and hybrid human/animal factor VIII is produced by mixture of domains or partial domains from one species with domains or partial domains of the second species. Hybrid molecules can be isolated by ion exchange chromatography.

Methods for preparing highly purified hybrid factor VIII are described having the steps of: (a) isolation of subunits of plasma-derived human factor VIII and subunits of plasma-derived animal factor VIII, followed by reconstitution of coagulant activity by mixture of human and animal subunits, followed by isolation of hybrid human/animal factor VIII by ion exchange chromatography; (b) isolation of domains or partial domains of plasma-derived human factor VIII and domains or partial domains of plasma-derived animal factor VIII, followed by reconstitution of coagulant activity by mixture of human and animal domains, followed by isolation of hybrid human/animal factor VIII by ion exchange chromatography; (c) construction of domains or partial domains of animal factor VIII by recombinant DNA technology, and recombinant exchange of domains of animal and human factor VIII to produce hybrid human/animal factor VIII with coagulant activity; (d) creation of hybrid human/animal factor VIII by replacement of specific amino acid residues of the factor VIII of one species with the corresponding unique amino acid residues of the factor VIII of the other species; or (e) creation of a hybrid equivalent factor VIII molecule having human or animal amino acid sequence or both in which specific amino acid residues of the factor VIII are replaced with amino acid residues having no known sequence identity to factor VIII by site-directed mutagenesis.

Some embodiments of hybrid or hybrid equivalent factor VIII have specific activity greater than that of human factor VIII and equal to or greater than that of porcine factor VIII. Some embodiments of hybrid or hybrid equivalent factor VIII have equal or less immunoreactivity with inhibitory antibodies to factor VIII and/or less immunogenicity in humans or animals, compared to human or porcine factor VIII.

Also provided are pharmaceutical compositions and methods for treating patients having factor VIII deficiency comprising administering the hybrid or hybrid equivalent factor VIII.

BRIEF DESCRIPTION OF THE DRAWINGS

FIGS. 1A–1H taken together provide an aligned sequence comparison of the human, pig and mouse Factor VIII acid sequences. Human factor VIII amino acid sequence is given in SEQ ID NO:2; porcine factor VIII amino acid sequence is given in SEQ ID NO:37; murine factor VIII amino acid sequence is given in SEQ ID NO:6.

DETAILED DESCRIPTION OF THE INVENTION

Definitions

Unless otherwise specified or indicated, as used herein, "factor VIII" denotes any functional factor VIII protein molecule from any animal, any hybrid factor VIII or modified factor VIII, "hybrid factor VIII" or "hybrid protein" denotes any functional factor VIII protein molecule or fragment thereof comprising factor VIII amino acid sequence from human, porcine, and/or non-human, non-porcine mammalian species. Such combinations include, but are not limited to, any or all of the following hybrid factor VIII molecules or fragments thereof: (1) human/porcine; (2) human/non-human, non-porcine mammalian, such as human/mouse; (3) porcine/non-human, non-porcine mammalian, such as mouse/dog. Such combinations also include hybrid factor VIII equivalent molecules or fragments thereof, as further defined below, comprising factor VIII amino acid sequence of hybrid, human, porcine, or non-human, non-porcine mammalian origin in which amino acid sequence having no known sequence identity to factor VIII is substituted. Such hybrid combinations also include hybrid factor VIII amino acid sequence derived from more than two species, such as human/pig/mouse, or from two or more species in which amino acid sequence having no known sequence identity to factor VIII is substituted. Unless otherwise indicated, "hybrid factor VIII" includes fragments of the hybrid factor VIII, which can be used, as described below in one exemplary embodiment, as probes for research purposes or as diagnostic reagents.

As used herein, "mammalian factor VIII" includes factor VIII with amino acid sequence derived from any non-human mammal, unless otherwise specified. "Animal", as used herein, refers to pig and other non-human mammals.

A "fusion protein" or "fusion factor VIII or fragment thereof", as used herein, is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid VIII protein described in this application.

A "corresponding" nucleic acid or amino acid or sequence of either, as used herein, is one present at a site in a factor VIII or hybrid factor VIII molecule or fragment thereof that has the same structure and/or function as a site in the factor VIII molecule of another species, although the nucleic acid or amino acid number may not be identical. A sequence "corresponding to" another factor VIII sequence substantially corresponds to such sequence, and hybridizes to the sequence of the designated SEQ ID NO. under stringent conditions. A sequence "corresponding to" another factor VIII sequence also includes a sequence that results in the expression of a factor VIII or claimed procoagulant hybrid factor VIII or fragment thereof and would hybridize to the designated SEQ ID NO. but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Hybrid human/porcine factor VIII has coagulation activity in a human factor VIII assay. This activity, as well as that of other hybrid or hybrid equivalent factor VIII molecules or fragments thereof, may be less than, equal to, or greater than that of either plasma-derived or recombinant human factor VIII.

The human factor VIII cDNA nucleotide and predicted amino acid sequences are shown in SEQ ID Nos:1 and 2, respectively. Factor VIII is synthesized as an approximately 300 kDa single chain protein with internal sequence homology that defines the "domain" sequence $NH_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The hybrid factor VIII or fragment thereof can be made (1) by substitution of isolated, plasma-derived animal subunits or human subunits (heavy or light chains) for corresponding human subunits or animal subunits; (2) by substitution of human domains or animal domains (A1, A2, A3, B, C1, and C2) for corresponding animal domains or human domains; (3) by substitution of parts of human domains or animal domains for parts of animal domains or human domains; (4) by substitution of at least one specific sequence including one or more unique human or animal amino acid(s) for the corresponding animal or human amino acid (s); or (5) by substitution of amino acid sequence that has no known sequence identity to factor VIII for at least one sequence including one or more specific amino acid residue (s) in human, animal, or hybrid factor VIII or fragments thereof. A "B-domainless" hybrid factor VIII, hybrid equivalent factor VIII, or fragment of either, as used herein, refers to any one of the hybrid factor VIII constructs described herein that lacks the B domain.

The terms "epitope", "antigenic site", and "antigenic determinant", as used herein, are used synonymously and are defined as a portion of the human, animal, hybrid, or hybrid equivalent factor VIII or fragment thereof that is specifically recognized by an antibody. It can consist of any number of amino acid residues, and it can be dependent upon the primary, secondary, or tertiary structure of the protein. In accordance with this disclosure, a hybrid factor VIII, hybrid factor VIII equivalent, or fragment of either that includes at least one epitope may be used as a reagent in the diagnostic assays described below. In some embodiments, the hybrid or hybrid equivalent factor VIII or fragment thereof is not cross-reactive or is less cross-reactive with all naturally occurring inhibitory factor VIII antibodies than human or porcine factor VIII.

The term "immunogenic site", as used herein, is defined as a region of the human or animal factor VIII, hybrid or hybrid equivalent factor VIII, or fragment thereof that specifically elicits the production of antibody to the factor VIII, hybrid, hybrid equivalent, or fragment in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

As used herein, a "hybrid factor VIII equivalent molecule or fragment thereof" or "hybrid equivalent factor VIII or fragment thereof" is an active factor VIII or hybrid factor VIII molecule or fragment thereof comprising at least one sequence including one or more amino acid residues that have no known identity to human or animal factor VIII sequence substituted for at least one sequence including one or more specific amino acid residues in the human, animal, or hybrid factor VIII or fragment thereof. The sequence of one or more amino acid residues that have no known identity to human or animal factor VIII sequence is also referred to herein as "non-factor VIII amino acid sequence". In a preferred embodiment, the amino acid(s) having no known sequence identity to factor VIII sequence are alanine residues. In another preferred embodiment, the specific factor VIII sequence for which the amino acid(s) having no known sequence identity to factor VIII sequence are substituted includes an antigenic site that is immunoreactive with naturally occurring factor VIII inhibitory antibodies, such that the resulting hybrid factor VIII equivalent molecule or fragment thereof is less immunoreactive or not immunoreactive with factor VIII inhibitory antibodies. In yet another preferred embodiment, the specific hybrid factor VIII sequence for which the amino acid(s) having no known sequence identity to factor VIII sequence are substituted includes an immunogenic site that elicits the formation of factor VIII inhibitory antibodies in an animal or human, such that the resulting hybrid factor VIII equivalent molecule or fragment thereof is less immunogenic.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays know to those of skill in the art. As used herein, however, the hybrid or hybrid equivalent factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the hybrid or hybrid equivalent factor VIII DNA or fragment thereof or protein expressed therefrom, that permits modification of known assays for detection of antibodies to human or animal factor VIII or to hybrid human/animal factor VIII. Such assays include, but are not limited to ELISAs, immunodiffusion assays, and immunoblots. Suitable methods for practicing any of these assays are known to those of skill in the art. As used herein, the hybrid or hybrid equivalent factor VIII or fragment thereof that includes at least one epitope of the protein can be used as the diagnostic reagent. Examples of other assays in which the hybrid or hybrid equivalent factor VIII or fragment thereof can be used include the Bethesda assay and anticoagulation assays.

General Description of Methods

U.S. Ser. No. 07/864,004 describes the discovery of hybrid human/porcine factor VIII molecules having coagulant activity, in which elements of the factor VIII molecule of human or pig are substituted for corresponding elements of the factor VIII molecule of the other species. U.S. Ser. No. 08/212,133 and PCT/US94/13200 describe procoagulant hybrid human/animal and hybrid equivalent factor VIII molecules, in which elements of the factor VIII molecule of one species are substituted for corresponding elements of the factor VIII molecule of the other species.

The present invention provides hybrid human/animal, animal/animal, and equivalent factor VIII molecules and fragments thereof, and the nucleic acid sequences encoding such hybrids, some of which have greater coagulant activity in a standard clotting assay when compared to highly-purified human factor VIII; and/or are less immunoreactive to inhibitory antibodies to human or porcine factor VIII than human or porcine factor VIII; and/or are less immunogenic in a human or animal than human or porcine factor VIII. These hybrid factor VIII molecules can be constructed as follows.

At least five types of active hybrid human/porcine or hybrid equivalent factor VIII molecules or fragments thereof, the nucleic acid sequences encoding these hybrid factor VIII molecules, and the methods for preparing them are disclosed herein: those obtained (1) by substituting a human or porcine subunit (i.e., heavy chain or light chain) for the corresponding porcine or human subunit; (2) by substituting one or more human or porcine domain(s) (i.e., A1, A2, A3, B, C1, and C2) for the corresponding porcine or human domain(s); (3) by substituting a continuous part of one or more human or porcine domain(s) for the corresponding part of one or more porcine or human domain(s); (4) by substituting at least one specific sequence including one or more unique amino acid residue(s) in human or porcine factor VIII for the corresponding porcine or human sequence; and (5) by substituting at least one sequence including one or more amino acid residue(s) having no known sequence identity to factor VIII ("non-factor VIII amino acid sequence") for at least one specific sequence of one or more amino acids in human, porcine, or hybrid human/porcine factor VIII.

At least five types of active hybrid human/non-human, non-porcine mammalian or hybrid equivalent factor VIII molecules or fragments thereof, and the nucleic acid sequences encoding them, can also be prepared by the same methods: those obtained (1) by substituting a human or non-human, non-porcine mammalian subunit (i.e., heavy chain or light chain) for the corresponding non-human, non-porcine mammalian or human subunit; (2) by substituting one or more human or non-human, non-porcine mammalian domain(s) (i.e., A1, A2, A3, B, C1, and C2) for the corresponding non-human, non-porcine mammalian or human domain(s); (3) by substituting a continuous part of one or more human or non-human, non-porcine mammalian domain(s) for the corresponding part of one or more non-human, non-porcine mammalian or human domain(s); (4) by substituting at least one specific sequence including one or more unique amino acid residue(s) in human or non-human, non-porcine mammalian factor VIII for the corresponding non-human, non-porcine mammalian or human sequence; and (5) by substituting at least one sequence including one or more amino acid residue(s) having no known sequence identity to factor VIII ("non-factor VIII amino acid sequence") for at least one specific sequence of one or more amino acids in human, non-human, non-porcine mammalian, or hybrid human/non-human, non-porcine mammalian factor VIII.

Further, one skilled in the art will readily recognize that the same methods can be used to prepare at least five types of active hybrid factor VIII molecules or fragments thereof corresponding to types (1)–(5) in the previous two paragraphs, comprising factor VIII amino acid sequence from two or more non-hum,an mammals, such as porcine/mouse, and further comprising non-factor VIII amino acid sequence.

Hybrid human/animal, animal/animal, and equivalent factor VIII proteins or fragments thereof listed above under groups (1)–(3) are made by isolation of subunits, domains, or continuous parts of domains of plasma-derived factor VIII, followed by reconstitution and purification. Hybrid human/animal, animal/animal, and equivalent factor VIII proteins or fragments thereof described under groups (3)–(5) above are made by recombinant DNA methods. The hybrid molecule may contain a greater or lesser percentage of human than animal sequence, depending on the origin of the various regions, as described in more detail below.

Since current information indicates that the B domain has no inhibitory epitope and has no known effect on factor VIII function, in some embodiments the B domain is deleted in the active hybrid or hybrid equivalent factor VIII molecules or fragments thereof ("B(−) factor VIII") prepared by any of the methods described herein.

It is shown in Example 4 that hybrid human/porcine factor VIII comprising porcine heavy chain and human light chain and corresponding to the first type of hybrid listed above has greater specific coagulant activity in a standard clotting assay compared to human factor VIII. The hybrid human/animal or equivalent factor VIII with coagulant activity, whether the activity is higher, equal to, or lower than that of human factor VIII, can be useful in treating patients with inhibitors, since these inhibitors can react less with hybrid human/animal or equivalent factor VIII than with either human or porcine factor VIII.

Preparation of hybrid factor VIII molecules from isolated human and animal factor VIII subunits by reconstitution The present invention provides hybrid human/animal factor VIII molecules or fragments thereof, with subunit substitutions, the nucleic acid sequences encoding these hybrids, methods for preparing and isolating them, and methods for characterizing their procoagulant activity. One method, modified from procedures reported by Fay, P. J., et al., 265 *J. Biol. Chem.* 6197 (1990); and Lollar, J. S., et al., 263 *J. Biol. Chem.* 10451 (1988), involves the isolation of subunits (heavy and light chains) of human and animal factor VIII, followed by recombination of human heavy chain and animal light chain or by recombination of human light chain and animal heavy chain.

Isolation of both human and animal individual subunits involves dissociation of the light chain/heavy chain dimer. This is accomplished, for example, by chelation of calcium with ethylenediaminetetraacetic acid (EDTA), followed by monoS™ HPLC (Pharmacia-LKB, Piscataway, N.J.). Hybrid human/animal factor VIII molecules are reconstituted from isolated subunits in the presence of calcium. Hybrid human light chain/animal heavy chain or animal light chain/human heavy chain factor VIII is isolated from unreacted heavy chains by monoS™ HPLC by procedures for the isolation of porcine factor VIII, such as described by Lollar, J. S., et al., 71 *Blood* 137–143 (1988).

These methods, used in one embodiment to prepare active hybrid human/porcine factor VIII, described in detail in the examples below, result in hybrid human light chain/porcine heavy chain molecules with greater than six times the procoagulant activity of human factor VIII.

Other hybrid human/non-human, non-porcine mammalian factor VIII molecules can be prepared, isolated, and characterized for activity by the same methods. One skilled in the art will readily recognize that these methods can also be used to prepare, isolate, and characterize for activity hybrid animal/animal factor VIII, such as porcine/mouse, comprising the light or heavy chain or one species is combined with the heavy or light chain of the other species.

Preparation of hybrid factor VIII molecules from isolated human and animal factor VIII domains by reconstitution The present invention provides hybrid human/animal factor VIII molecules or fragments thereof with domain substitutions, the nucleic acid sequences encoding them, methods for preparing and isolating them, and methods for characterizing their procoagulant activity. One method involves the isolation of one or more domains of human and one or more domains of animal factor VIII, followed by recombination of human and animal domains to form hybrid human/animal factor VIII with coagulant activity, as described by Lollar, P., et al., 267(33) *J. Biol. Chem.* 23652–23657 (Nov. 25, 1992), for hybrid human/porcine factor VIII.

Specifically provided is a hybrid human/porcine factor VIII with substitution of the porcine A2 domain for the human A2 domain, which embodiment illustrates a method by which domain-substituted hybrid human/non-human, non-porcine mammalian factor VIII can be constructed. Plasma-derived non-human, non-porcine mammalian and human A1/A3-C1-C2 dimers are isolated by dissociation of the A2 domain from factor VIIIa. This is accomplished, for example, in the presence of NaOH, after which the mixture is diluted and the dimer is eluted using monoS™ HPLC (Pharmacia-LKB, Piscataway, N.J.). The A2 domain is isolated from factor VIIIa as a minor component in The monoS™ HPLC. Hybrid human/animal factor VIII molecules are reconstituted by mixing equal volumes of the A2 domain of one species and the A1/A3-C1-C2 dimer of the other species.

Hybrid human/animal factor VIII or fragments thereof with one or more domain substitutions is isolated from the mixture of unreacted dimers and A2 by monoS™ HPLC by procedures for the isolation of porcine factor VIII, as described by Lollar, J. S., et al., 71 *Blood* 137–143 (1988). Routine methods can also be used to prepare and isolate the A1, A3, C1, C2, and B domains of the factor VIII of one species, any one or more of which can be substituted for the corresponding domain in the factor VIII of the other species. One skilled in the art will readily recognize that these methods can also be used to prepare, isolate, and characterize for activity domain-substituted hybrid animal/animal factor VIII, such as porcine/mouse.

These methods, described in detail in the examples below, result in hybrid factor VIII molecules with procoagulant activity.

Preparation of hybrid factor VIII molecules by recombinant engineering of the sequences encoding human, animal, and hybrid factor VIII subunits, domains, or parts of domains Substitution of subunits, domains, continuous parts of domains:

The present invention provides active, recombinant hybrid human/animal and hybrid equivalent factor VIII molecules and fragments thereof with subunit, domain, and amino acid sequence substitutions, the nucleic acid sequences encoding these hybrids, methods for preparing and isolating them, and methods for characterizing their coagulant, immunoreactive, and immunogenic properties.

The human factor VIII gene was isolated and expressed in mammalian cells, as reported by Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The cDNA sequence encoding human factor VIII and predicted amino acid sequence are shown in SEQ ID Nos:1 and 2, respectively.

Porcine factor VIII has been isolated and purified from plasma (Fass, D. N., et al., 59 *Blood* 594 (1982)). Partial amino acid sequence of porcine factor VIII corresponding to portions of the N-terminal light chain sequence having homology to ceruloplasmin and coagulation factor V and largely incorrectly located were described by Church et al., 81 *Proc. Natl. Acad. Sci. USA* 6934 (1984). Toole, J. J., et al., 312 *Nature* 342–347 (1984) described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J., et al., 83 *Proc. Natl. Acad. Sci. U.S.A.* 5939–5942 (1986). The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Ser. No. 07/864,004 entitled "Hybrid Human/Porcine Factor VIII" filed Apr. 7, 1992 by John S. Lollar and Marschall S. Runge, which issued as U.S. Pat. No. 5,364,771 on Nov. 15, 1994, and in WO 93/20093. The cDNA sequence encoding the A2 domain of porcine factor VIII having sequence identity to residues 373–740 in mature human factor VIII, as shown in SEQ ID NO:1, and the predicted amino acid sequence are shown in SEQ ID NOs:3 and 4, respectively. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor VIIIa, presumably because of the weaker association of the A2 subunit of human factor VIIIa. Dissociation of the A2 subunit of human and porcine factor VIIIa is associated with loss of activity in the factor VIIIa molecule.

Using as probes the known sequence of parts of the porcine factor VIII molecule, the domains of the porcine factor VIII molecule that have not been sequenced to date can be sequenced by standard, established cloning techniques, such as those described in Weis, J. H., "Construction of recombinant DNA libraries," in *Current Protocols in Molecular Biology*, F. M. Ausubel et al., eds. (1991); and Sambrook, J., et al., *Molecular Cloning. A Laboratory Manual*, so that full length hybrids can be constructed.

Specifically provided as an exemplary and a preferred embodiment is active recombinant hybrid human/porcine factor VIII having substituted A2 domain, the nucleic acid sequence encoding it, and the methods for preparing, isolating, and characterizing its activity. The methods by which this hybrid construct is prepared can also be used to prepare active recombinant hybrid human/porcine factor VIII or fragments thereof having substitution of subunits, continuous parts of domains, or domains other than A2. One skilled in the art will recognize that these methods also demonstrate how other recombinant hybrid human/non-human, non-porcine mammalian or animal/animal hybrid factor VIII molecules or fragments thereof can be prepared in which subunits, domains, or continuous parts of domains are substituted.

Recombinant hybrid human/porcine factor VIII is prepared starting with human cDNA (Biogen, Inc.) encoding the factor VIII sequence. In a preferred embodiment, the factor VIII encoded by this cDNA includes domains A1-A2-A3-C1-C2, lacking the entire B domain, and corresponds to amino acid residues 1–740 and 1649–2332 of single chain human factor VIII (see SEQ ID NO:2), according to the numbering system of Wood et al., 312 *Nature* 330–337 (1984).

Individual subunits, domains, or continuous parts of domains of porcine or human factor VIII cDNA can be cloned and substituted for the corresponding human or porcine subunits, domains, or parts of domains by established mutagenesis techniques. For example, Lubin, I. M., et al., 269(12) *J. Biol Chem.* 8639–8641 (March 1994) describes techniques for substituting the porcine A2 domain for the human domain using convenient restriction sites. Other methods for substituting any arbitrary region of the factor VIII cDNA of one species for the factor VIII cDNA of another species include splicing by overlap extension ("SOE"), as described by Horton, R. M., et al., 217 *Meth. Enzymol.* 270–279 (1993).

The hybrid factor VIII cDNA encoding subunits, domains, or parts of domains or the entire hybrid cDNA molecules are cloned into expression vectors for ultimate expression of active hybrid human/porcine factor VIII protein molecules in cultured cells by established techniques, as described by Selden, R. F., "Introduction of DNA into mammalian cells," in *Current Protocols in Molecular Biology*, F. M. Ausubel et al., eds (1991).

In a preferred embodiment, a hybrid human/porcine cDNA encoding factor VIII, in which the porcine sequence encodes a domain or part domain, such the A2 domain or part domain, is inserted in a mammalian expression vector, such as ReNeo, to form a hybrid factor VIII construct. Preliminary characterization of the hybrid factor VIII is accomplished by insertion of the hybrid cDNA into the ReNeo mammalian expression vector and transient expression of the hybrid protein in COS-7 cells. A determination of whether active hybrid protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of recombinant hybrid factor VIII protein can be confirmed, for example, by sequencing, Northern and Western blotting, or polymerase chain reaction (PCR). Hybrid factor VIII protein in the culture media in which the transfected cells stably expressing the protein are maintained can be precipitated, pelleted, washed, and resuspended in an appropriate buffer, and the recombinant hybrid factor VIII protein purified by standard techniques, including immunoaffinity chromatography using, for example, monoclonal anti-A2-Sepharose™.

In a further embodiment, the hybrid factor VIII comprising subunit, domain, or amino acid sequence substitutions is expressed as a fusion protein from a recombinant molecule in which sequence encoding a protein or peptide that enhances, for example, stability, secretion, detection, isolation, or the like is inserted in place adjacent to the factor VIII encoding sequence. Established protocols for use of homologous or heterologous species expression control sequences including, for example, promoters, operators, and regulators, in the preparation of fusion proteins are known and routinely used in the art. See *Current Protocols in Molecular Biology* (Ausubel, F. M., et al., eds), Wiley Interscience, N.Y.

The purified hybrid factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant hybrid factor VIII protein can be expressed in a variety of cells commonly used for culture and recombinant mammalian protein expression. A preferred cell line, available from the American Type Culture Collection, Rockville, Md., is baby hamster kidney cells, which are cultured using routine procedure and media.

The same methods employed for preparing hybrid human/porcine factor VIII having subunit, domain, or amino acid sequence substitution can be used to prepare other recombinant hybrid factor VIII protein and fragments thereof and the nucleic acid sequences encoding these hybrids, such as human/non-human, non-porcine mammalian or animal/animal. Starting with primers from the known human DNA sequence, the murine and part of the porcine factor VIII cDNA have been cloned. Factor VIII sequences of other species for use in preparing a hybrid human/animal or animal/animal factor VIII molecule can be obtained using the known human and porcine DNA sequences as a starting point. Other techniques that can be employed include PCR amplification methods with animal tissue DNA, and use of a cDNA library from the animal to clone out the factor VIII sequence.

As an exemplary embodiment, hybrid human/mouse factor VIII protein can be made as follows. DNA clones corresponding to the mouse homolog of the human factor VIII gene have been isolated and sequenced and the amino acid sequence of mouse factor VIII protein predicted, as described in Elder, G., et al., 16(2) *Genomics* 374–379 (May 1993), which also includes a comparison of the predicted amino acid sequences of mouse, human, and part of porcine factor VIII molecules. The mouse factor VIII cDNA sequence and predicted amino acid sequence are shown in SEQ ID NO:5 and SEQ ID NO:8, respectively. In a preferred embodiment, the RNA amplification with transcript sequencing (RAWTS) methods described in Sarkar, G., and S. S. Sommer, 244 *Science* 331–334 (1989), can be used. Briefly, the steps are (1) cDNA synthesis with oligo (dT) or an mRNA-specific oligonucleotide primer; (2) polymerase chain reaction (PCR) in which one or both oligonucleotides contains a phage promoter attached to a sequence complementary to the region to be amplified; (3) transcription with a phage promoter; and (4) reverse transcriptase-mediated dideoxy sequencing of the transcript, which is primed with a nested (internal) oligonucleotide. In addition to revealing sequence information, this method can generate an in vitro translation product by incorporating a translation initiation signal into the appropriate PCR primer; and can be used to obtain novel mRNA sequence information from other species.

Substitution of amino acid(s):

The present invention provides active recombinant hybrid human/animal and animal/animal factor VIII molecules or fragments thereof comprising at least one sequence including one or more unique amino acids of one species substituted for the corresponding amino acid sequence of the other species or fragments thereof, nucleic acid sequences encoding these hybrids, methods for preparing and isolating them, and methods for characterizing their coagulant, immunogenic, and immunoreactive properties.

The A2 domain is necessary for the procoagulant activity of the factor VIII molecule. Studies show that porcine factor VII:I has six-fold greater procoagulant activity than human factor VIII (Lollar, P., and E. T. Parker 266 *J. Biol. Chem.* 12481–12486 (1991)), and that the difference in coagulant activity between human and porcine factor VIII appears to be based on a difference in amino acid sequence between one or more residues in the human and porcine A2 domains (Lollar, P., et al., 267 *J. Biol. Chem.* 23652–23657 (1992)). Further, the A2 and C2 domains and possibly a third light chain region in the human factor VIII molecule are thought to harbor the epitopes to which most, if not all, inhibitory antibodies react, according to Hoyer, L. W., and D. Scandella, 31 *Semin. Hematol.* 1–5 (1994).

Recombinant hybrid human/animal, animal/animal, or equivalent factor VIII molecules or fragments thereof can be made by substitution of at least one specific sequence including one or more unique amino acids from the A2, C2, and/or other domains of the factor VIII of one species for the corresponding sequence of the other species, wherein the amino acid sequences differ, as illustrated in more detail below, between the molecules of the two species. In an exemplary preferred embodiment described herein, the present invention provides active recombinant hybrid human/porcine factor VIII comprising porcine amino acid sequence substituted for corresponding human amino acid sequence that includes an epitope, wherein the hybrid factor VIII has decreased or no immunoreactivity with inhibitory antibodies to factor VIII. In a further embodiment, active recombinant hybrid factor VIII molecules can also be made comprising amino acid sequence from more than one species substituted for the corresponding sequence in a third species.

Recombinant hybrid equivalent molecules can also be made, comprising human, animal, or hybrid factor VIII including at least one sequence including one or more amino acids that have no known sequence identity to factor VIII, as further described below.

Any hybrid factor VIII construct having specific amino acid substitution as described can be assayed by standard procedures for coagulant activity and for reactivity with inhibitory antibodies to factor VIII for identification of hybrid factor VIII molecules with enhanced coagulant activity and/or decreased antibody immunoreactivity. Hybrid molecules may also be identified that have reduced coagulant activity compared to human or porcine factor VIII but also have decreased antibody reactivity. One skilled in the art will recognize that hybrid factor VIII molecules or fragments thereof having less, equal, or greater coagulant activity, compared to human or porcine factor VIII, is useful for treating patients who have a factor VIII deficiency. The methods described herein to prepare active recombinant hybrid human/porcine factor VIII with substitution of specific amino acids can be used to prepare active recombinant hybrid human/non-human, non-porcine mammalian factor VIII protein, hybrid animal-1/animal-2 factor VIII, and hybrid equivalent factor VIII or fragments thereof.

Hybrid factor VIII molecules with altered coagulant activity.

The present invention provides procoagulant recombinant hybrid human/animal, animal/animal, or equivalent factor VIII molecules or fragments thereof comprising at least one specific sequence including one or more unique amino acids having procoagulant activity in the factor VIII of one species substituted for the corresponding amino acid sequence of the factor VIII of the other species, using established site-directed mutagenesis techniques as described herein. The specific sequences to be used in the substitution are selected and the hybrid constructs are prepared and assayed for coagulant activity, as follows. Specifically provided as a preferred and exemplary embodiment is a hybrid human/porcine factor VIII comprising amino acid substitutions in the A2 domain. It is understood that one skilled in the art can use these methods to prepare other hybrid human/animal, animal/animal, and equivalent factor VIII molecules or fragments thereof having altered coagulant activity, preferably increased coagulant activity compared to human factor VIII.

The basis for the greater coagulant activity in porcine factor VIII appears to be the more rapid spontaneous dissociation of the A2 subunit of human factor VIIIa than porcine factor VIIIa, which leads to loss of activity, according to Lollar, P., and C. G. Parker, 265 *J. Biol. Chem.* 1688–1692 (1990); Lollar, P., et al. 267 *J. Biol. Chem.* 23652–23657 (1992); Fay, P. J., and T. M. Smudzin, 267 *J, Biol. Chem.* 13246–13250 (1992).

A comparison of the alignment of the amino acid sequences of the human and porcine factor VIII A2 domains (residue numbering starts at position 373 with respect to the full length amino acid sequence of human factor VIII, SEQ ID NO:2) is shown in FIG. 1C. For preparation of a hybrid human/porcine factor VIII molecule with altered coagulant activity, the initial target candidates for mutagenesis, which were revealed upon comparison of the human and porcine A2 amino acid sequences (SEQ ID NOs:2 and 6, respectively) within the human A2 domain, are shown in Table I.

TABLE I

HUMAN AMINO ACID SEQUENCE TARGET CANDIDATES FOR MUTAGENESIS (SEQ ID NO: 2)

| Sequence | Residues | Mismatches | Charge Changes |
|---|---|---|---|
| 398–403 | 6 | 4 | 1 |
| 434–444 | 10 | 4 | 3 |
| 484–496 | 13 | 7 | 3 |
| 598–603 | 6 | 4 | 2 |
| 536–541 | 6 | 4 | 0 |
| 713–722 | 10 | 6 | 2 |
| 727–737 | 11 | 6 | 2 |

Table I and the bold letters of FIG. 1A–1B illustrate seven sequences in the human and pig A2 domain amino acid sequences (SEQ ID NOs:2 and 6, respectively) that constitute only 17 percent of the A2 domain but include 70 percent of the sequence differences between human and porcine A2 domains.

A recombinant hybrid human/porcine construct is described in which amino acids Ser373-Glu604 in the A2 domain (Ser373-Arg740) of human factor VIII have been replaced with the homologous porcine sequence. This construct does not react with A2 inhibitors and has the same coagulant activity as human B(−) factor VIII. A plasma-derived hybrid molecule is described that comprises a complete porcine A2 domain substitution in the human factor VIII that has increased coagulant activity compared to human factor VIII. Comparison of these constructs indicates that a region between residues Asp605 and Arg740 is responsible for the difference in activity between human and porcine factor VIII. This region can be defined more specifically by systematically making recombinant hybrid human/porcine factor VIII molecules with porcine substitutions in the region between Asp605 and Arg740 by using established site-directed mutagenesis techniques, for example, the "splicing by overlap extension" (SOE) method that has been used extensively to make hybrid factor VIII molecules containing porcine substitutions in the $NH_2$-terminal region of A2. These molecules can be expressed in COS-7 cells and baby hamster kidney cells as described above. They can be purified to homogeneity using methods known in the art, such as heparin-Sepharose™ and immunoaffinity chromatography. Protein concentration can be estimated by absorption of ultraviolet light at $A_{280}$, and the specific activity of the constructs can be determined by dividing coagulant activity (measured in units per ml by single stage clotting assay) by $A_{280}$. Human factor VIII has a specific activity of approximately 3000–4000 U/$A_{280}$, whereas porcine factor VIII has a specific activity of approximately 20,000 U/$A_{280}$. In a preferred embodiment, the procoagulant recombinant hybrid human/porcine factor VIII has a specific activity of 20,000 U/$A_{280}$ and contains a minimal amount of porcine substitution in the A2 domain.

As described herein, site-directed mutagenesis techniques are used to identify hybrid protein with coagulant activity that can be enhanced, equal to, or reduced, compared to human factor VIII, but preferably is enhanced. In the hybrid human/porcine embodiment, specific human sequences are replaced with porcine sequences, preferably using the splicing by overlap extension method (SOE), as described by Ho, S. N., et al., 77 *Gene* 51–59 (1994), and in Examples 7 and 8. Oligonucleotide-directed mutagenesis can also be used, as was done to loop out the amino acid sequence for part of the human A2 domain (see Example 7). As functional analysis of the hybrids reveals coagulant activity, the sequence can be further dissected and mapped for procoagulant sequence by standard point mutation analysis techniques.

The present invention contemplates that hybrid factor VIII cDNA and protein can be characterized by methods that are established and routine, such as DNA sequencing, coagulant activity assays, mass by ELISA and by UV absorbance at 280 nm of purified hybrid factor VIII, specific coagulant activity (U/mg), SDS-PAGE of purified hybrid factor VIII, and the like. Other known methods of testing for clinical effectiveness may be required, such as amino acid, carbohydrate, sulfate, or metal ion analysis.

A recombinant hybrid factor VIII having superior coagulant activity, compared to human factor VIII, may be less expensive to make than plasma-derived factor VIII and may decrease the amount of factor VIII required for effective treatment of factor VIII deficiency.

Hybrid factor VIII molecules with reduced immunoreactivity.

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, over 90 percent of inhibitory antibodies to human factor VIII act by binding to epitopes located in the 40 kDa A2 domain or 20 kDa C2 domain of factor VIII, disrupting specific functions associated with these domains, as described by Fulcher et al., 82 *Proc. Natl. Acad. Sci. USA* 7728–7732 (1985), and Scandella et al., 85 *Proc. Natl. Acad. Sci. USA* 6152–6156 (1988). In addition to the A2 and C2 epitopes, there may be a third epitope in the A3 or C1 domain of the light chain of factor VIII, according to Scandella et al., 82 *Blood* 1767–1775 (1993). The significance of this putative third epitope is unknown, but it appears to account for a minor fraction of the epitope reactivity in factor VIII.

Anti-A2 antibodies block factor X activation, as shown by Lollar et al., 93 *J. Clin. Invest.* 2497–2504 (1994). Previous mapping studies by deletion mutagenesis described by Ware et al., 3 *Blood Coagul. Fibrinolysis* 703–716 (1992), located the A2 epitope to within a 20 kDa region at the $NH_2$-terminal end of the 40 kDa A2 domain. Competition immunoradiometric assays have indicated that A2 inhibitors recognize either a common epitope or narrowly clustered epitopes, as described by Scandella et al., 67 *Thromb. Haemostas.* 665–671 (1992), and as demonstrated in Example 8.

The present invention provides active recombinant hybrid and hybrid equivalent factor VIII molecules or fragments thereof, the nucleic acid sequences encoding these hybrids, methods of preparing and isolating them, and methods for characterizing them. These hybrids comprise human/animal, animal/animal, or equivalent hybrid factor VIII molecules, further comprising at least one specific amino acid sequence including one or more unique amino acids of the factor VIII of one species substituted for the corresponding amino acid sequence of the factor VIII of the other species; or comprises at least one sequence including one or more amino acids having no known sequence identity to factor VIII substituted for specific amino acid sequence in human, animal, or hybrid factor VIII. The resulting hybrid factor VIII has reduced or no immunoreactivity to factor VIII inhibitory antibodies, compared to human or porcine factor VIII.

Using the approach described in the previous section for substitution of amino acids in the factor VIII molecule, mutational analysis is employed to select corresponding factor VIII amino acid sequence of one species, preferably porcine, which is substituted for at least one sequence including one or more amino acids in the factor VIII of another species, preferably human, or for amino acid sequence of a hybrid equivalent factor VIII molecule, that includes one or more critical region(s) in the A2, C2, or any other domain to which inhibitory antibodies are directed. The methods are described in more detail below. The resulting procoagulant recombinant hybrid construct has reduced or no immunoreactivity to inhibitory antibodies, compared in human factor VIII, using standard assays. Through systematic substitution of increasingly smaller amino acid sequences followed by assay of the hybrid construct for immunoreactivity, as described below any epitope in any domain of a factor VIII molecule is mapped, substituted by amino acid sequence having less or no immunoreactivity, and a hybrid factor VIII is prepared.

It is understood that one skilled in the art can use this approach combining epitope mapping, construction of hybrid factor VIII molecules, and mutational analysis of the constructs to identify and replace at least one sequence including one or more amino acids comprising an epitope in the A2, C2, and/or other domains to which inhibitory antibodies are directed and to construct procoagulant recombinant hybrid human/animal, animal/animal, or equivalent factor VIII or fragments thereof having decreased or no immunoreactivity compared to human or porcine factor VIII. This approach is used, as described in Example 8, to prepare a recombinant procoagulant hybrid human/porcine factor VIII having porcine amino acid substitutions in the human A2 domain and no antigenicity to anti-factor VIII antibodies as an exemplary embodiment.

Usually, porcine factor VIII has limited or no reaction with inhibitory antibodies to human factor VIII. The recombinant hybrid human/porcine factor VIII molecules having decreased or no reactivity with inhibitory antibodies based on amino acid substitution in the A2 domain are prepared, as an example of how hybrid factor VIII can be prepared using the factor VIII of other species and substitutions in domains other than the A2, as follows. The porcine A2 domain is cloned by standard cloning techniques, such as those described above and in Example 6, 7, and 8, and then cut and spliced within the A2 domain using routine procedures, such as using restriction sites to cut the cDNA or splicing by overlap extension (SOE). The resulting porcine amino acid sequence is substituted into the human A2 domain to form a hybrid factor VIII construct, which is inserted into a mammalian expression vector, preferably ReNeo, stably transfected into cultured cells, preferably baby hamster kidney cells, and expressed, as described above. The hybrid factor VIII is assayed for immunoreactivity, for example with anti-A2 antibodies by the routine Bethesda assay or by plasma-free chromogenic substrate assay. The Bethesda unit (BU) is the standard method for measuring inhibitor titers. If the Bethesda titer is not measurable (<0.7 BU/mg IgG) in the hybrid, then a human A2 epitope was eliminated in the region of substituted corresponding porcine sequence. The epitope is progressively narrowed, and the specific A2 epitope can thus be determined to produce a hybrid human/porcine molecule with as little porcine sequence as possible. As described herein, a 25-residue sequence corresponding to amino acids Arg484-Ile508 that is critical for inhibitory immunoreactivity has been identified and substituted in the human A2 domain. Within this sequence are only nine differences between human and porcine factor VIII. This region can be further analyzed and substituted.

Hybrid human/porcine factor VIII molecules having decreased or no reactivity with inhibitory antibodies based on substitution of amino acid sequence in the C1, C2, or other domain, with or without substitution in the A2 domain, can also be prepared. The C2 epitope, for example, can be mapped using the homolog scanning approach combined with site-directed mutagenesis. More specifically, the procedures can be the same or similar to those described herein for amino acid substitution in the A2 domain, including cloning the porcine C2 or other domain, for example by using RT-PCR or by probing a porcine liver cDNA library with human C2 or other domain DNA; restriction site techniques and/or successive SOE to map and simultaneously replace epitopes in the C2 or other domain; substitution for the human C2 or other domain in B(−) factor VIII; insertion into an expression vector, such as pBluescript; expression in cultured cells; and routine assay for immunoreactivity. For the assays, the reactivity of C2 hybrid factor VIII with a C2-specific inhibitor, MR (Scandella, D., et al., Thromb. Haemostasis 67:665–671 (1992) and Lubin et al. (1994)), and/or other C2 specific antibodies prepared by affinity chromatography can be performed.

The C2 domain consists of amino acid residues 2173–2332 (SEQ ID NO:2). Within this 154 amino acid region, inhibitor activity appears to be directed to a 65 amino acid region between residues 2248 and 2312, according to Shima, M., et al., 69 Thromb. Haemostas. 240–246 (1993). If the C2 sequence of human and porcine factor VIII is approximately 85 percent identical in this region, as it is elsewhere in the functionally active regions of factor VIII, there will be approximately ten differences between human and porcine factor VIII C2 amino acid sequence, which can be used as initial targets to construct hybrids with substituted C2 sequence.

It is likely that clinically significant factor VIII epitopes are confined to the A2 and C2 domains. However, if antibodies to other regions (A1, A3, B, or C1 domains) of factor VIII are identified, the epitopes can be mapped and eliminated by using the approach described herein for the nonantigenic hybrid human/porcine factor VIII molecules.

More specifically, mapping of the putative second light chain epitope and/or any other epitope in any other animal or human factor VIII domain can also be accomplished. Initially, determination of the presence of a third inhibitor epitope in the A3 or C1 domains can be made as follows. Using human ("H") and porcine ("p") factor VIII amino acid sequences as a model, $A1_p$-$A2_p$-$A3_p$-$C1_H$-$C2_p$ and $A1_p$-$A2_p$-$A3_H$-$C1_p$-$C2_p$ B-domainless hybrids will be constructed. Inhibitor IgG from approximately 20 patient plasmas (from Dr. Dorothea Scandella, American Red Cross) who have low or undetectable titers against porcine factor VIII will be tested against the hybrids. If the third epitope is in the A3 domain, inhibitory IgG is expected to react with $A1_p$-$A2_p$-$A3_H$-$C1_p$-$C2_p$ but not $A1_p$-$A2_p$-$A3_p$-$C1_H$-$C2_p$. Conversely, if the third epitope is in the C1 domain, then inhibitory IgG is expected to react with $A1_p$-$A2_p$-$A3_p$-$C1_H$-$C2_p$ but not $A1_p$-$A2_p$-$A3_H$-$C1_p$-$C2_p$. If a third epitope is identified it will be characterized by the procedures described herein for the A2 and C2 epitopes.

For example, antibodies specific for the C1 or A3 domain epitope can be isolated from total patient IgG by affinity chromatography using the $A1_p$-$A2_p$-$A3_H$-$C1_p$-$C2_p$ and $A1_p$-$A2_p$-$A3_p$-$C1_H$-$C2_p$ hybrids, and by elimination of C2 specific antibodies by passage over recombinant factor VIII C2-Sepharose™. The putative third epitope will be identified by SOE constructs in which, in a preferred embodiment, portions of the human factor VIII A3 or C1 domain are systematically replaced with porcine sequence.

Hybrid factor VIII molecules with reduced immunogenicity.

A molecule is immunogenic when it can induce the production of antibodies in human or animal. The present invention provides a procoagulant recombinant hybrid human/animal or animal/animal factor VIII molecule, hybrid factor VIII equivalent molecule, or fragment of either that is less immunogenic than wild-type human porcine factor VIII in human or animal, comprising at least one specific amino acid sequence including one or more unique amino acids of the factor VIII of one species substituted for the corresponding amino acid sequence that has immunogenic activity of the factor VIII of the other species; or at least one amino acid sequence including one or more amino acids having no known identity to factor VIII substituted for amino acid sequence of the human, animal, or hybrid factor. This hybrid can be used to lower the incidence of inhibitor development in an animal or human and to treat factor VIII deficiency, and would be preferred in treating previously untreated patients with hemophilia. In a preferred embodiment, the hybrid factor VIII comprises human factor VIII amino acid sequence, further comprising one or more alanine residues substituted for human amino acid sequence having immunogenic activity, resulting in a procoagulant recombinant hybrid equivalent molecule or fragment thereof having reduced or no immunogenicity in human or animal.

The process described herein of epitope mapping and mutational analysis combined with substitution of nonantigenic amino acid sequence in a factor VIII molecule, using hybrid human/porcine factor VIII, produces hybrid molecules with low antigenicity. Using this model and the associated methods, any of the hybrid constructs described herein can be altered by site-directed mutagenesis techniques to remove as much of any functional epitope as possible to minimize the ability of the immune system to recognize the hybrid factor VIII, thereby decreasing its immunogenicity.

One method that can be used to further reduce the antigenicity and to construct a less immunogenic hybrid factor VIII is alanine scanning mutagenesis, described by Cunningham, B. C., and J. A. Wells, 244 Science 1081–1085 (1989), of selected specific amino acid sequences in human, animal, or hybrid equivalent factor VIII. In alanine scanning mutagenesis, amino acid side chains that are putatively involved in an epitope are replaced by alanine residues by using site-directed mutagenesis. By comparing antibody binding of alanine mutants to wild-type protein, the relative contribution of individual side chains to the binding interaction can be determined. Alanine substitutions are likely to be especially useful, since side chain contributions to antibody binding are eliminated beyond the β carbon, but, unlike glycine substitution, main chain conformation is not usually altered. Alanine substitution does not impose major steric, hydrophobic or electrostatic effects that dominate protein-protein interactions.

In protein antigen-antibody interactions, there usually are about 15–20 antigen side chains in contact with the antibody. Side chain interactions, as opposed to main chain interactions, dominate protein-protein interactions. Recent studies have suggested that only a few (approximately 3 to 5) of these side-chain interactions contribute most of the binding energy. See Clackson, T., and J. A. Wella, 267

*Science* 383–386 (1995). An extensive analysis of growth hormone epitopes for several murine monoclonal antibodies revealed the following hierarchy for side chain contributions to the binding energy: Arg>Pro>Glu~Asp~Phe~Ile, with Trp, Ala, Gly, and Cys not tested (Jin, L., et al., 226 *J. Mole Biol.* 851–865 (1992)). Results with the A2 epitope described herein are consistent with this, since twelve of the 25 residues in the 484–508 A2 segment contain these side chains (Table 1).

The finding that certain amino acid residues are particularly well recognized by antibodies, indicates that elimination of these residues from a known epitope can decrease the ability of the immune system to recognize these epitopes, i.e., can make a molecule less immunogenic. In the case of the A2 epitope, immunogenic residues can be replaced without loss of factor VIII coagulant activity. For example, in HP9, Arg484 is replaced by Ser, Pro485 is replaced by Ala, Arg489 is replaced by Gly, Pro492 is replaced by Leu, and Phe501 is replaced by Met. Further, results from the patient plasmas used to test immunoreactivity in hybrid human/porcine factor VIII constructs, described in Example 8, indicate that antibodies from different patients recognize the same or a very similar structural region in the A2 domain and that the residues in the A2 domain that participate in binding A2 inhibitors appear to show little variation. Thus, the A2 epitope included in human factor VIII residues 484–508 is an immunodominant epitope in that it is recognized by the human immune system better than other structural regions of factor VIII. Replacing this structure by nonantigenic factor VIII sequence from another species or by non-factor VIII amino acid sequence, while retaining full procoagulant activity, is expected to alter recognition of hybrid or hybrid equivalent factor VIII by the immune system.

It is anticipated that site-directed mutagenesis to replace bulky and/or charged residues that tend to dominate epitopes with small, neutral side chains (e.g., alanine) may produce a less immunogenic region. It is expected that a molecule containing a few of these substitutions at each significant inhibitor epitope will be difficult for the immune system to fit by the lock-and-key mechanism that is typical of antigen-antibody interactions. Because of its low antigenicity, such a hybrid molecule could be useful in treating factor VIII deficiency patients with inhibitors, and because of its low immunogenicity, it could useful in treating previously untreated patients with hemophilia A.

A general result is that mutation of one of a few key residues is sufficient to decrease the binding constant for a given protein-protein interaction by several orders of magnitude. Thus, it appears likely that all factor VIII epitopes contain a limited number of amino acids that are critical for inhibitor development. For each epitope in factor VIII, alanine substitutions for at least one sequence including one or more specific amino acids having immunogenic activity, may produce an active molecule that is less immunogenic than wild-type factor VIII. In a preferred embodiment, the hybrid factor VIII is B-domainless.

The methods for preparing active recombinant hybrid or hybrid equivalent factor VIII with substitution of amino acid sequence having little or no immunogenic activity for amino acid sequence in the factor VIII having immunogenic activity are as follows, using hybrid human/porcine factor VIII with amino acid substitutions in the A2 domain as an exemplary embodiment. There are 25 residues in the human factor VIII region 484–508. Site-directed mutagenesis can be used to make single mutants in which any of these residues is replaced by any of the other 19 amino acids for a total of 475 mutants. Furthermore, hybrid molecules having more than one mutation can be constructed.

The hybrid constructs can be assayed for antigenicity by measuring the binding constant for inhibitor antibodies, as described by Friguet, B., et al., 77 *J. Immunol. Methods* 77:305–319 (1985). In a preferred embodiment, the binding constant will be reduced by at least three orders of magnitude, which would lower the Bethesda titer to a level that is clinically insignificant. For example, the $IC_{50}$ (a crude measure of the binding constant) of inhibition by A2 antibodies was reduced in hybrid human/porcine factor VIII constructs HP2, HP4, HP5, HP7, and HP9, described in Example 8, and this was associated with a reduction in Bethesda titer to an unmeasurable level. It is anticipated, for example, that a double or triple alanine mutant of human factor VIII (e.g., a human factor VIII Arg484→Ala, Arg489→Ala, Phe501→Ala triple mutant) will produce a molecule with sufficiently low antigenicity for mutations case similar mutations can be made in the C2 epitope and the putative third epitope. In a preferred embodiment comprises two or three alanine substitutions into two or three factor VIII epitopes. Other substitutions into these regions can be also be done.

In a preferred embodiment, hybrid equivalent factor VIII molecules will be identified that are less antigenic and/or immunogenic in human and animal than either human or porcine factor VIII. Such hybrid equivalent constructs can be tested in animals for their reduced antigenicity and/or immunogenicity. For example, control and factor VIII deficient rabbits, pigs, dogs, mice, primates, and other mammals can be used as animal models. In one experimental protocol, the hybrid or hybrid equivalent factor VIII can be administered systematically over a period of six months to one year to the animal, preferably by intravenous infusion, and in a dosage range between 5 and 50 Units/kg body weight, preferably 10–50 Units/kg, and most preferably 40 Units/kg body weight. Antibodies can be measured in plasma samples taken at intervals after the infusions over the duration of the testing period by routine methods, including immunoassay and the Bethesda assay. Coagulant activity can also be measured in samples with routine procedures, including a one-stage coagulation assay.

The hybrid equivalent factor VIII molecules can be tested in humans for their reduced antigenicity and/or immunogenicity in at least two types of clinical trials. In one type of trial, designed to determine whether the hybrid or hybrid equivalent factor VIII is immunoreactive with inhibitory antibodies, hybrid or hybrid equivalent factor VIII is administered, preferably by intravenous infusion, to approximately 25 patients having factor VIII deficiency who have antibodies to factor VIII that inhibit the coagulant activity of therapeutic human or porcine factor VIII. The dosage of the hybrid or hybrid equivalent factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titer and inhibitory activity. If the antibody titer is high, factor VIII recovery usually cannot be measured. The recovery results are compared to the recovery of recovery results in patients treated with plasma-derived human factor VIII, recombinant human factor VIII, porcine factor VIII, and other commonly used therapeutic forms of factor VIII or factor VIII substitutes.

In a second type of clinical trial, designed to determine whether the hybrid or hybrid equivalent factor VIII is immunogenic, i.e., whether patients will develop inhibitory antibodies, hybrid or hybrid equivalent factor VIII is administered, as described in the preceeding paragraph, to approximately 100 previously untreated hemophiliac patients who have not developed antibodies to factor VIII Treatments are given approximately every 2 weeks over a period of 6 months to 1 year. At 1 to 3 month intervals during this period, blood samples are drawn and Bethesda assays or other antibody assays are performed to determine the presence of inhibitory antibodies. Recovery assays can also be done, as described above, after each infusion. Results are compared to hemophiliac patients who receive plasma-derived human factor VIII, recombinant human factor VIII, porcine factor VIII, or other commonly used therapeutic forms of factor VIII or factor VIII substitutes.

Preparation of hybrid factor VIII molecules using human and non-porcine, non-human mammalian factor VIII amino acid sequence The methods used to prepare hybrid human/porcine factor VIII with substitution of specific amino acids can be used to prepare recombinant hybrid human/non-human, non-porcine mammalian or animal/animal factor VIII protein that has, compared to human or porcine factor VIII, altered or the same coagulant activity and/or equal or reduced immunoreactivity and/or Immunogenicity, based on substitution of one or more amino acids in the A2, C2, and/or other domains.

Similar comparisons of amino acid sequence identity can be made between human and non-human, non-porcine mammalian factor VIII proteins to determine the amino acid sequences in which procoagulant activity, anti-A2 and anti-C2 immunoreactivity, and or immunogenicity, or immunoreactivity and/or immunogenicity in other domains reside. Similar methods can then be used to prepare hybrid human/non-human, non-porcine mammalian factor VIII molecules. As described above, functional analysis of each hybrid will reveal those with decreased reactivity to inhibitory antibodies, and/or reduced immunogenicity, and/or increased coagulant activity, and the sequence can be further dissected by point mutation analysis.

For example, hybrid human/mouse factor VIII molecules can be prepared as described above. The amino acid sequence alignment of the A2 domain of human (SEQ ID NO:2) and mouse (SEQ ID NO:6) is shown in FIG. 1C. As reported by Elder et al. the factor VIII protein encoded by the mouse cDNA (SEQ ID NO:5) has 2319 amino acids, with 74% sequence identity overall to the human sequence (SEQ ID NO:2) (87 percent identity when the B domain is excluded from the comparison), and is 32 amino acids shorter than human factor VIII. The amino acid sequences in the mouse A and C domains (SEQ ID NO:6) are highly conserved, with 84–93 percent sequence identity to the human sequence (SEQ ID NO:2), while the B and the two short acidic domains have 42–70 percent sequence identity. Specifically, the A1, A2, and A3 mouse amino acid sequences (SEQ ID NO:6) are 85, 85, and 90 percent identical to the corresponding human amino acid sequences (SEQ ID NO:2). The C1 and C2 mouse amino acid sequences are 93 and 84 percent identical to the corresponding human amino acid sequences. In the predicted mouse factor VIII amino acid sequence (SEQ ID NO:6), the A1, A2, and A3 domains are homologous to human factor VIII amino acids 1–372, 373–740, and 1690–2032, respectively, using amino acid sequence identity for numbering purposes.

The thrombin/factor Xa and all but one activated protein C cleavage sites are conserved in mouse factor VIII. The tyrosine residue for von Willebrand factor binding is also conserved.

According to Elder et al., the nucleotide sequence (SEQ ID NO:5) of mouse factor VIII contains 7519 bases and has 67 percent identity overall with the human nucleotide sequence (SEQ ID NO:1). The 6957 base pairs of murine coding sequence have 82 percent sequence identity with the 7053 base pairs of coding sequence in human factor VIII. When the B domain is not included in the comparison, there is an 88 percent nucleotide sequence identity.

Elder et al. report that human and mouse factor VIII molecules are 74 percent identical overall, and that 95 percent of the human residues that lead to hemophilia when altered are identical in the mouse. These data support the application of the same techniques used to identify amino acid sequence with coagulant activity and/or immunoreactivity to antibodies in the porcine factor VIII molecule to the mouse or other animal factor VIII to identify similar amino acid sequences and prepare hybrid molecules.

Preparation of hybrid factor VIII molecules having reduced cross-reactivity using human and non-human, non-porcine mammalian factor VIII amino acid sequence and non-factor VIII amino acid sequence Porcine factor VIII is used clinically to treat factor VIII deficiency patients who have inhibitory antibodies to human factor VIII. Cross-reactivity, in which human plasma reacts with porcine factor VIII, can be reduced by preparation of hybrid porcine/non-human, non-porcine mammalian or hybrid equivalent factor VIII. In a preferred embodiment, a determination of whether human A2, C2, or other domain-specific inhibitors react with non-human, non-porcine mammalian ("other mammalian") factor VIII is made, using the routine Bethesda assay and the particular other mammalian plasma as the standard. Inhibitor titers are usually measured in plasma, so purified other mammalian factor VIII is not necessary. If the inhibitors do not react with the other mammalian factor VIII, such as murine factor VIII, the sequence of which is known, then corresponding other mammalian sequence can be substituted into the porcine epitope region, as identified by using human/porcine hybrids. Once the animal sequence is known, site directed mutagenesis techniques, such as oligonucleotide-mediated mutagenesis described by Kunkel, T. A., et al., 204 Meth. Enzymol. 125–139 (1991), can be used to prepare the hybrid porcine/animal factor VIII molecule. If other animal plasmas are less reactive with A2, C2, or other factor VIII inhibitors than murine or porcine factor VIII, the animal sequence corresponding to the porcine epitope can be determined by routine procedures, such as RT-PCR, and a hybrid human/animal or porcine/animal factor VIII constructed by site directed mutagenesis. Also, hybrid human/animal or porcine/non-porcine mammalian factor VIII having reduced cross-reactivity with human plasma compared to porcine factor VIII can be prepared that has corresponding amino acid sequence substitution from one or more other animals. In a further embodiment, cross-reactivity can be reduced by substitution of amino acid sequence having no known identity to factor VIII amino acid sequence, preferably alanine residues using alanine scanning mutagenesis techniques, for porcine epitope sequence.

After identification of clinically significant epitopes, recombinant hybrid factor VIII molecules will be expressed that have less than or equal cross-reactivity compared with porcine factor VIII when tested in vitro against a broad survey of inhibitor plasmas. Preferably these molecules will be combined A2/C2 hybrids in which immunoreactive amino acid sequence in these domains is replaced by other mammalian sequence. Additional mutagenesis in these regions may be done to reduce cross-reactivity. Reduced cross-reactivity, although desirable, is not necessary to produce a product that may have advantages over the existing porcine factor VIII concentrate, which produces side effects due to contaminant porcine proteins and may produce untoward effects due to the immunogenicity of porcine factor VIII sequences. A hybrid human/other mammalian or porcine/other mammalian factor VIII molecule will not contain foreign porcine proteins. Additionally, the extensive epitope mapping accomplished in the porcine A2 domain indicates that greater than 95% of the therapeutic hybrid human/porcine factor VIII sequence will be human.

Preparation of hybrid factor VIII equivalents:

The methods for amino acid substitution in factor VIII molecules described above and in the examples can also be used to prepare procoagulant recombinant hybrid factor VIII equivalent molecules or fragments thereof comprising at least one amino acid sequence including one or more amino acids having no known amino acid sequence identity to factor VIII ("non-factor VIII sequence") substituted for at least one specific amino acid sequence that includes an antigenic and/or immunogenic site in human, animal, or hybrid factor VIII. The resulting active hybrid tractor VIII equivalent molecule has equal or less reactivity with factor VIII inhibitory antibodies and/or less immunogenicity in human and animals than the unsubstituted human, animal, or hybrid factor VIII.

Suitable amino acid residues that can be substituted for those sequences of amino acids critical to coagulant and/or antigenic and/or immunogenic activity in human or animal factor VIII or hybrid human/animal factor VIII to prepare a hybrid equivalent factor VIII molecule include any amino acids having no known sequence identity to animal or human factor VIII amino acid sequence that has coagulant, antigenic, or immunogenic activity. In a preferred embodiment, the amino acids that can be substituted include alanine residues using alanine scanning mutagenesis techniques.

Hybrid factor VIII equivalent molecules described herein also include those molecules in which amino acid residues having no known identity to animal factor VIII sequence are substituted for amino acid residues not critical to coagulant, antigenic, or immunogenic activity.

As described above, in one embodiment of a hybrid factor VIII equivalent molecule, the molecule has reduced cross-reactivity with inhibitor plasmas. One or more epitopes in the cross-reactive factor VIII are identified, as described above, and then replaced by non-factor VIII amino acid sequence, preferably alanine residues, using, for example, the alanine scanning mutagenesis method.

In a preferred embodiment, a procoagulant recombinant hybrid factor VIII equivalent molecule is prepared comprising at least one sequence including one or more amino acids having no known sequence identity to factor VIII, preferably alanine residues, substituted for at least one sequence including one or more amino acids including an epitope, and/or for at least one sequence including one or more amino acids including an immunogenic site, preferably in human factor VIII. The resulting hybrid equivalent factor VIII molecule or fragment thereof has reduced or no immunoreactivity with inhibitory antibodies to factor VIII and/or reduced or no immunogenicity in human or animals. The methods for identifying specific antigenic amino acid sequence in the A2 domain of human factor VIII for substitution by nonantigenic porcine unique amino acid sequence are described in Examples 7 and 8 and are exemplary for identifying antigenic sequence in the A2 and other domains of human and animal factor VIII and for using site-directed mutagenesis methods such as alanine scanning mutagenesis to substitute non-factor VIII amino acid sequence.

Since the human A2 epitope has been narrowed to 25 or fewer amino acids, as described in Example 8, alanine scanning mutagenesis can be performed on a limited number of hybrid factor VIII constructs having human amino acid sequence to determine which are procoagulant, non-immunoreactive and/or nonimmunogenic hybrid factor VIII constructs based on A2 amino acid substitutions. In the A2 domain, the most likely candidates for alanine substitutions to achieve both reduced antigenicity and immunogenicity in the hybrid construct are Arg484, Pro485, Tyr487, Ser488, Arg489, Pro492, Val495, Phe501, and Ile508. The binding affinity of a hybrid construct comprising each of these mutants for mAb413 and a panel of A2 specific patient IgGs will be determined by ELISA. Any mutant that is active and has a binding affinity for A2 inhibitors that is reduced by more than 2 orders of magnitude is a candidate for the A2 substituted factor VIII molecule. Constructs having more than one mutation will be selected, based on the assumption that the more the epitope is altered, the less immunogenic it will be. It is possible that there are other candidate residues in the region between Arg484-Ile508, since there may be key residues for the epitope that are common to both human and porcine factor VIII. For example, charged residues are frequently involved in protein-protein interactions, so an alanine substitution for Lys493 is a possible candidate.

This procedure will be carried out in the C2 epitope and the putative third epitope, which is thought to be in the A3 or C1 domains, as well as any other epitopes identified in factor VIII, to prepare hybrid equivalent factor VIII constructs.

Diagnostic Assays

The hybrid human/animal, animal/animal, or equivalent factor VIII cDNA and/or protein expressed therefrom, in whole or in part, can be used in assays as diagnostic reagents for the detection of inhibitory antibodies to human or animal factor VIII or to hybrid human/animal factor or equivalent VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the hybrid human/animal factor VIII that contains at least one antigenic site, wherein the amount is sufficient to form a detectable complex with the inhibitory antibodies in the sample.

Nucleic acid and amino acid probes can be prepared based on the sequence of the hybrid human/porcine, human/non-human, non-porcine mammalian, animal/animal, or equivalent factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with a hybrid human/animal or hybrid equivalent factor VIII. The cDNA probes can be used, for example, for research purposes in screening DNA libraries.

Pharmaceutical Compositions

Pharmaceutical compositions containing hybrid human/animal, porcine/non-human, non-porcine mammalian, animal-1/animal-2, or equivalent factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container in then swirled by hand to free lipid material from the sides of the container and to disperse lipid aggregates, thereby forming the liposomal suspension.

The hybrid factor or hybrid equivalent VIII can be combined with other suitable stabilization compounds, delivery vehicles, and/or carrier vehicles, including vitamin K dependent clotting factors, tissue factor, and von Willebrand factor (vWf) or a fragment of vwf that contains the factor VIII binding site, and polysaccharides such as sucrose.

Hybrid or hybrid equivalent factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, 29 Transfusion 812–820, 1989).

Hybrid factor VIII can be stored bound to vWf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of hybrid factor VIII. These methods include: (21) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid factor VIII has been indefinitely stable at 40° C. in 0.6M NaCl, 20 mM MES, and 5 mM $CaCl_2$ at pH 6.0 and also can be stored frozen in these buffers and thawed with minimal loss of activity.

Methods of Treatment

Hybrid or hybrid equivalent factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, hybrid or hybrid equivalent factor VIII can be administered by transplant of cells genetically engineered to produce the hybrid or by implantation of a device containing such cells, as described above.

In a preferred embodiment, pharmaceutical compositions of hybrid or hybrid equivalent factor VIII alone or in combination with stabilizers, delivery vehicles, and/or carriers are infused into patients intravenously according to the same procedure that is used for infusion of human or animal factor VIII.

The treatment dosages of hybrid or hybrid equivalent factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M., et al., 328 *New. Engl. J. Med.* 453–459 (1993); Pittman, D. D., et al., 79 *Blood* 389–397 (1992), and Brinkhous fit al., 82 *Proc, Natl. Acad. Sci.* 8752–8755 (1985).

Usually, the desired plasma factor VIII level to be achieved in the patient through administration of the hybrid or hybrid equivalent factor VIII is in the range of 30–100% of normal. In a preferred mode of administration of the hybrid or hybrid equivalent factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require more hybrid or hybrid equivalent factor VIII, or patients may require less hybrid or hybrid equivalent factor VIII because of its higher specific activity than human factor VIII or decreased antibody reactivity or immunogenicity. As in treatment with human or porcine factor VIII, the amount of hybrid or hybrid equivalent factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, hybrid or hybrid equivalent factor VIII can be administered subcutaneously or orally with liposomes in one or several doses at varying intervals of time.

Hybrid or hybrid equivalent factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

The hybrid or hybrid equivalent factor VIII molecule and the methods for isolation, characterization, making, and using it generally described above will be further understood with reference to the following non-limiting examples.

EXAMPLE 1
Assay of porcine factor VIII and hybrid human/porcine factor VIII

Porcine factor VIII has more coagulant activity than human factor VIII, based on specific activity of the molecule. These results are shown in Table III in Example 4. This conclusion is based on the use of appropriate standard curves that allow human and porcine factor VIII to be fairly compared. Coagulation assays are based on the ability of factor VIII to shorten the clotting time of plasma derived from a patient with hemophilia A. Two types of assays were employed: the one-stage and the two-stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15M NaCl, 0.02M HEPES, pH 7.4. The standard curve was constructed based on 3 or 4 dilutions of plasma, the highest dilution being 1/50, and on $log_{10}$ clotting time plotted against $log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor-VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2
Characterization of the functional difference between human and porcine factor VIII The isolation of porcine and human plasma-derived factor VIII and human recombinant factor VIII have been described in the literature in Fulcher, C. A., and T. S. Zimmerman, 79 *Proc. Natl. Acad. Sci. U.S.A.* 1648–1652 (1982); Toole, J. J., et al., 312 *Nature* 342–347 (1984) (Genetics Institute); Gitschier, J., et al., 3112 *Nature* 326–330 (1984) (Genentech); Wood, W. I., et al., 312 *Nature* 330–337 (1984) (Genentech); Vehar, G. A., et al., 312 *Nature* 337–342 (1984) (Genentech); Fass, D. N., et al., 59 *Blood* 594 (1982); Toole, J. J., et al., 83 *Proc. Nat'l. Acad. Sci. U.S.A.* 5939–5942 (1986). This can be accomplished in several ways. All these preparations are similar in subunit composition, although there is a functional difference in stability between human and porcine factor VIII.

For comparison of human recombinant and porcine factor VIII, preparations of highly-purified human recombinant factor VIII (Cutter Laboratories, Berkeley, Calif.) and porcine factor VIII (immunopurified as described in Fass, D. N., et al., 59 *Blood* 594 (1982)) were subjected to high-pressure liquid chromatography (HPLC) over a Mono Q™ (Pharmacia-LKB, Piscataway, N.J.) anion-exchange column (Pharmacia, Inc.). The purposes of the Mono Q™ HPLC step were elimination of minor impurities and exchange of human and porcine factor VIII into a common buffer for comparative purposes. Vials containing 1000–2000 units of factor VIII were reconstituted with 5 ml $H_2O$. Hepes (2M at pH 7.4) was then added to a final concentration of 0.02M. Factor VIII was applied to a Mono Q™ HR 5/5 column equilibrated in 0.15M NaCl, 0.02M Hepes, 5 mM $CaCl_2$, at pH 7.4 (Buffer A plus 0.15M NaCl); washed with 10 ml Buffer A+0.15M NaCl; and eluted with a 20 ml linear gradient, 0.15M to 0.90M NaCl in Buffer A at a flow rate of 1 ml/min.

For comparison of human plasma-derived factor VIII (purified by Mono Q™ HPLC) and porcine factor VIII, immunoaffinity-purified, plasma-derived porcine factor VIII was diluted 1:4 with 0.04M Hepes, 5 mM $CaCl_2$, 0.01% Tween-80, at pH 7.4, and subjected to Mono Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE
FACTOR VIII COAGULANT ACTIVITY

|  | Activity (U/$A_{280}$) |
| --- | --- |
| Porcine | 21,300 |
| Human plasma-derived | 3,600 |
| Human recombinant | 2,400 |

EXAMPLE 3

Comparison of the stability of human and porcine factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono Q™ HPLC-purified human factor VIII was activated with thrombin and subjected to Mono S™ cation-exchange (Pharmacia, Inc.) HPLC under conditions that produce stable porcine factor VIIIa, as described by Lollar, J. S., and C. G. Parker, 28 *Biochemistry* 666 (1989).

Human factor VIII, 43 μg/ml (0.2 μM) in 0.2M NaCl, 0.01M Hepes, 2.5 mM $CaCl_2$, at pH 7.4, in 10 ml total volume, was reacted with thrombin (0.036 μM) for 10 min, at which time FPR-$CH_2Cl$ D-phenyl-propyl-arginyl-chloromethyl ketone was added to a concentration of 0.2 μM for irreversible inactivation of thrombin. The mixture then was diluted 1:1 with 40 mM 2-(N-morpholino)ethane sulfonic acid (MES), 5 mM $CaCl_2$, at pH 6.0, and loaded at 2 ml/min onto a Mono S™ HR 5/5 HPLC column (Pharmacia, Inc.) equilibrated in 5 mM MES, 5 mM $CaCl_2$, at pH 6.0 (Buffer B) plus 0.1M NaCl. Factor VIIIa was eluted without column washing with a 20 ml gradient from 0.1M NaCl to 0.9M NaCl in Buffer B at 1 ml/min.

The fraction with coagulant activity in the two-stage assay eluted as a single peak under these conditions. The specific activity of the peak fraction was approximately 7,500 U/$A_{280}$. Sodium dodecyl sulfate-polyacrylamide gel electrophoresis (SDS-PAGE) of the Mono S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by Mono S™ HPLC under the same conditions had a specific activity 1.6×10$^6$ U/$A_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of Mono S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimetic factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S™ buffers to pH 5.Mono Q™-purified human factor VIII (0.5 mg) was diluted with $H_2O$ to give a final composition of 0.25 mg/ml (1 μM) factor VIII in 0.25M NaCl, 0.01M Hepes, 2.5 mM $CaCl_2$, 0.005% Tween-80, at pH 7.4 (total volume 7.0 ml). Thrombin was added to a final concentration of 0.072 μM and allowed to react for 3 min. Thrombin was then inactivated with FPR-$CH_2Cl$ (0.2 μM). Tile mixture then was diluted 1:1 with 40 mM sodium acetate, 5 mM $CaCl_2$, 0.01% Tween-80, at pH 5.0, and loaded at 2 ml/min onto a Mono S™ HR 5/5 HPLC column equilibrated in 0.01M sodium acetate, 5 mM $CaCl_2$, 0.01% Tween-80, at pH 5.0, plus 0.1M NaCl. Factor VIIIa was eluted without column washing with a 20 ml gradient from 0.1M NaCl to 1.0M NaCl in the same buffer at 1 ml/min. This resulted in recovery of coagulant activity in a peak that contained detectable amounts of the A2 fragment as shown by SDS-PAGE and silver staining. The specific activity of the peak fraction was ten-fold greater than that recovered at pH 6.0 (75,000 U/$A_{280}$ v. 7,500 U/$A_{280}$). However, in contrast to porcine factor VIIIa isolated at pH 6.0, which is indefinitely stable at 4° C., human factor VIIIa activity decreased steadily over a period of several hours after elution from Mono S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relatives stability of porcine factor VIIIa under certain conditions is because of stronger association of the A2 subunit.

EXAMPLE 4

Preparation of hybrid human/porcine factor VIII by reconstitution with subunits

Porcine factor VIII light chains and factor VIII heavy chains were isolated as follows. A 0.5M solution of EDTA at pH 7.4 was added to Mono Q™-purified porcine factor VIII to a final concentration of 0.05M and was allowed to stand at room temperature for 18–24 h. An equal volume of 10 mM histidine-Cl, 10 mM EDTA, 0.02% v/v Tween 80, at pH 6.0 (Buffer B), was added, and the solution was applied at 1 ml/min to a Mono S™ HR 5/5 column previously equilibrated in Buffer A plus 0.25M NaCl. Factor VIII heavy chains did not bind the resin, as judged by SDS-PAGE. Factor VIII light chain was eluted with a linear, 20 nil, 0.1–0.7M NaCl gradient in Buffer A at 1 ml/min and was homogeneous by SDS-PAGE. Factor VIII heavy chains were isolated by mono Q™ HPLC (Pharmacia, Inc., Piscataway, N.J.) in the following way. Factor VIII heavy chains do not adsorb to mono S™ during the purification of factor VIII light chains. The fall-through material that contained factor VIII heavy chains was adjusted to pH 7.2 by addition of 0.5M Hepes buffer, pH 7.4, and applied to a mono Q™ HR5/5 HPLC column (Pharmacia, Inc.) equilibrated in 0.1M NaCl, 0.02M Hepes, 0.01% Tween-80, pH 7.4. The column was washed with 10 ml of this buffer, and factor VIII heavy chains were eluted with a 20 ml 0.1–1.0M NaCl gradient in this buffer. Human light chains and heavy chains were isolated in the same manner.

Human and porcine light and heavy chains were reconstituted according to the following steps. Ten µl human or porcine factor VIII light chain, 100 µg/ml, was mixed in 1M NaCl, 0.02M Hepes, 5 mM $CaCl_2$, 0.01% Tween-80, pH 7.4, with (1) 25 µl heterologous heavy chain, 60 µg/ml, in the same buffer; (2) 10 µl 0.02M Hepes, 0.01% Tween-80, pH 7.4; (3) 5 µl 0.6M $CaCl_2$, for 14 hr at room temperature. The mixture was diluted ¼ with 0.02M MES, 0.01% Tween-80, 5 mM $CaCl_2$, pH 6, and applied to Mono S™ Hr5/5 equilibrated in 0.1M NaCl, 0.02M MES, 0.01% Tween-80, 5 mM $CaCl_2$, pH 6.0. A 20 ml gradient was run from 0.1–1.0M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds Mono S™; excess heavy chains ensure that free light chains are not part of the preparation. Reconstitution experiments followed by Mono S™ HPLC purification were performed with all four possible combinations of chains: human light chain/human heavy chain, human light chain/porcine heavy chain, porcine light chain/porcine heavy chain, porcine light chain/human heavy chain. Table III shows that human light chain/porcine heavy chain factor VIII has activity comparable to native porcine factor VIII (Table II), indicating that structural elements in the porcine heavy chain are responsible for the increased coagulant activity of porcine factor VIII compared to human factor VIII.

TABLE III

COMPARISON OF HYBRID HUMAN/PORCINE FACTOR VIII COAGULANT ACTIVITY WITH HUMAN AND PORCINE FACTOR VIII

| | Activity (U/$A_{280}$) |
|---|---|
| Porcine light chain/porcine heavy chain | 30,600 |
| Human light chain/porcine heavy chain | 44,100 |
| Porcine light chain/human heavy chain | 1,100 |
| Human light chain/human heavy chain | 1,000 |

EXAMPLE 5

Preparation of active hybrid human/porcine factor VIII by reconstitution with domains The porcine A1/A3-C1-C2 dimer, the porcine A2 domain, the human A1/A3-C1-C2 dimer, and the human A2 domain were each isolated from porcine or human blood, according to the method described in Lollar, P., et al., 267(33) *J. Biol. Chem*, 23652–23657 (Nov. 25, 1992). For example, to isolate the porcine A1/A3-C1-C2 dimer, porcine factor VIIIa (140 µg) at pH 6.0 was raised to pH 8.0 by addition of 5N NaOH for 30 minutes, producing dissociation of the A2 domain and 95 percent inactivation by clotting assay. The mixture was diluted 1:8 with buffer B (20 mM HEPES, 5 mM $CaCl_2$, 0.01 % Tween 80, pH 7.4) and applied to a monoS column equilibrated in buffer B. The A1/A3-C1-C2 dimer eluted as a single sharp peak at approximately 0.4M NaCl by using a 0.1–1.0M NaCl gradient in buffer B. To isolate the porcine A2 domain, porcine factor VIIIa was made according to the method of Lollar, P., and C. G. Parker, 28 *Biochem*. 666–674 (1989), starting with 0.64 mg of factor VIII. Free porcine A2 domain was isolated as a minor component (50 µg) at 0.3M NaCl in the monoS™ chromatogram.

Hybrid human/porcine factor VIII molecules were reconstituted from the dimers and domains as follows. The concentrations and buffer conditions for the purified components were as follows: porcine A2, 0.63 µM in buffer A (5 mM MES; 5 mM $CaCl_2$, 0.01% Tween 80, pH 6.0) plus 0.3M NaCl; porcine A1/A3-C1-C2, 0.27 µM in buffer B plus 0.4M NaCl, pH 7.4; human A2, 1 µM in 0.3M NaCl, 10 mM histidine-HCl, 5 mM $CaCl_2$, 0.01% Tween 20, pH 6.0; human A1/A3-C1-C2, 0.18 µM in 0.5M NaCl, 10 mM histidine-Cl, 2.5 mM $CaCl_2$, 0.1% Tween 20, pH 6.0. Reconstitution experiments were done by mixing equal volumes of A2 domain and A1/A3-C1-C2 dimer. In mixing experiments with porcine A1/A3-C1-C2 dimer, the pH was lowered to 6.0 by addition of 0.5M MES, pH 6.0, to 70 mM.

The coagulation activities of all four possible hybrid factor VIIIa molecules—[pA2/(hA1/A3-C1-C2)], [hA2/(pA1/A3-C1-C2)], [pA2/(pA1/pA3-C1-C2)], and [hA2/(hA1/A3-C1-C2)]—were obtained by a two-stage clotting assay at various times.

The generation of activity following mixing the A2 domains and A1/A3-C1-C2 dimers was nearly complete by one hour and was stable for at least 24 hours at 37° C. Table IV shows the activity of reconstituted hybrid factor VIIIa molecules when assayed at 1 hour. The two-stage assay, by which the specific activities of factor VIIIa molecules were obtained, differs from the one-stage assay, and the values cannot be compared to activity values of factor VIII molecules obtained by a one-stage assay.

TABLE IV

COMPARISON OF COAGULANT ACTIVITIES OF DOMAIN-SUBSTITUTED HYBRID HUMAN/PORCINE FACTOR VIIIa

| Hybrid fVIIIa | Specific Activity (U/mg) |
|---|---|
| Porcine A2 + Human A1/A3-C1-C2 | 140,000 |
| Porcine A2 + Porcine A1/A3-C1-C2 | 70,000 |
| Human A2 + Porcine A1/A3-C1-C2 | 40,000 |
| Human A2 + Human A1/A3-C1-C2 | 40,000 |

Table IV shows that the greatest activity was exhibited by the porcine A2 domain/human A1/A3-C1-C2 dimer, followed by the porcine A2 domain/porcine A1/A3-C1-C2 dimer.

Thus when the A2 domain of porcine factor VIIIa was mixed with the A1/A3-C1-C2 dimer of human factor VIIIa, coagulant activity was obtained. Further, when the A2 domain of human factor VIIIa was mixed with the A1/A3-C1-C2 dimer of porcine factor VIIIa, coagulant activity was obtained. By themselves, the A2, A1, and A3-C1-C2 regions have no coagulant activity.

EXAMPLE 6

Isolation and sequencing of the A2 domain of porcine factor VIII

Only the nucleotide sequence encoding the B domain and part of the A2 domain of porcine factor VIII has been sequenced previously (Toole, J. J., et al., 83 *Proc. Nat'l.*

Acad. Sci. U.S.A. 5939–5942 (1986)). The cDNA and predicted amino acid sequences (SEQ ID NOs: 3 and 4, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript™ (Stratagene) phagemid vector.

The porcine A2 domain was completely sequenced by dideoxy sequencing. The cDNA and predicted amino acid sequences are as described in SEQ ID NOs: 3 and 4, respectively.

EXAMPLE 7
Preparation of recombinant hybrid human/animal factor VIII

The nucleotide and predicted amino acid sequences (SEQ ID NOs:1 and 2, respectively) of human factor VIII have been described in the literature (Toole, J. J., et al., 312 *Nature* 342–347 (1984) (Genetics Institute); Gitschier, J., et al., 312 *Nature* 326–330 (1984) (Genentech); Wood, W. I., et al., 312 *Nature* 330–337 (1984) (Genentech); Vehar, G. A., et al., 312 *Nature* 337–342 (1984) (Genentech)).

Making recombinant hybrid human/animal factor VIII requires that a region of human factor VIII cDNA (Biogen Corp.) be removed and the animal cDNA sequence having sequence identity be inserted. Subsequently, the hybrid cDNA is expressed in an appropriate expression system. As an example, hybrid factor VIII cDNAs were cloned in which some or all of the porcine A2 domain was substituted for the corresponding human A2 sequences. Initially, the entire cDNA sequence corresponding to the A2 domain of human factor VIII and then a smaller part of the A2 domain was looped out by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989). The steps were as follows.

Materials.

Methoxycarbonyl-D-cyclohexylglycyl-glycl-arginine-p-nitroanilide (Spectrozyme™ Xa) and anti-factor VIII monoclonal antibodies ESH4 and ESH8 were purchased from American Diagnostica (Greenwich, Conn.). Unilamellar phosphatidylcholine/phosphatidylserine (75/25, w/w) vesicles were prepared according to the method of Barenholtz, Y., et al., 16 *Biochemistry* 2806–2810 (1977). Recombinant desulfatohirudin was obtained from Dr. R. B. Wallis, Ciba-Geigy Pharmaceuticals (Cerritos, Calif.). Porcine factors IXa, X, Xa, and thrombin were isolated according to the methods of Lollar, P., et al., 63 *Blood* 1303–1306 (1984), and Duffy, E. J., and P. Lollar, 207 *J. Biol. Chem.* 7621–7827 (1992). Albumin-free pure recombinant human factor VIII was obtained from Baxter-Biotech (Deerfield Ill.).

Cloning of the porcine factor VIII A2 domain.

The cDNA encoding the porcine A2 domain was obtained following PCR of reverse-transcribed porcine spleen mRNA isolated as described by Chomczyneki, P., and Sacohi, N., 162 *Anal. Biochem.* 156–159 (1987). cDNA was prepared using the first-strand cDNA synthesis kit with random hexamers as primers (Pharmacia, Piscataway, N.J.). PCR was carried out using a 5'-terminal degenerate primer 5' AARCAYCCNAARACNTGGG 3' (SEQ ID NO:11), based on known limited porcine A2 amino acid sequence, and a 3'-terminal exact primer, 5' GCTCGCACTAGGGGTCT-TGAATTC 3' (SEQ ID NO:12), based on known porcine DNA sequence immediately 3' of the porcine A2 domain. These oligonucleotides correspond to nucleotides 1186–1203 and 2289–2313 in the human sequence (SEQ ID NO:1). Amplification was carried out for 35 cycles (1 minute 94° C., 2 minutes 50° C., 2 minutes 72° C.) using Tag DNA polymerase (Promega Corp., Madison, Wis.). The 1.1-kilobase amplified fragment was cloned into pBluescript II KS-(Stratagene) at the EcoRV site using the T-vector procedure, as described by Murchuk, D., et al., 19 *Nucl. Acids Res.* 1154 (1991). *Escherichia coli* XL1-Blue-competent celia were transformed, and plasmid DNA was isolated. Sequencing was carried out in both directions using Sequenase™ version 2.0 (U.S. Biochemical Corp., a Division of Amersham LifeScience, Inc., Arlington Hts, Ill.). This sequence was confirmed by an identical sequence that was obtained by direct sequencing of the PCR product from an independent reverse transcription of spleen RNA from the same pig (Circumvent™, New England Biolabs,. Beverly, Mass.). The region containing the epitope for autoantibody RC was identified as 373–536 in human factor VIII (SEQ ID NO:2).

Construction and expression of a hybrid human/porcine factor VIII cDNA.

B-domainless human factor VIII (HB-, from Biogen, Inc. Cambridge, Mass.), which Lacks sequences encoding for amino acid residues 741–1648 (SEQ ID NO:2), was used as the starting material for construction of a hybrid human/porcine factor VIII. HB- was cloned into the expression vector ReNeo. To facilitate manipulation, the cDNA for factor VIII was isolated as a XhoI/HpaI fragment from ReNeo and cloned into Xho1/EcoRV digested pBlueSsript II KS. An oligonucleotide, 5' CCTTCCTTTATCCAAATACG-TAGATCAAGAGGAAATTGAC 3' (SEQ ID NO:7), was used in a site-directed mutagenesis reaction using uracil-containing phage DNA, as described by Kunkel, T. A., et al., 204 *Meth. Enzymol.* 125–139 (1991), to simultaneously loop-out the human A2 sequence (nucleotides 1169–2304 in SEQ ID NO:1) and introduce a SnaBI restriction site. The A2-domainless human factor VIII containing plasmid was digested with SnaBI followed by addition of ClaI linkers. The porcine A2 domain was then amplified by PCR using the phosphorylated 5' primer 5' GTAGCGTTGCCAA-GAAGCACCCTAAGACG 3' (SEQ ID NO:8) and 3' primer 5' GAAGAGTAGTACGAGT-TATTTCTCTGGGTTCAATGAC 3' (SEQ ID NO:9), respectively. ClaI linkers were added to the PCR product followed by ligation into the human factor VIII-containing vector. The A1/A2 and A2/A3 junctions were corrected to restore the precise thrombin cleavage and flanking sequences by site-directed mutagenesis using the oligonucleotide shown in SEQ ID NO:8 and nucleotides 1–22 (5' GAA . . . TTC in SEQ ID NO:9) to correct the 5'- and 3'-terminal junctions, respectively. I:n the resulting construct, designated HP1, the human A2 domain was exactly substituted with the porcine A2 domain. A preliminary product contained an unwanted thymine at the A1-A2 junction as a result of the PCR amplification of the porcine A2 domain. This single base can be looped out by use of the mutagenic oligonucleotide 5' CCTTTATCCAAATACGTAGCGTTTGCCAAGAAG, 3' (SEQ ID NO:10).

A region containing 63% of the porcine NH$_2$-terminal A2 domain, which encompasses the putative A2 epitope, was substituted for the homologous human sequence of B-domainless cDNA by exchanging SpeI/BamHI fragments between the pBluescript plasmids containing human factor VIII and human/porcine A2 factor VIII cDNA. The sequence was confirmed by sequencing the A2 domain and splice sites. Finally, a SpeI/ApaI fragment, containing the entire A2 sequence, was substituted in place of the corresponding sequence in HB-, producing the HP2 construct.

Preliminary expression of HB- and HP2 in COS-7 cells was tested after DEAE-dextran-mediated DNA transfection, as described by Seldon, R. F., in *current Protocols in Molecular Biology* (Ausubel, F. M., et al., eds), pp. 9.21–9.26, Wiley Interscience, N.Y. After active factor VIII expression was confirmed and preliminary antibody inhibition studies were done, HB- and HP2 DNA were then stably transfected into baby hamster kidney cells using liposome-mediated transfection (Lipofectin®, Life Technologies, Inc., Gaithersburg, Md.). Plasmid-containing clones were selected for G418 resistance in Dulbecco's modified Eagle's medium-F12, 10% fetal calf serum (DMEM-F12/10% fetal calf serum) containing 400 µg/ml G418 followed by maintenance in DMEM-F12/10% fetal calf serum containing 100 µg/ml G418. Colonies showing maximum expression of HB- and HP2 factor VIII activity were selected by ring cloning and expanded for further characterization.

HB- and HP2 factor VIII expression was compared by plasma-free factor VIII assay, one-stage clotting assay, and enzyme-linked immunosorbent assay using purified recombinant human factor VIII as a standard. Specific coagulant activities of 2600 and 2580 units/mg were obtained for HB- and HP2, respectively. HB- and HP2 produced 1.2 and 1.4 units/ml/48 hours/$10^7$ cells, respectively. This is identical to that of the wild type construct (2,600±200 units/mg). The specific activities of HB- and HP2 were indistinguishable in the plasma-free factor VIII assay.

Construction and expression of hybrid human/non-human, non-porcine mammalian and hybrid equivalent factor VIII.

Cloning of other animal A1, A3, C1, and C2 domains and part domains is feasible with the same strategy that was used for cloning the porcine A2 domain. Fragments of these domains can be cloned by the looping out mutagenesis technique. Excision of the corresponding domains in human factor VIII and any fragments thereof, including single amino acid eliminations, is feasible by looping out mutagenesis as described above. All possible domain replacements, fragments of domain replacements, or single amino acid residue replacements are possible by this approach combined with site-directed mutagenesis techniques, such as splicing by overlap extension and alanine scanning mutagenesis.

The biological activity of recombinant hybrid human/animal and equivalent factor VIII with A1, A2, A3, C1, and/or C2 domain substitutions can be evaluated initially by use of a COS-cell mammalian transient expression system. Hybrid human/animal and equivalent cDNA can be transfected into COS cells, and supernatants can be analyzed for factor VIII activity by use of one-stage and two-stage coagulation assays as described above. Additionally, factor VIII activity can be measured by use of a chromogenic substrate assay, which is more sensitive and allows analysis of larger numbers of samples. Similar assays are standard in the assay of factor VIII activity (Wood, W. I., et al., 312 *Nature* 330–337, 1984; Toole, J. J., et al., 312 *Nature* 342–347, 1984). Expression of recombinant factor VIII in COS cells is also a standard procedure (Toole, J. J., et al., 312 *Nature* 342–347, 1984; Pittman, D. D., and R. J. Kaufman, 85 *Proc. Nat'l. Acad. Sci. U.S.A.* 2429–2433, 1988). The human factor VIII cDNA used as starting material for the recombinant molecules described herein has been expressed in COS cells yielding a product with biological activity. This material, as described above, can be used as a standard to compare hybrid human/animal factor VIII molecules. The activity in the assays is converted to a specific activity for proper comparison of the hybrid molecules. For this, a measurement of the mass of factor VIII produced by the cells is necessary and can be done by immunoassay with purified human and/or animal factor VIII as standards. Immunoassays for factor VIII are routine for those skilled in the art (See, e.g., Lollar, P., et al., 71 *Blood* 137–143, 1988).

EXAMPLE 8

Determination of inhibitory activity in hybrid human/animal and equivalent factor VIII Sequences of human and animal factor VIII likely to be involved as epitopes (i.e., as recognition sites for inhibitory antibodies that react with factor VIII) can be determined using routine procedures, for example through use of assay with antibodies to factor VIII combined with site directed mutagenesis techniques such as splicing by overlap extension methods (SOE), as shown below. Sequences of animal factor VIII that are not antigenic compared to corresponding antigenic human sequences can be identified, and substitutions can be made to insert animal sequences and delete human sequences according to standard recombinant DNA methods. Sequences of amino acids such as alanine residues having no known sequence identity to factor VIII can also be substituted by standard recombinant DNA methods or by alanine scanning mutagenesis. Porcine factor VIII reacts less than human factor VIII with some inhibitory antibodies; this provides a basis for current therapy for patients with inhibitors. After the recombinant hybrids are made, they can be tested in vitro for reactivity with routine assays, including the Bethesda inhibitor assay. Those constructs that are less reactive than native human factor VIII and native animal factor VIII are candidates for replacement therapy.

The epitopes to which most, if not all, inhibitory antibodies reactive with human factor VIII are directed are thought to reside in two regions in the 2332 amino acid human factor VIII molecule, the A2 domain (amino acid residues 373–740) and the C2 domain (amino acid residues 2173–2332, both sequences shown in SEQ ID NO:2). The A2 epitope has been eliminated by making a recombinant hybrid human/porcine factor VIII molecule in which part of the human A2 domain is replaced by the porcine sequence having sequence identity to the replaced human amino acid sequence. This was accomplished, as described in Example 7, by clonirg the porcine A2 domain by standard molecular biology techniques and then cutting and splicing within the A2 domain using restriction sites. In the resulting construct, designated HP2, residues 373–604 (SEQ ID NO:4) of porcine factor VIII were substituted into the human A2 domain. HP2 was assayed for immunoreactivity with anti-human factor VIII antibodies using the following methods.

Factor VIII enzyme-linked immunosorbent assay.

Microtiter plate wells were coated with 0.15 ml of 6 μg/ml ESH4, a human factor VIII light-chain antibody, and incubated overnight. After the plate was washed three times with $H_2O$, the wells were blocked for 1 hour with 0.15M NaCl, 10 mM sodium phosphate, 0.05% Tween 20, 0.05% nonfat dry milk, 0.05% sodium azide, pH 7.4. To increase sensitivity, samples containing factor VIII were activated with 30 nM thrombin for 15 minutes. Recombinant desulfatohirudin then was added at 100 nM to inhibit thrombin. The plate was washed again and 0.1 ml of sample or pure recombinant human factor VIII (10–600 ng/ml), used as the standard, were added. Following a 2 hour incubation, the plate was washed and 0.1 ml of biotinylated ESH8, another factor VIII light-chain antibody, was added to each well. ESH8 was biotinylated using the Pierce sulfosuccinimidyl-6-(biotinamide)hexanoate biotinylation kit. After a 1 hour incubation, the plate was washed and 0.1 ml of strepavidin alkaline phosphatase was added to each well. The plate was developed using the Bio-Rad alkaline phosphatase substrate reagent kit, and the resulting absorbance at 405 nm for each well was determined by using a Vmax microtiter plate reader (Molecular Devices, Inc., Sunnyville, Calif.). Unknown factor VIII concentrations were determined from the linear portion of the factor VIII standard curve.

Factor VIII assays.

HB- and HB2 factor VIII were measured in a one-stage clotting assay, which was performed as described above (Bowie, E. J. W., and C. A. Owen, in Disorders of Hemostasis (Ratnoff and Forbes, eds) pp. 43–72, Grunn & Stratton, Inc., Orlando, Fla. (1984)), or by a plasma-free assay as follows. HB- or HP2 factor VIII was activated by 40 nM thrombin in 0.15M NaCl, 20 nM HEPES, 5 mM $CaCl_2$, 0.01% Tween 80, pH 7.4, in the presence of 10 nM factor IXa, 425 nM factor X, and 50 $\mu$M unilamellar phosphatidylserine/phosphatidylcholine (25/75, w/w) vesicles. After 5 minutes, the reaction was stopped with 0.05M EDTA and 100 nM recombinant desulfatohirudin, and the resultant factor Xa was measured by chromogenic substrate assay, according to the method of Hill-Eubanks, D. C., and P. Lollar, 265 *J. Biol. Chem.* 17854–17858 (1990). Under these conditions, the amount of factor Xa formed was linearly proportional to the starting factor VIII concentration as judged by using purified recombinant human factor VIII (Baxter Biotech, Deerfield, Ill.) as the standard.

Prior to clotting assay, HB- or HP2 factor VIII were concentrated from 48 hour conditioned medium to 10–15 units/ml by heparin-Sepharose™ chromatography. HB- or HP2 factor VIII were added to hemophilia A plasma (George King Biomedical) to a final concentration of 1 unit/ml. Inhibitor titers in RC or MR plasma or a stock solution of mAb 413 IgG (4 $\mu$M) were measured by the Bethesda assay as described by Kasper, C. K., et al., 34 *Thromb. Diath. Haemorrh.* 869–872 (1975). Inhibitor IgG was prepared as described by Leyte, A., et al., 266 *J. Biol, Chem.* 740–746 (1991).

HP2 does not react with anti-A2 antibodies Therefore, residues 373–603 must contain an epitope for anti-A2 antibodies.

Preparation of hybrid human/porcine factor VIII and assay by splicing by overlap extension (SOE).

Several more procoagulant recombinant hybrid human/porcine factor VIII B-domainless molecules with porcine amino acid substitutions in the human A2 region have been prepared to further narrow the A2 epitope. Besides restriction site techniques, the "splicing by overlap extensions " method (SOE) as described by Ho, S. N., et al., 77 *Gene* 51–59 (1989), has been used to substitute any arbitrary region of porcine factor VIII cDNA. In SOE, the splice site is defined by overlapping oligonucleotides that can be amplified to produce the desired cDNA by PCR. Ten cDNA constructs, designated HP4 through HP13, have been made. They were inserted into the ReNeo expression vector, stably transfected into baby hamster kidney cells, and expressed to high levels [0.5–1 $\mu$g (approximately 3–6 units)/$10^7$ cells/24 hours, as described in Example 7. Factor VIII coagulant activity was determined in the presence and absence of a model murine monoclonal inhibitory antibody specific for the A2 domain, mAb413. In the absence of inhibitor, all of the constructs had a specific coagulant activity that was indistinguishable from B(−) human factor VIII.

The hybrid human/porcine factor VIII constructs were assayed for reactivity with the anti-A2 inhibitor mAb413 using the Bethesda assay (Kasper, C. K., et al., 34 *Thromb. Diath. Haemorrh.* 869–872 (1975)). The Bethesda unit (BU) is the standard method for measuring inhibitor titers. The results are shown in Table V, and are compared to recombinant human factor VIII.

TABLE V

COMPARISON OF IMMUNOREACTIVITY OF AMINO ACID-SUBSTITUTED HYBRID HUMAN/PORCINE FACTOR VIII

| Construct | Porcine Substitution | Inhibition mAb413 (BU/mg IgG) |
|---|---|---|
| Human B(−) fVIII | None | 1470 |
| HP4 | 373–540 | <0.7 |
| HP5 | 373–508 | <0.7 |
| HP6 | 373–444 | 1450 |
| HP7 | 445–508 | <0.7 |
| HP8 | 373–483 | 1250 |
| HP9 | 484–508 | <0.7 |
| HP10 | 373–403 | 1170 |
| HP11 | 404–508 | <0.7 |
| HP12 | 489–508 | <0.7 |
| HP13 | 484–488 | <0.7 |

The boundaries of porcine substitutions are defined by the first amino acids that differ between human and porcine factor VIII at the $NH_2$-terminal and C-terminal ends of the insertion. As shown in Table V, if the Bethesda titer is not measurable (<0.7 BU/mg IgG), then an A2 epitope lies in the region of substituted porcine sequence. The epitope has been progressively narrowed to residues 484–509 (SEQ ID NO:2), consisting of only 25 residues, as exemplified by non-reactivity of mAb413 with HP9. Among constructs HP4 through HP11, HP9 was the most "humanized" construct that did not react with the inhibitor. This indicates that a critical region in the A2 epitope is located within the sequence Arg484-Ile508.

Based on a comparison between human and porcine factor VIII of the amino acid sequence in this critical region, two more constructs, HP12 and HP13, were made, in which corresponding porcine amino acid sequence was substituted for human amino acids 489–508 and 484–488, respectively. Neither reacts with mAb413. This indicates that residues on each side of the Arg488-Ser489 bond are important for reaction with A2 inhibitors. In HP12 only 5 residues are non-human, and in HP13 only 4 residues are non-human. The 484–508, 484–488, and 489–508 porcine substituted hybrids displayed decreased inhibition by A2 inhibitors from four patient plasmas, suggesting that there is little variation in the structure of the A2 epitope according to the inhibitor population response.

The reactivity of the most humanized constructs, HP9, HP12, and HP13, with two anti-A2 IgG5 preparations prepared from inhibitor plasmas was determined. Like mAb413, these antibodies did not react with HP9, HP12, and HP13, but did react with the control constructs HB(−) and HP8.

The region between 484–508 can be further analyzed for final identification of the critical A2 epitope, using the same procedures.

The methods described in Examples 7 and 8 can be used to prepare other hybrid human/non-porcine mammalian factor VIII with amino acid substitution in the human A2 or other domains, hybrid human/animal or animal/animal factor VIII with amino acid substitution in any domain, or hybrid factor VII equivalent molecules or fragments of any of these, such hybrid factor VIII having reduced or absent immunoreactivity with anti-factor VIII antibodies.

EXAMPLE 9

Elimination of human factor VIII A2 inhibitor reactivity by site-directed mutagenesis Example 8 showed that substitution of the porcine sequence bounded by residues 484 and 508 into the human factor VIII A2 domain yields a molecule that has markedly decreased reactivity with a panel of A2-specific factor VIII inhibitors (see also Healey et al. *J. Biol. Chem.* 270, 14505–14509, 1995). In this region, there are 9 amino acid differences between human and porcine factor VIII. These nine residues in human B-domainless factor VIII, R484, P485, Y487, P488, R489, P492, V495, F501, and I508 (using the single letter amino code), were individually changed to alanine by site-directed mutagenesis. Additionally, Mlu1 and Sac2 restriction sites were placed in the factor VIII cDNA at sites 5' and 3' relative to the A2 epitope, without changing the amino acids corresponding to these sites, to facilitate cloning. The nine mutants were stably transfected into baby hamster kidney cells and expressed to high levels. All nine produced biologically active factor VIII. They were partially purified and concentrated by heparin-Sepharose chromatography as described by Healey et al.

The mutants have been characterized by their reactivity with the murine monoclonal inhibitor MAb413 as in Example 7. This inhibitor recognizes the same or a very closely clustered epitope in the A2 domain as all human inhibitors studied to date. Inhibitor reactivity was measured using the Bethesda assay. Briefly, the Bethesda titer of an inhibitor is the dilution of inhibitor that inhibits factor VIII by 50% in a standard one-stage factor VIII clotting assay. For example, if solution of antibody is diluted 1/420 and it inhibits the recombinant factor VIII test sample by 50%, the Bethesda titer is 420 U. In the case of a pure monoclonal like MAb413, the mass of antibody is known, so the results are expressed in Bethesda units (BU) per mg MAb413. To find the 50% inhibition point, a range of dilutions of MAb413 was made and 50% inhibition was found by a curve fitting procedure. The results are as follows:

TABLE VI

| Mutation | MAb413 titer (BU/mg) | Reactivity* % |
|---|---|---|
| Wild-type, B(−) fVIII | 9400 | — |
| R484 → A | 160 | 1.7 |
| P485 → A | 4000 | 42 |
| Y487 → A | 50 | 0.53 |
| P488 → A | 3500 | 37 |
| R489 → A | 1.6 | 0.015 |
| P492 → A | 630 | 6.7 |
| V495 → A | 10700 | 113 |
| F501 → A | 11900 | 126 |
| I508 → A | 5620 | 60 |

*Relative to wild-type

These results indicate that it is possible to reduce the antigenicity of factor VIII toward the model A2 inhibitor by over a factor of 10 by making alanine substitutions at positions 484, 487, 489, and 492. The reactivity of R489→A is reduced by nearly 4 orders of magnitude. Any of these alanine substitutions can be therapeutically useful to reduce the antigenicity and the immunogenicity of factor VIII.

The results confirm the efficacy of alanine-scanning mutagenesis and further demonstrate that biological activity is retained even though the amino acid sequence has been altered within an epitope reactive to an inhibitory antibody. Five of the nine sites where the human and porcine sequences differ are also sites where the human and murine sequences differ. The factor VIIIs having alanine substitutions at these positions are therefore examples of a hybrid factor VIII equivalent molecule having a sequence with no known sequence identify with any presently known mammalian factor VIII.

Further modification, e.g. by combining two alanine substitutions, can also provide greatly reduced antigenicity for a wider range of patients, since polyclonal variant antibodies differing from patient to patient can react with variants of the factor VIII A2 epitope. In addition, immunogenicity (the capacity to induce antibodies) is further reduced by incorporation of more than one amino acid substitution. Such substitutions can include both alanine, porcine-specific amino acids, or other amino acids known to have low immunogenic potential. The substitutions at positions 495 and 501 are likely to be useful in reducing immunogenicity. In addition, these substitutions are likely to reduce reactivity to certain patient antibodies.

Other effective, antigenicity-reducing amino acid substitutions, besides alanine, can be made as long as care is taken to avoid those previously noted as being major contributors to antigen-antibody binding energy, or having bulky or charged side chains. Amino acids whose substitutions within an epitope reduce the antigenic reactivity thereof are termed "immunoreactivity-reducing" amino acids herein. Besides alanine, other immunoreactivity-reducing amino acids include, without limitation, methionine, leucine, serine and glycine. It will be understood that the reduction of immunoreactivity achievable by a given amino acid will also depend on any effects the substitution may have on protein conformation, epitope accessibility and the like.

EXAMPLE 10

Klenow fragment, phosphorylated ClaI linkers, NotI linkers, T4 ligase, and Taq DNA polymerase were purchased from Promega (Madison, Wisconsin). Polynucleotide kinase was purchased from Life Technologies, Inc., Gaithersburg, Md. $\gamma^{32}$P-ATP (Redivue, >5000 Ci/mmol) was purchased from Amersham. pbluescript II KS- and *E. coli* Epicurean XL1-Blue cells were purchased from Stratagene (La Jolla, Calif.). Synthetic oligonucleotides were purchased from Life Technologies, Inc. or Cruachem, Inc. 5'-phosphorylated primers were used when PCR products were produced for cloning purposes. Nucleotide (nt) numbering of oligonucleotides used as primers for polymerase chain reaction (PCR) amplification of porcine fVIII cDNA or genomic DNA uses the human fVIII cDNA as reference (Wood et al. (1984) supra).

Porcine spleen total RNA was isolated by acid guanidinium thiocyanate-phenol-chloroform extraction (Chomczynski, P. and N. Sacchi (1987) *Anal. Biochem.* 162:156–159). Porcine cDNA was prepared from total spleen RNA using Moloney murine leukemia virus reverse transcriptase (RT) and random hexamers to prime the reaction (First-Strand cDNA Synthesis Kit, Pharmacia Biotech) unless otherwise indicated. RT reactions contained 45 mM Tris-Cl, pH 8.3, 68 mM KCl, 15 mM DTT, 9 mM $MgCl_2$, 0.08 mg/ml bovine serum albumin and 1.8 mM deoxynilcleotide triphosphate (dNTP). Porcine genomic DNA was isolated from spleen using a standard procedure (Strauss, W. M. (1995) In Current Protocols in *Molecular Biology*, F. M. Ausubel et al., editors, John Wiley & Sons, pp. 2.2.1–2.2.3). Isolation of DNA from agarose gels was done using Geneclean II (Bio 101) or Quiex II Gel Extraction Kit (Qiagen).

PCR reactions were done using a Hybaid OmniGene thermocycler. For PCR reactions employing Taq DNA polymerase, reactions included 0.6 mM $MgCl_2$, 0.2 mM dNTPs, 0.5 μM oligonucleotide primers, 50 U/ml polymerase and 0.1 volume of first strand cDNA reaction mix. Except where indicated otherwise, PCR products were gel purified, blunt-ended with Klenow fragment, precipitated with ethanol, and either ligated to the EcoRV site of dephosphorylated pBluescript II KS- or ligated with phosphorylated ClaI linkers using T4 ligase, digested with ClaI, purified by Sephacryl S400 chromatography, and ligated to ClaI-cut, dephosphorylated pBluescript II KS-. Ligations were done using T4 DNA ligase (Rapid DNA ligation kit, Boehringer Mannheim) except where indicated otherwise. Insert-containing pBluescript II KS- plasmids were used to transform *E. coli* Epicurean XL1-Blue cells.

Sequencing of plasmid DNA was done using an Applied Biosystems 373a automated DNA sequencer and the PRISM dye terminator kit or manually using Sequenase v. 2.0 sequencing kit (Amersham Corporation). Direct sequencing of PCR products, including $^{32}$P-end labelling of oligonucleotides was done using a cycle sequencing protocol (dsDNA Cycle Sequencing System, Life Technologies).

Isolation of porcine fVIII cDNA clones containing 5' UTR sequence, signal peptide and A1 domain codons. The porcine fVIII cDNA 5' to the A2 domain was amplified by nested RT-PCR of female pig spleen total RNA using a 5' rapid amplification of cDNA ends (5'-RACE) protocol (Marathon cDNA Amplification, Clontech, Version PR55453). This included first strand cDNA synthesis using a lock-docking oligo(dT) primer (Borson, N. D. et al. (1992) PCR Methods Appl. 2:144–148), second strand cDNA synthesis using *E. coli* DNA polymerase I, and ligation with a 5' extended double stranded adaptor, SEQ ID NO:13 5'-CTA ATA CGA CTC ACT ATA GGG CTC GAG CGG CCG CCC GGG CAG GT-3 3'-$H_2N$-CCCGTCCA-$PO_4$-5' whose short strand was blocked at the 3' end with an amino group to reduce non-specific PCR priming and which was complementary to the 8 nucleotides at the 3' end (Siebert, P. D., et al. (1995) *Nucleic. Acids. Res.* 23:1087–1088). The first round of PCR was done using an adaptor-specific oligonucleotide, SEQ ID NO:14 5'-CCA TCC TAA TAC GAC TCA CTA TAG GGC-3' (designated AP1) as sense primer, and a porcine fVIII A2 domain specific oligonucleotide SEQ ID NO:15 5'-CCA TTG ACA TGA AGA CCG TTT CTC-3' (nt 2081–2104) as antisense primer. The second round of PCR was done using a nested, adaptor-specific oligonucleotide, SEQ ID NO:16 5'-ACT CAC TAT AGG GCT CGA GCG GC-3' (designated AP2) as sense primer, and a nested, porcine A2 domain-specific oligonucleotide SEQ ID NO:17 5'-GGG TGC AAA GCG CTG ACA TCA GTG-3' (nt 1497–1520) as antisense primer. PCR was carried out using a commercial kit (Advantage cDNA PCR core kit) which employs an antibody-mediated hot start protocol (Kellogg, D. E. et al. (1994) *BioTechniques* 16:1134–1137). PCR conditions included denaturation at 94° C. for 60 sec, followed by 30 cycles (first PCR) or 25 cycles (second PCR) of denaturation for 30 sec at 94° C., annealing for 30 sec at 60° C. and elongation for 4 min at 68° C. using tube temperature control. This procedure yielded a prominent ≈1.6 kb product which was consistent with amplification of a fragment extending approximately 150 bp into the 5' UTR. The PCR product was cloned into pBluescript using ClaI linkers. The inserts of four clones were sequenced in both directions.

The sequence of these clones included regions corresponding to 137 bp of the 5' UTR, the signal peptide, the A1 domain and part of the A2 domain. A consensus was reached in at least 3 of 4 sites. However, the clones contained an average of 4 apparent PCR-generated mutations, presumably due to the multiple rounds of PCR required to generate a clonable product. Therefore, we used sequence obtained from the signal peptide region to design a sense strand phosphorylated PCR primer, SEQ ID NO:18 5'-CCT CTC GAG CCA CCA TGT CGA GCC ACC ATG CAG CTA GAG CTC TCC ACC TG-3', designated RENEOPIGSP, for synthesis of another PCR product to confirm the sequence and for cloning into an expression vector. The sequence in bold represents the start codon. The sequence 5' to this represents sequence identical to that 5' of the insertion site into the mammalian expression vector ReNeo used for expression of fVIII (Lubin et al (1994) supra). This site includes an Xho1 cleavage site (underlined). RENEOPIGSP and the nt 1497–1520 oligonucleotide were used to prime a Taq DNA polymerase-mediated PCR reaction using porcine female spleen cDNA as a template. DNA polymerases from several other manufacturers failed to yield a detectable product. PCR conditions included denaturation at 94° C. for four min, followed by 35 cycles of denaturation for 1 min at 94° C., annealing for 2 min at 55° C. and elongation for 2 min at 72° C., followed by a final elongation step for 5 min at 72° C. The PCR product was cloned into pBluescript using ClaI linkers. The inserts of two of these clones were sequenced in both directions and matched the consensus sequence.

Isolation of porcine fvIII cDNA clones containing A3, C1 and 5' half of the C2 domain codons. Initially, two porcine spleen RT-PCR products, corresponding to a B-A3 domain fragment (nt 4519–5571) and a C1-C2 domain fragment (nt 6405–6990) were cloned. The 3' end of the C2 domain that was obtained extended into the exon 26 region, which is the terminal exon in fVIII. The B-A3 product was made using the porcine-specific B domain primer, SEQ ID NO:19 5' CGC GCG GCC GCG CAT CTG GCA AAGCTG AGT T 3', where the underlined region corresponds to a region in porcine fVIII that aligns with nt 4519–4530 in human fVIII. The 5' region of the oligonucleotide includes a NotI site that was originally intended for cloning purposes. The antisense primer used in generating the B-A3 product, SEQ ID NO:20 5'-GAA ATA AGC CCA GGC TTT GCA GTC RAA-3' was based on the reverse complement of the human fVIII cDNA sequence at nt 5545–5571. The PCR reaction contained 50 mM KCl, 10 mM Tris-Cl, pH 9.0, 0.1% Triton X-100, 1.5 mM $MgCl_2$, 2.5 mM dNTPs, 20 μM primers, 25 units/ml Taq DNA polymerase and 1/20 volume of RT reaction mix. PCR conditions were denaturation at 94° C. for 3 min, followed by 30 cycles of denaturation for 1 min at 94° C., annealing for 2 min at 50° C. and elongation for 2 min at 72° C. The PCR products were phosphorylated using T4 DNA kinase and NotI linkers were added. After cutting with NotI, the PCR fragments were cloned into the NotI site of BlueScript II KS- and transformed into XL1-Blue cells.

The C1-C2 product was made using the known human cDNA sequence to synthesize sense and antisense primers, SEQ ID NO:21 5'-AGG AAA TTC CAC TGG AAC CTT N-3' (nt 6405–6426) and SEQ ID NO:22 5'-CTG GGG GTG AAT TCG AAG GTA GCG N-3' (reverse complement of nt 6966–6990), respectively. PCR conditions were identical to those used to generate the B-A2 product. The resulting fragment was ligated to the pNOT cloning vector using the Prime PCR Cloner Cloning System (5 Prime-3 Prime, Inc., Boulder, Colorado) and grown in JM109 cells.

The B-A3 and C1-C2 plasmids were partially sequenced to make the porcine-specific sense and antisense oligonucleotides, SEQ ID NO:23 5'-GAG TTC ATC GGG AAG ACC TGT TG-3' (nt 4551–4573) and SEQ ID NO:24 5'-ACA GCC CAT CAA CTC CAT GCG AAG-3' (nt 6541–6564), respectively. These oligonucleotides were used as primers to generate a 2013 bp RT-PCR product using a Clontech Advantage cDNA PCR kit. This product, which corresponds to human nt 4551–6564, includes the region corresponding to the light chain activation peptide (nt 5002–5124), A3 domain (nt 5125–6114) and most of the C1 domain (nt 6115–6573). The sequence of the C1-C2 clone had established that human and porcine cDNAs from nt 6565 to the 3' end of the C1 domain were identical. The PCR product cloned into the EcoRV site of pBluescript II KS-. Four clones were completely sequenced in both directions. A consensus was reached in at least 3 of 4 sites.

Isolation of porcine fVIII cDNA clones containing the 3' half of the C2 domain codons. The C2 domain of human fVIII (nucleotides 6574–7053) is contained within exons 24–26 (Gitschier, J. et al. (1984) Nature 312:326–330). Human exon 26 contains 1958 bp, corresponding nucleotides 6901–8858. It includes 1478 bp of 3' untranslated sequence. Attempts to clone the exon 26 cDNA corresponding to the 3' end of the C2 domain and the 3'UTR by 3' RACE (Siebert et al. (1995) supra), inverse PCR (Ochman, H. et al. (1990) Biotechnology (N.Y). 8:759–760), restriction site PCR (Sarkar, G. et al. (1993) PCR Meth. Appl. 2:318–322), "unpredictably primed" PCR (Dominguez, O. and C. Lopez-Larrea (1994) Nucleic. Acids Res. 22:3247–3248) and by screening a porcine liver cDNA library failed. 3' RACE was attempted using the same adaptor-ligated double stranded cDNA library that was used to successfully used to clone the 5' end of the porcine fVIII cDNA. Thus, the failure of this method was not due to the absence of cDNA corresponding to exon 26.

A targeted gene walking PCR procedure (Parker, J. D. et al. (1991) Nucleic. Acids. Res. 19:3055–3060) was used to clone the 3' half of the C2 domain. A porcine-specific sense primer, SEQ ID NO:25 5'-TCAGGGCAATCAGGACTCC-3' (nt 6904–6924) was synthesized based on the initial C2 domain sequence and was used in a PCR reaction with nonspecific "walking" primers selected from oligonucleotides available in the laboratory. The PCR products were then targeted by primer extension analysis (Parker, J. D. and G. C. Burmer (1991) BioTechniques 10:94–101) using a $^{32}$P-end labelled porcine-specific internal primer, SEQ ID NO:26 5'-CCGTGGTGAACGCTCTGGACC-3' (nt 6932–6952). Interestingly, of the 40 nonspecific primers tested, only two yielded positive products on primer extension analysis and these two corresponded to an exact and a degenerate human sequence at the 3' end of the C2 domain: SEQ ID NO:27 5'-GTAGAGGTCCTGTGCCTCGCAGCC-3' (nt 7030–7053) and SEQ ID NO:28 5'-GTAGAGSTSCTGKGCCTCRCAKCCYAG-3', (nt 7027–7053). These primers had initially been designed to yield a product by conventional RT-PCR but failed to yield sufficient product that could be visualized by ethidium bromide dye binding. However, a PCR product could be identified by the more sensitive primer extension method. This product was gel-purified and directly sequenced. This extended the sequence of porcine fVIII 3' to nt 7026.

Additional sequence was obtained by primer extension analysis of a nested PCR product generated using the adaptor-ligated double-stranded cDNA library used in the 5'-RACE protocol described previously. The first round reaction used the porcine exact primer SEQ ID NO:29 5'-CTTCGCATGGAGTTGATGGGCTGT-3' (nt 6541–6564) and the AP1 primer. The second round reaction used SEQ ID NO:30 5'-AATCAGGACTCCTCCACCCCCG-31' (nt 6913–6934) and the AP2 primer. Direct PCR sequencing extended the sequence 3' to the end of the C2 domain (nt 7053). The C2 domain sequence was unique except at nt 7045 near the 3' end of the C2 domain. Analysis of repeated PCR reactions yielded either A, G or a double read of A/G at this site.

Sequencing was extended into the 3'UTR using two additional primers, SEQ ID NO:31 5'-GGA TCC ACC CCA CGA GCT GG-3' (nt 6977–6996) and SEQ ID NO:32 5'-CGC CCT GAG GCT CGA GGT TCT AGG-3' (nt 7008–7031). Approximately 15 bp of 3' UTR sequence were obtained, although the sequence was unclear at several sites. Several antisense primers then were synthesized based on the best estimates of the 3' untranslated sequence. These primers included the reverse complement of the TGA stop codon at their 3' termini. PCR products were obtained from both porcine spleen genomic DNA and porcine spleen cDNA that were visualized by agarose gel electrophoresis and ethidium bromide staining using a specific sense primer SEQ ID NO:33 5'-AAT CAG GAC TCC TCC ACC CCC G-3' (nt 6913–6934) and the 3' UTR antisense primer, SEQ ID NO:34 5'-CCTTGCAGGAATTCGATTCA-3'. To obtain sufficient quantities of material for cloning purposes, a second round of PCR was done using a nested sense primer, SEQ ID NO:35 5'-CCGTGGTGAACGCTCTGGACC-31' (nt 6932–6952) and the same antisense primer. The 141 bp PCR product was cloned into EcoRV-cut pBluescript II KS-. Sequence of three clones derived from genomic DNA and three clones derived from cDNA was obtained in both directions. The sequence was unambiguous except at nt 7045, where genomic DNA was always A and cDNA was always G.

Multiple DNA sequence alignments of human, porcine, and mouse fvIII (FIG. 1A–1H). Alignments of the signal peptide, A1, A2, A3, C1, and C2 regions were done using the CLUSTALW program (Thompson, J. D. et al. (1994) Nucleic. Acids. Res. 22:4673–4680). Gap open and gap extension penalties were 10 and 0.05 respectively. The alignments of the human, mouse, and pig B domains have been described previously (Elder et al. (1993) supra). The human A2 sequence corresponds to amino acids 373–740 in SEQ ID NO:2. The porcine A2 amino acid sequence is given in SEQ ID NO:4, and the mouse A2 domain amino acid sequence is given in SEQ ID NO:6, amino acids 392–759.

RESULTS AND DISCUSSION

We have determined the cDNA sequence of porcine fVIII corresponding to 137 bp of the 5' UTR, the signal peptide coding region (57 bp), and the A1 (1119 bp), A3 (990 bp), C1 (456 bp), and C2 (483 bp) domains. Along with previously published sequence of the B domain and light chain activation peptide regions (Toole et al. (1986) supra) and the A2 domain (Lubin et al. (1994) supra), the sequence reported here completes the determination of the porcine fVIII cDNA corresponding to the translated product. A fragment that included the 5' UTR region, signal peptide, and A1 domain cDNA was cloned using a 5'-RACE RT-PCR protocol. A primer based on human C2 sequence was successful in producing an RT-PCR product that led to cloning of the A3, C1, and 5' half of the C2 domain. The cDNA corresponding to the 3' half of the C2 domain and 3' UTR cDNA proved difficult to clone. The remainder of the C2 domain ultimately was cloned by a targeted gene walking PCR procedure (Parker et al. (1991) supra).

The sequence reported herein SEQ ID NO:36 was unambiguous except at nt 7045 near the 3' end of the C2 domain, which is either A or G as described hereinabove. The corresponding codon is GAC (Asp) or AAC (Asn). The human and mouse codons are GAC and CAG (Gln), respectively. Whether this represents a polymorphism or a reproducible PCR artifact is unknown. Recombinant hybrid human/porcine B-domainless fVIII cDNAs containing porcine C2 domain substitutions corresponding to both the GAC and AAC codons have been stably expressed with no detectable difference in procoagulant activity. This indicates that there is not a functional difference between these two C2 domain variants.

The alignment of the predicted amino acid sequence of full-length porcine fVIII SEQ ID NO:37 with the published human (Wood et al. (1984) supra) and murine (Elder et al. (1993) supra) sequences is shown in FIG. 1A–1H along with sites for post-translational modification, proteolytic cleavage, and recognition by other macromolecules. The degree of identity of the aligned sequences is shown in Table VII. As noted previously, the B domains of these species are more divergent than the A or C domains. This is consistent with the observation that the B domain has no known function, despite its large size (Elder et al. (1993) supra; Toole et al. (1986) supra). There is also more divergence of sequences corresponding to the A1 domain APC/factor IXa cleavage peptide (residues 337–372) and the light chain activation peptide (Table VII). The thrombin cleavage site at position 336 to generate the 337–372 peptide is apparently lost in the mouse since this residue is glutamine instead of arginine (Elder et al. (1993) supra). The relatively rapid divergence of thrombin cleavage peptides (or in mouse fVIII a possibly vestigial 337–372 activation peptide) has been previously noted for the fibrinopeptides (Creighton, T. E. (1993) In Proteins: Structures and Molecular Properties, W. H. Freeman, New York, pp. 105–138). Lack of biological function of these peptides once cleaved has been cited as a possible reason for the rapid divergence. Arg562 in human fVIII has been proposed to be the more important cleavage site for activated protein C during the inactivation of fVIII and fVIIIa (Fay, P. J. et al. (1991) J. Biol. Chem. 266:20139–20145). This site is conserved in human, porcine and mouse fVIII.

Potential N-linked glycosylation sites are also shown in bold in FIG. 1A–1H. There are eight conserved N-linked glycosylation sites: one in the A1 domain, one in the A2 domain, four in the B domain, one in the A3 domain, and one in the C1 domain. The 19 A and C domain cysteines are conserved, whereas there is divergence of B domain cysteines. Six of the seven disulfide linkages in fVIII are found at homologous sites in factor V and ceruloplasmin, and both C domain disulfide linkages are found in factor V (McMullen, B. A. et al. (1995) Protein Sci. 4:740–746). Human fVIII contains sulfated tyrosines at positions 346, 718, 719, 723, 1664, and 1680 (Pittman, D. D. et al. (1992) Biochemistry 31:3315–3325; Michnick, D. A. et al. (1994) J. Biol. Chem. 269::20095–20102). These residues are conserved in mouse fVIII and porcine fVIII (FIG. 1), although the CLUSTALW program failed to align the mouse tyrosine corresponding to Tyr346 in human fVIII.

Mouse and pig plasma can correct the clotting defect in human hemophilia A plasma, which is consistent with the level of conservation of residues in the A and C domains of these species. The procoagulant activity of porcine fVIII is superior to that of human fVIII (Lollar, P. et al. (1992) J. Biol. Chem. 267:23652–23657). This may be due to a decreased spontaneous dissociation rate of the A2 subunit from the active A1/A2/A3-C1-C2 fVIIIa heterotrimer. Whether this difference in procoagulant activity reflects an evolutionary change in function as an example of species adaptation (Perutz, M. F. (1996) Adv. Protein Chem. 36:213–244) is unknown. Now that the porcine fVIII cDNA sequence corresponding to the translated product is complete, homolog scanning mutagenesis (Cunningham, B. C., et al. (1989) Science 243:1330–1336) may provide a way to identify structural differences between human and porcine fVIII that are responsible for the superior activity of the latter.

Porcine fVIII is typically less reactive with inhibitory antibodies that arise in hemophiliacs who have been transfused with fVIII or which arise as autoantibodies in the general population. This is the basis for using porcine fVIII concentrate in the management of patients with inhibitory antibodies (Hay and Lozier (1995) supra). Most inhibitors are directed against epitopes located in the A2 domain or C2 domain (Fulcher, C. A. et al. (1985) Proc. Natl. Acad. Sci. USA 82:7728–7732; Scandella, D. et al. (1988) Proc. Natl. Acad. Sci. USA 85:6152–6156; Scandella, D. et al. (1989) Blood 74:1618–1626). Additionally, an epitope of unknown significance has been identified that is in either the A3 or C1 domain (Scandella et al. (1989) supra; Scandella, D. et al. (1993) Blood 82:1767–1775; Nakai, H. et al. (1994) Blood 84:224a). The A2 epitope has been mapped to residues 484–508 by homolog scanning mutagenesis (Healey et al. (1995) supra). In this 25 residue segment, there is relatively low proportion of identical sequence (16/25 or 64%). It is interesting that this region, which appears to be functionally important based on the fact that antibodies to it are inhibitory, apparently has been subjected to relatively more rapid genetic drift. Alignment of the porcine A2 domain and A3 domains indicate that the A2 epitope shares no detectable homology with the corresponding region in the A3 domain. The C2 inhibitor epitope has been located to within residues 2248–2312 by deletion mapping (Scandella, D. et al. (1995) Blood 86:1811–1819). Human and porcine fVIII are 83% identical in this 65 residue segment. Homolog scanning mutagenesis of this region to characterize the C2 epitope is underway. Alanine substitutions for individual amino acids, especially those which are non-identical between human/ porcine or human/mouse or which are most likely to contribute to antibody binding, can yield a modified factor VIII with reduced reactivity to inhibitory antibodies.

FIG. 1 Alignment of predicted amino acid sequences of human, porcine, and mouse fVIII. FIGS. 1A–1H taken together provide an aligned sequence comparison of the human, pig and mouse factor VIII amino acid sequences. FIG. 1A compares signal peptide regions (human, SEQ ID NO:40; porcine, SEQ ID NO:37, amino acids 1–19; murine, SEQ ID NO:6, amino acids 1–19). FIG. 1B gives the amino acid sequences for the A1 domain of human (SEQ ID NO:2, amino acids 1–372), porcine (SEQ ID NO:37, amino acids 20–391), and murine (SEQ ID NO:6, amino acids 20–391). FIG. 1C provides amino acid sequences for the Factor VIII A2 domains from human (SEQ ID NO:2, amino acids 373–740), pig (SEQ ID NO:37, amino acids 392–759) and mouse (SEQ ID NO:6, amino acids 392–759). FIG. 1D provides the amino acid sequences of B domains of human factor VIII (SEQ ID NO:2, amino acids 741–1648), pig (SEQ ID NO:37, amino acids 760–1449) and mouse (SEQ ID NO:6, amino acids 760–1640). FIG. 1E compares the amino acid sequences of Factor VIII light chain activation peptides of human, pig and mouse (SEQ ID NO:2, amino acids 1649–1689; SEQ ID NO:37, amino acids 1450–14909; and SEQ ID NO:6, amino acids 1641–1678, respectively). FIG. 1F provides the sequence comparison for human, pig and mouse Factor VIII A3 domains (SEQ ID NO:2, amino acids 1690–2019; SEQ ID NO:37, amino acids 1491–1820; and SEQ ID NO:6, amino acids 1679–2006, respectively. FIG. 1G provides the amino acid sequences of the Factor VIII C1 domains of human, pig and mouse (SEQ ID NO:2, amino acids 2020–2172; SEQ ID NO:37, amino acids 1821–1973; and SEQ ID NO:6, amino acids 2007–2159, respectively). FIG. 1H provides sequence data for the C2 domains of the Factor VIII C2 domains of human, pig and mouse (SEQ ID NO:2, amino acids 2173–2332; SEQ ID NO:37, amino acids 1974–2133; and SEQ ID NO:6, amino acids 2160–2319, respectively).

The diamonds represent tyrosine sulfation sites, potential glycosylation sites are in bold type, proposed binding sites for Factor IXa, phospholipid and Protein C are double-underlined, and regions involved in binding anti-A2 and anti-C2 inhibitory antibodies are italicized. Asterisks highlight amino acid sequences which are conserved. See also SEQ ID NO:36 (porcine factor VIII cDNA) and SEQ ID NO:37 (deduced amino acid sequence of porcine factor VIII). The human numbering system is used as the reference (Wood et al. (1984) supra). The A1, A2, and B domains are defined by thrombin cleavage sites at positions 372 and 740 and an unknown protease cleavage site at 1648 as residues 1–372, 373–740, and 741–1648, respectively (Eaton, D. L. et al. (1986) *Biochemistry* 25:8343–8347). The A3, C1, and C2 domains are defined as residues 1690–2019, 2020–2172, and 2173–2332, respectively (Vehar et al. (1984) supra). Cleavage sites for thrombin (factor IIa), factor IXa, factor Xa and APC (Fay et al. (1991) supra; Eaton, D. et al. (1986) *Biochemistry* 25:505–512;Lamphear, B. J. and P. J. Fay (1992) *Blood* 80:3120–3128) are shown by placing the enzyme name over the reactive arginine. An acidic peptide is cleaved from the fVIII light chain by thrombin or factor Xa at position 1689. Proposed binding sites for factor IXa (Fay, P. J. et al. (1994) *J. Biol. Chem.* 269:20522–20527; Lenting, P. J. et al. (1994) *J. Biol. Chem.* 269:7150–7155), phospholipid (Foster, P. A. et al. (1990) *Blood* 75:1999–2004) and protein C (Walker, F. J. et al. (1990) *J. Biol. Chem.* 265:1484–1489) are doubly underlined. Regions involved in binding anti-A2 (Lubin et al. (1994) supra; Healey et al. (1995) supra) and anti-C2 (Scandella et al. (1995) supra) inhibitory antibodies are italicized. Tyrosine sulfation sites (Pittman et al. (1992) supra; Michnick et al. (1994) supra) are shown by ♦. Recognition sequences for potential N-linked glycosylation (NXS/T, where X is not proline) are shown in bold.

The nucleotide sequence encoding the factor VIII protein lacking the B domain is given in SEQ ID NO:38, and the corresponding deduced amino acid sequence is provided in SEQ ID NO:39.

TABLE VII

Identical residues in the alignment of human, porcine and mouse fVIII

| Domain | Human-Pig | Human-Mouse | Pig-Mouse |
|---|---|---|---|
| Signal peptide | 14/19 (73) | 12/19 (63) | 8/19 (42) |
| A1$_{des\ 337-372}$ | 258/336 (79) | 291/336 (87) | 256/337 (76) |
| 337-372 | 23/36 (64) | 13/36 (36) | 12/36 (33) |
| A2 | 309/368 (84) | 299/368 (81) | 289/368 (78) |
| B | 353/690 (51) | 470/881 (53) | 280/663 (42) |
| LC activation peptide | 23/41 (56) | 22/39 (56) | 19/39 (49) |
| A3 | 280/330 (85) | 281/330 (85) | 267/330 (81) |
| C1 | 137/152 (90) | 139/152 (91) | 131/152 (86) |
| C2 | 123/161 (76) | 131/161 (81) | 114/161 (71) |

Per cent identity is shown in parentheses.

Abbreviations used: fVIII, factor VIII; nt, nucleotide; RT, reverse transcriptase; PCR, polymerase chain reaction; 3'- or 5'-RACE, 3'- or 5' rapid amplification of cDNA ends; UTR, untranslated region, dNTP, deoxynucleotide triphosphate. IUPAC nomenclature is used for base abbreviations where A is adenine, C is cytosine, T is thymine, G is guanine, N is A, C, T, or G; R is A or G; Y is C or T; K is T or G; S is C or G; and Y is C or T.

Although only preferred embodiments are specifically illustrated and described herein, it will be appreciated that many modifications and variations of the present invention are possible in light of the above teachings and within the purview of the appended claims without departing from the spirit and intended scope of the invention.

I claim:

1. Modified human factor VIII comprising an amino acid substitution at one or more of position 484, 485, 487, 488, 489, 492, 495, 501 or 508, according to SEQ ID NO:2, said substitution being insertion of an immunoreactivity-reducing amino acid for the naturally-occurring amino acid, said modified factor VIII having procoagulant activity.

2. The modified factor VIII of claim 1 wherein at least one substituted amino acid is alanine.

3. The modified factor VIII of claim 1 lacking a B-domain.

4. The modified factor VIII of claim 3 comprising alanine substituted for arginine at position 484.

5. The modified factor VIII of claim 3 comprising alanine substituted for proline at position 485.

6. The modified factor VIII of claim 3 comprising alanine substituted for tyrosine at position 487.

7. The modified factor VIII of claim 3 comprising alanine substituted for serine at position 488.

8. The modified factor VIII of claim 3 comprising alanine substituted for arginine at position 489.

9. The modified factor VIII of claim 3 comprising alanine substituted for proline at position 492.

10. The modified factor VIII of claim 3 comprising alanine substituted for valine at position 495.

11. The modified factor VIII of claim 3 comprising alanine substituted for phenylalanine at position 501.

12. The modified factor VIII of claim 3 comprising alanine substituted for isoleucine at position 508.

13. A method for modifying a factor VIII such that reactivity to an inhibitory antibody is reduced and procoagulant activity is retained, consisting essentially of substituting an immunoreactivity-reducing amino acid for the naturally-occurring amino acid at least one of positions 484, 485, 487, 488, 489, 492, 495, 501, or 508 according to SEQ ID NO:2.

14. The method of claim 13 wherein at least one substituted amino acid is alanine.

15. The method of claim 13 comprising substituting an alanine for proline at position 485.

16. The method of claim 13 comprising substituting an alanine for tyrosine at position 487.

17. The method of claim 13 comprising substituting an alanine for serine at position 488.

18. The method of claim 13 comprising substituting an alanine for arginine at position 489.

19. The method of claim 13 comprising substituting an alanine for proline at position 492.

20. The method of claim 13 comprising substituting an alanine for valine at position 495.

21. The method of claim 13 comprising substituting an alanine for phenylalanine at position 501.

22. The method of claim 13 comprising substituting an alanine for isoleucine at position 508.

* * * * *

UNITED STATES PATENT AND TRADEMARK OFFICE
CERTIFICATE OF CORRECTION

PATENT NO. : 5,859,204

DATED : January 12, 1999

INVENTOR(S) :
John S. Lollar

It is certified that error appears in the above-identified patent and that said Letters Patent is hereby corrected as shown below:

At col. 8, line 63, replace "non-hum,an" with --non-human--.

At col. 17, line 45, replace "*Coapul.*" with --*Coagul.*--.

At col. 25, line 29, replace "tractor" with --factor--.

At col. 27, line 48, replace "vwf" with --vWf--.

At col. 28, line 16, replace "40°C." with --4°C.--

At col. 32, line 60, replace "nil" with --ml--.

At col. 42, line 49, replace "pbluescript" with --pBluescript--.

At col. 44, line 16, the next to last triplet, "ATG" should be in boldface type, i.e. --ATG--.

In the claims:

In claim 13, line 5, insert "at" between "at" and "least".

Signed and Sealed this

Fifteenth Day of June, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,859,204
DATED : January 12, 1999
INVENTOR(S) : Lollar

It is certified that error appears in the above-identified patent and that said Letters Patent is hereby corrected as shown below:

Drawings,
The requested corrections are: for FIG. 1D, after 1189
Insert lines 1239, 1287, 1337 and 1387 of human factor VIII amino acid sequences, together with the corresponding porcine and murine sequences as set forth in substitute Fig. 1D Signed and Sealed this Twenty-third Day of April, 2002

Attest:

Attesting Officer

JAMES E. ROGAN
Director of the United States Patent and Trademark Office

B domain

```
Human  741 SFSQNSRHPS TRQKQFNATT IPENDIEKTD PWEAHRTPMP KIQNVSSSDL
Pig        SFAQNSRPPS ASQKQFQTIT SPEDDVE-LD PQSGERTQAL EELSVPSGDG
Mouse      SFFQNTNHPN TRKKKFKDST IPKNDMEKIE PQFEEIAEML KVQSVSVSDM
           ** **   *   * *    *   *   * **   *              *   *

791 LMLLRQS-PT PHGLSLSDLQ EAKYETFSDD PSPGAIDSNN SLSEMTHFRP
           SMLLGQN-PA PHGSSSSDLQ EARNEA--DD YLPGARERNT APSAAARLRP
           LMLLGQSHPT PHGLFLSDGQ EAIYEAIHDD HSPNAIDSNE GPSKVTQLRP
           *** *      ***     *  * **  *     * *   *          **

840 QLHHSGDMVF TPESGLQLRL NEKLGTTAAT ELKKLDFKVS ST-SNNLIS-
           ELHHSAERVL TPEP------ ------EK    ELKKLDSKMS SSSDLLKTSP
           ESHHSEKIVF TPQPGLQLRS NKSLETTIEV KWKKLGLQVS SLPSNLMTT-
            ***   *   **                    ***  *      *  *

888 TIPSDNLAAGT DNTSSLGPPS MPVHYDSQLD TTLFGKKSSP LTESGGPLSL
           TIPSDTLSAET ERTHSLGPPH PQVNFRSQLG AIVLGKNSSH FIGAGVPLGS
           TILSDNLKATF EKTDSSGFPD MPVHSSSKLS TTAFGKKAYS LVGSHVPLNA
           ** ** * *   * * *      * *        *  *          **

939 SEENNDSKLL ESGLMNSQES SWGKNVSSTE SGRLFKGKRA HGPALLTKDN
           TEED------ -------HES SLGENVSPVE SDGIFEKERA HGPASLTKDD
           SEENSDSNIL DSTLMYSQES LPRDNILSIE NDRLLREKRF HGIALLTKDN
            **               **     *   *       *     ** * ****

989 ALFKVSISLL KTNKTSNNSA TNRKTHIDGP SLLIENSPSV WQNILESDTE
           VLFKVNISLV KTNKARVYLK TNRKIHIDDA ALLTENRAS- ----------
           TLFKDNVSLM KTNKTYNHST TNEKLHTESP TSIENSTTDL QDAILKVNSE
            ***    **  **** ****  **  *

1039 FKKVTPLIHD RMLMDKNATA LRLNHMSNKT TSSKNMEMVQ QKKEGPIPPD
           ---------- ATFMDKNTTA SGLNHVSN-- ---------- ----------
           IQEVTALIHD GTLLGKNSTY LRLNHMLNRT TSTKNKDIFH RKDEDPIPQD
             *  ***    **      *  *** *

1089 AQNPDMSFFK MLFLPESARW IQRTHGKNSL NSGQGPSPKQ LVSLGPEKSV
           ---------- --------W  IKGPLGKNPL SSERGPSPEL LTSSGSGKSV
           EENTIMPFSK MLFLSESSNW FKKTNGNNSL NSEQEHSPKQ LVYLMFKKYV
                          *       *  * ***  *   **  *      *  *

1139 EGQNFLSEKN KVVVGKGEFT KDVGLKEMVF PSSRNLFLTN LDNLHENNTH
           KGQSSGQGRI RVAVEEEELS KG---KEMML PNSELTFLTN SADVQGNDTH
           KNQSFLSEKN KVTVEQDGFT KNIGLKDMAF PHNMSIFLTT LSNVHENGRH
            *            *  *     *   *   *    ***          * *

1189 NQEKKIQEEI EKKETLIQEN VVLPQIHTVT GTKNFMKNLF LLSTRQNVEG
           SQGKKSREEM ERREKLVQEK VDLPQVYTAT GTKNFLRNIF HQSTEPSVEG
           NQEKNIQEEI EK-EALIEEK VVLPQVHEAT GSKNFLKDIL ILGTRQNI--
            *    *    **   *  *  * ***    * * ***

1239 SYDGAYAPVL QDFRSLNDST NRTKKHTAHF SK--KGEEEN LEGLGNQTKQ
           FDGGSHAPVP QDSRSLNDSA ERAETHIAHF SAIR--EEAP LEAPGNRT--
           SLYEVHVPVL QNITSINNST NTVQIHMEHF FKRRKDKETN SEGLVNKTRE
                  **  *   *  *   *  *  ***       *    *   *   *
```

FIG. 1D

```
1287  IVEKYACTTR ISPNTSQQNF VTQRSKRALK QFRLPLEETE LEKRIIVDDT
      ---------- ---GPGPRSA VPRRVKQSLK QIRLPLEEIK PERGVVLNAT
      MVKNYP---- -----SQKNI TTQRSKRALG QFRL------ ----------

1337  STQWSKNMKH LTPSTLTQID YNEKEKGAIT QSPLSDCLTR SHSIPQANRS
      STRWS----- ---------- ---------- ---------- ----------
      STQWLKTINC STQCIIKQID HSKEMKKFIT KSSLSDS-SV IKSTTQTNSS
      ** *

1387  PLPIAKVSSF PSIRPIYLTR VLFQDNSSHL PAASY----R KKDSGVQESS
      ---------- ---------- ---------- ---------- -------ESS
      DSHIVKTSAF P---PIDLKR SPFQNKFSHV QASSYIYDFK TKSSRIQESN
                                                      **

1433  HFLQGAKKNN LSLAILTLEM TGDQREVGSL GTSATNSVTY KKVENTVLPK
      PILQGAKRNN LSLPFLTLEM AGGQGKISAL GKSAAGPLAS GKLEKAVLSS
      NFLKETKINN PSLAILPWNM FIDQGKFTSP GKSNTNSVTY KKRENIIFLK
       *  * **  **  *   *       *        * *         *  *

1483  PDLPKTSGKV ELLPKVHIYQ KDLFPTETSN GSPGHLDLVE GSLLQGTEGA
      AGLSEASGKA EFLPKVRVHR EDLLPQKTSN VSCAHGDLGQ EIFLQKTRGP
      PTLPEESGKI ELLPQVSIQE EEILPTETSH GSPGHLNLMK EVFLQKIQGP
         ***   * ** *        *  *  *   *   *  *   *** *

1533  IKWNEANRPG KVPFLRVATE SSAKTPSKLL DPLAWDNHYG TQIPKEEWKS
      VNLNKVNRPG ---------- ---RTPSKLL ---------G PPMPKE-WES
      TKWNKAKRHG ESIKGKTES- -SKNTRSKLL NHHAWDYHYA AQIPKDMWKS
       * **              *       ****                  * *

1583  QEKSPEKTAF KKKDTI-LSLN ACESNHAIAA INEGQNKPEI EVTWAKQGRT
      LEKSPKSTAL RTKDIISLPLD RHESNHSIAA KNEGQAETQR EAAWTKQGGP
      KEKSPEIISI KQEDTI-LSLR PHGNSHSIGA -NEKQNWPQR ETTWVKQGQT
      ****        *  *         ** *  **   *          * ***

1633  ERLCSONPPY LKRHQR
      GRLCAPKPPV LRRHQR
      QRTCSQIPPV LKRHQR
       * *  *** * ****
```

Light chain activation peptide
                ♦                    ♦   IIa/Xa
Human  1649  EITRTTLQSDQEEIDYDDTISVEMKKEDFDIYDEDENQSPR
Pig          DISLPTFQPEEDKMDYDDIFSTETKGEDFDIYGEDENQDPR
Mouse        EL--SAFQSEQEATDYDDAITIET-IEDFDIYSEDIKQGPR
              *      *    ****  *  ****    * **

FIG. 1E

A3 domain

```
                                              IXa Xa
Human 1690 SFQKKTRHYF IAAVERLWDY GMSSSPHVLR NRAQSGSVPQ FKKVVFQEET
Pig        SFQKRTRHYF IAAVEQLWDY GMSESPRALR NRAQNGEVPR FKKVVFREFA
Mouse      SVQQKTRHYF IAAVERLWDY GMSTS-HVLR NRYQSDNVPQ FKKVVFQEFT
           * *  ***** *****.**** *** *  ** ** *   **  ****** **

1740 DGSFTQPLYR GELNEHLGLL GPYIRAEVED NIMVTFRNQA SRPYSFYSSL
           DGSFTQPSYR GELNKHLGLL GPYIRAEVED NIMVTFKNQA SRPYSFYSSL
           DGSFSQPLYR GELNEHLGLL GPYIRAEVED NIMVTFKNQA SRPYSFYSSL
           ****  **.** **** ***** ********** ****** *** **********
                                 Factor IXa binding
      1790 ISYEEDQRQG AEPRKNFVKP NETKTYFWKV QHHMAPTKDE FDCKAWAYFS
           ISYPDDQEQG AEPRHNFVQP NETRTYFWKV QHHMAPTEDE FDCKAWAYFS
           ISYKEDQR-G EEPRRNFVKP NETKIYFWKV QHHMAPTEDE FDCKAWAYFS
           *** **  *  *** *** * *** ***** ********** **********

1840 DVDLEKDVHS GLIGPLLVCH TNTLNPAHGR QVTVQEFALF FTIFDETKSW
           DVDLEKDVHS GLIGPLLICR ANTLNAAHGR QVTVQEFALF FTIFDETKSW
           DVDLERDMHS GLIGPLLICH ANTLNPAHGR QVSVQEFALL FTIFDETKSW
           ***** * ** ******* *   **** **** ** ****** **********

1890 YFTENMERNC RAPCNIQMED PTFKENYRFH AINGYIMDTL PGLVMAQDQR
           YFTENVERNC RAPCHLQMED PTLKENYRFH AINGYVMDTL PGLVMAQNQR
           YFTENVKRNC KTPCNFQMED PTLKENYRFH AINGYVMDTL PGLVMAQDQR
           *****  ***    **  *** ** ******* ********** *******  **

1940 IRWYLLSMGS NENIHSIHFS GHVFTVRKKE EYKMALYNLY PGVFETVEML
           IRWYLLSMGS NENIHSIHFS GHVFSVRKKE EYKMAVYNLY PGVFETVEML
           IRWYLLSMGN NENIQSIHFS GHVFTVRKKE EYKMAVYNLY PGVFETLEMI
           ********* ****.***** ****.***** ***** **** ****** **
                   Protein C binding
      1990 PSKAGIWRVE CLIGEHLHAG MSTLFLVYSN
           PSKVGIWRIE CLIGEHLQAG MSTTFLVYSK
           PSRAGIWRVE CLIGEHLQAG MSTLFLVYSK
           ** .****.* ********.** **.*** ******
```

FIG. 1F